United States Patent
Wuhr et al.

(10) Patent No.: US 10,145,818 B2
(45) Date of Patent: Dec. 4, 2018

(54) ACCURATE AND INTERFERENCE-FREE MULTIPLEXED QUANTITATIVE PROTEOMICS USING MASS SPECTROMETRY

(71) Applicant: President and Fellows of Harvard College, Cambridge, MA (US)

(72) Inventors: Martin Helmut Wuhr, Malden, MA (US); Steven P. Gygi, Foxborough, MA (US); Wilhelm Haas, Cambridge, MA (US); Graeme Conrad McAlister, Cambridge, MA (US); Leonid Peshkin, Boston, MA (US); Ramin Rad, Los Angeles, CA (US); Marc W. Kirschner, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/437,312

(22) PCT Filed: Oct. 22, 2013

(86) PCT No.: PCT/US2013/066010
§ 371 (c)(1),
(2) Date: Apr. 21, 2015

(87) PCT Pub. No.: WO2014/066284
PCT Pub. Date: May 1, 2014

(65) Prior Publication Data
US 2015/0293058 A1    Oct. 15, 2015

Related U.S. Application Data

(60) Provisional application No. 61/716,806, filed on Oct. 22, 2012.

(51) Int. Cl.
*G01N 27/62* (2006.01)
*G01N 33/68* (2006.01)
*H01J 49/00* (2006.01)

(52) U.S. Cl.
CPC ............ *G01N 27/62* (2013.01); *G01N 33/68* (2013.01); *G01N 33/6848* (2013.01);
(Continued)

(58) Field of Classification Search
None
See application file for complete search history.

(56) References Cited

U.S. PATENT DOCUMENTS 4,849,628 A    7/1989    McLuckey et al.
5,696,376 A    12/1997    Doroshenko et al.
(Continued)

FOREIGN PATENT DOCUMENTS

EP    1385194 A2    1/2004
JP    2008-519410 A    6/2008
(Continued)

OTHER PUBLICATIONS

Second, T. P. et al. Dual-Pressure Linear Ion Trap Mass Spectrometer Improving the Analysis of Complex Protein Mixtures, 2009, Analytical Chemistry, vol. 81, pp. 7757-7765.*
(Continued)

*Primary Examiner* — Xiaoyun R Xu
(74) *Attorney, Agent, or Firm* — Wolf, Greenfield & Sacks, P.C.

(57) ABSTRACT

Embodiments are directed to a method, a computer readable medium encoded with instructions that, when executed, perform a method, and a system for performing mass spectrometry analysis. Molecules of different samples may be labeled with a chemical tag, allowing a multiplexed analysis of multiple samples. The labeled molecules may be
(Continued)

fragmented, each fragmented molecule creating at least two separate ions. The relative abundance of each of the heavier ions, which may comprise the original molecule from the sample, may be measured. A relative abundance of the labeled molecules in each of the samples may be determined from the measured relative abundances of the heavier ions.

13 Claims, 39 Drawing Sheets

(52) U.S. Cl.
CPC ....... *H01J 49/0031* (2013.01); *H01J 49/0045* (2013.01); *H01J 49/0072* (2013.01)

(56) References Cited

U.S. PATENT DOCUMENTS

| | | | |
|---|---|---|---|
| 7,569,814 B2 | 8/2009 | Hashimoto et al. | |
| 7,919,745 B2 | 4/2011 | Shilov et al. | |
| 9,437,407 B2 | 9/2016 | McAlister et al. | |
| 2002/0192708 A1 | 12/2002 | Steen et al. | |
| 2004/0072251 A1 | 4/2004 | Anderson | |
| 2005/0242278 A1 | 11/2005 | Syage et al. | |
| 2007/0084994 A1 | 4/2007 | Wang et al. | |
| 2008/0044857 A1 | 2/2008 | Anderson | |
| 2008/0230691 A1 | 9/2008 | Hager | |
| 2009/0194688 A1 | 8/2009 | Bateman et al. | |
| 2009/0283673 A1 | 11/2009 | Shilov et al. | |
| 2010/0084547 A1 | 4/2010 | Pringle et al. | |
| 2010/0311176 A1 | 12/2010 | Williamson et al. | |
| 2011/0006200 A1 | 1/2011 | Loboda | |
| 2011/0111513 A1 | 5/2011 | Baumann et al. | |
| 2011/0297823 A1 | 12/2011 | Coon et al. | |
| 2011/0318771 A1* | 12/2011 | Li .................... | G01N 33/6848 435/27 |
| 2012/0044857 A1 | 2/2012 | Kim et al. | |
| 2012/0091330 A1 | 4/2012 | Coon et al. | |
| 2012/0178118 A1 | 7/2012 | Pi et al. | |
| 2012/0261568 A1 | 10/2012 | Coon et al. | |
| 2012/0305762 A1 | 12/2012 | Kaneko et al. | |
| 2013/0183704 A1* | 7/2013 | Shin .................... | C07C 233/47 435/23 |
| 2013/0334414 A1 | 12/2013 | McAlister et al. | |
| 2014/0364337 A1 | 12/2014 | Hermanson et al. | |
| 2016/0020083 A1 | 1/2016 | McAlister et al. | |

FOREIGN PATENT DOCUMENTS

| | | | |
|---|---|---|---|
| JP | 2010-249838 A | 11/2010 | |
| JP | 2012-186180 A | 9/2012 | |
| WO | WO 01/86306 A2 | 11/2001 | |
| WO | WO 01/94935 A2 | 12/2001 | |
| WO | WO 02/052259 A1 | 7/2002 | |
| WO | WO 2006/084130 A3 | 8/2006 | |
| WO | WO 2006/086540 A1 | 8/2006 | |
| WO | WO 2007/087534 A2 | 8/2007 | |
| WO | WO 2008/142579 A2 | 11/2008 | |
| WO | WO 2010/109022 A1 | 9/2010 | |
| WO | WO 2012/026743 * | 3/2012 | ............. G01N 33/68 |
| WO | WO 2012/051392 A2 | 4/2012 | |
| WO | WO 2012/164378 A2 | 12/2012 | |

OTHER PUBLICATIONS

Costa, K.D. et al. Model Fitting and Error Estimation, 2010, BSR 1803, Systems Biology: Biomedical Modeling, retrieved from internet site: file:///C:/Users/xxu/Documents/e-Red%20Folder/14437312/Costa%202010.pdf.*

Dasari, S., et al. Quantification of Isotopically Overlapping Deamidated and 18O-Labeled Peptides Using Isotopic Envelope Mixture Modeling, 2009, Journal of Proteome Research, vol. 8, pp. 1263-1270.*
13848897.8, May 12, 2016, Extended European Search Report.
PCT/US2013/040395, Sep. 13, 2013, International Search Report and Written Opinion.
PCT/US2013/040395, Dec. 4, 2014, International Preliminary Report on Patentability.
PCT/US2014/023851, Jul. 21, 2014, International Search Report and Written Opinion.
PCT/US2014/023851, Sep. 24, 2015, International Preliminary Report on Patentability.
PCT/US2014/041686, Sep. 25, 2014, Invitation to Pay Additional Fees.
PCT/US2014/041686, Jan. 9, 2015, International Search Report and Written Opinion.
PCT/US2014/041686, Dec. 23, 2015, International Preliminary Report on Patentability.
Office Communication dated Aug. 20, 2015 for U.S. Appl. No. 13/901,137.
Office Action for U.S. Appl. No. 13/901,137 dated Aug. 20, 2015.
Extended European Search Report for European Application No. EP 13848897.8 dated May 12, 2016.
International Search Report and Written Opinion for International Application No. PCT/US2013/040395 dated Sep. 13, 2013.
International Preliminary Report on Patentability for Application No. PCT/US2013/040395 dated Dec. 4, 2014.
International Search Report and Written Opinion for Application No. PCT/US2014/023851 dated Jul. 21, 2014.
International Preliminary Report on Patentability for Application No. PCT/US2014/023851 dated Sep. 24, 2015.
Invitation to Pay Additional Fees for Application No. PCT/US2014/041686 dated Sep. 25, 2014.
International Search Report and Written Opinion for Application No. PCT/US2014/041686 dated Jan. 9, 2015.
International Preliminary Report on Patentability for Application No. PCT/US2014/041686 dated Dec. 23, 2015.
Savitski et al., Delayed fragmentation and optimized isolation width settings for improvement of protein identification and accuracy of isobaric mass tag quantification on Orbitrap-type mass Anal Chem. Dec. 2011; 83(23):8959-67. doi: 10.1021/ac201760x.
International Search Report and Written Opinion for International Application No. PCT/US17/35446 dated Sep. 26, 2017.
Arnott et al., Selective Detection of Membrane Proteins Without Antibodies. Research. The American Society for Biochemistry and Molecular Biology, Inc. Molecular and Cellular Proteomics 1.2. 2002. 9 pages.
Borisov et al., Low-Energy Collision-Induced Dissociation Fragmentation Analysis of Cysteinyl-Modified Peptides. Anal. Chem. 2002;74:2284-92.
Byers et al., Candidate verification of iron-regulated Neisseria meningitidis proteins using isotpic versions of tandem mass tags (TMT) and single reaction monitoring. Journal of Proteomics 2009;73:231-9.
Mertins et al., iTRAQ Labeling is Superior to mTRAQ for Quantitative Global Proteomics and Phosphoproteomics. Technological Innovation and Resources. 2012. 12 pages.
Yan et al., Index-ion Triggered MS2 Ion Quantification: A Novel Proteomics Approach for Reproducible Detection and Quantification of Targeted Proteins in Complex Mixtures. Technological Innovation and Resources. 2011. 16 pages.
International Search Report and Written Opinion dated Jan. 17, 2014, by the Korean Intellectual Property Office in the international application No. PCT/US2013/066010, filed Oct. 22, 2013, 9 pages.
International Search Report and Written Opinion for Application No. PCT/US2013/066010 dated Jan. 17, 2014.
International Preliminary Report on Patentability for Application No. PCT/US2013/066010 dated May 7, 2015.

* cited by examiner

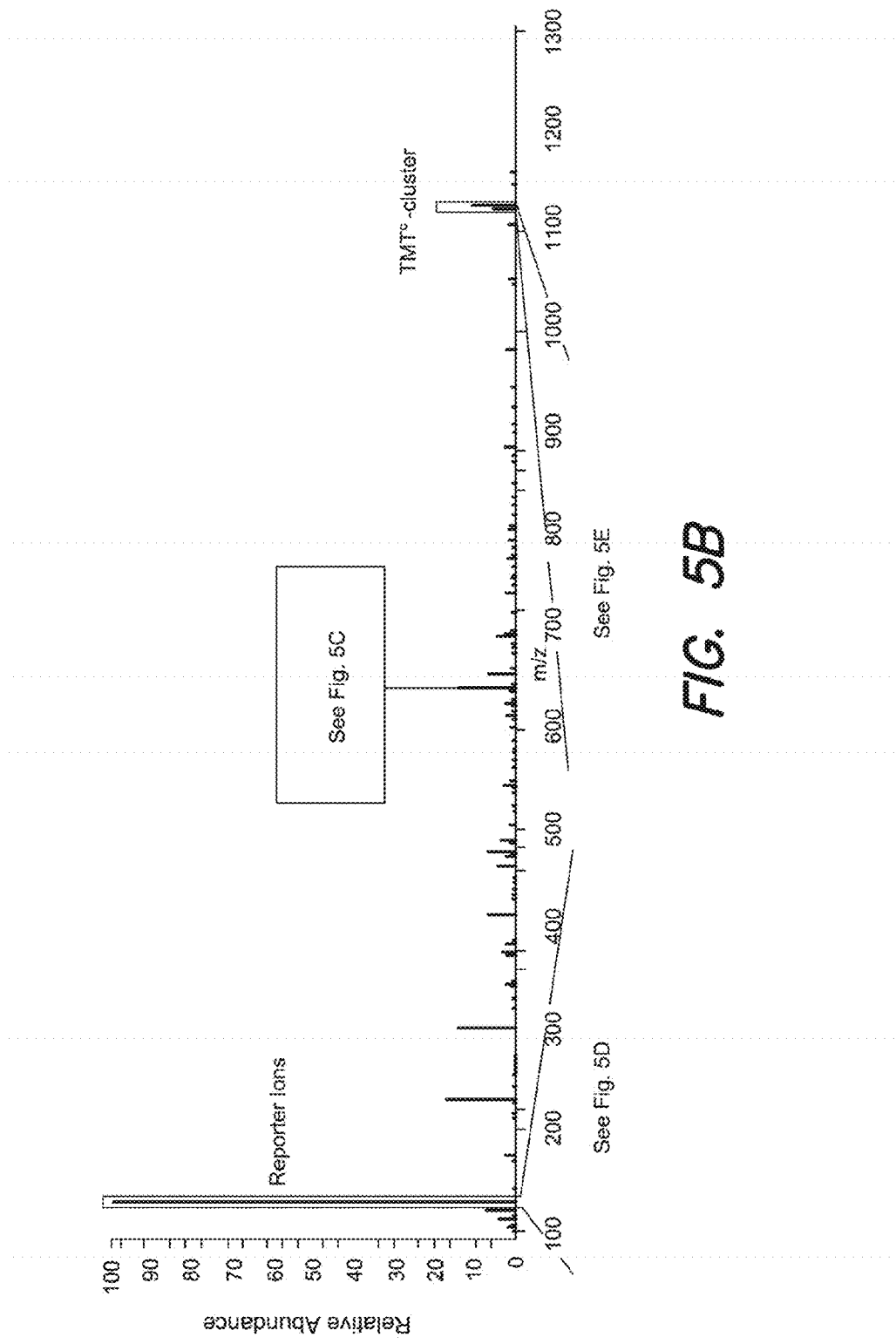

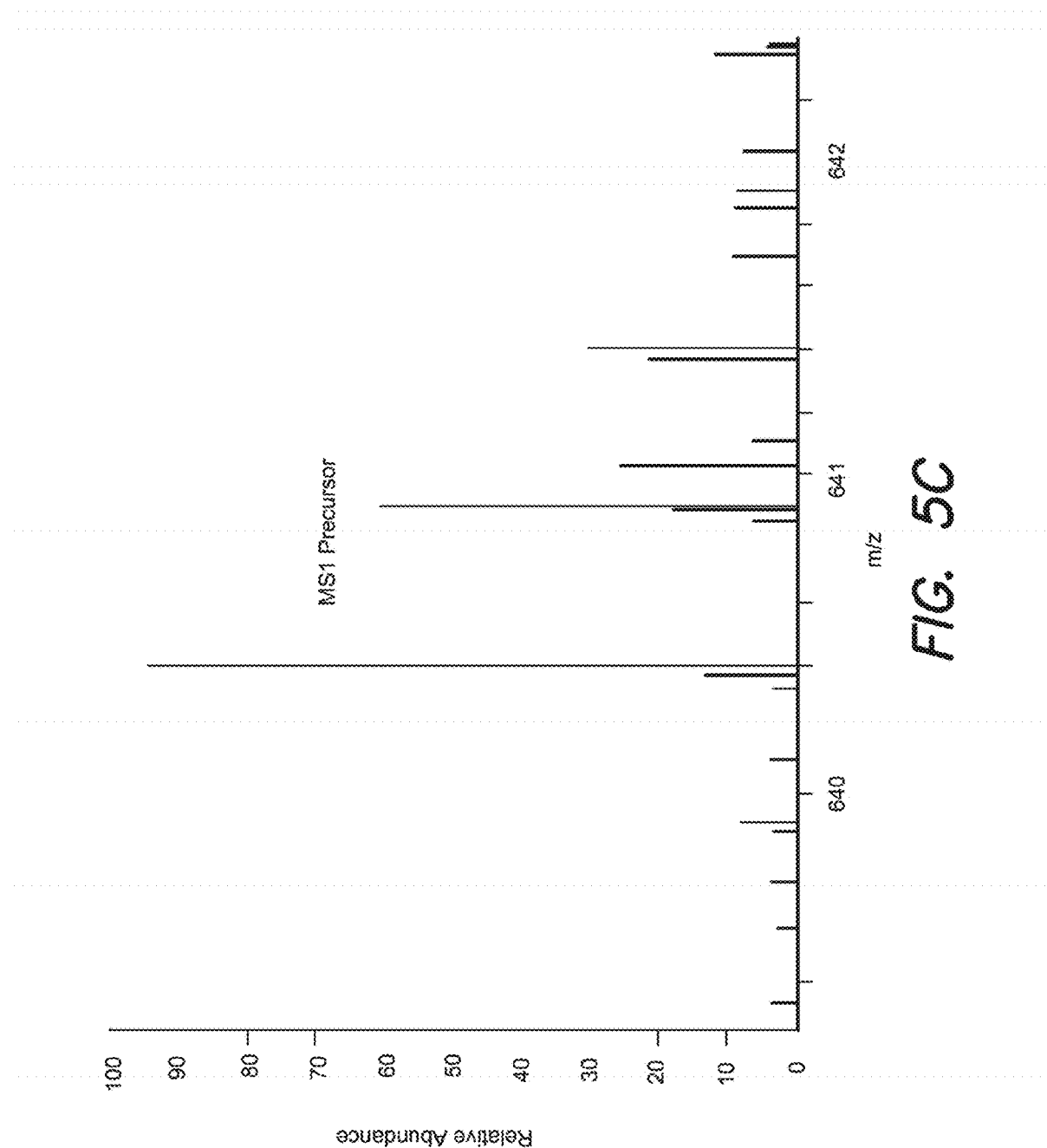

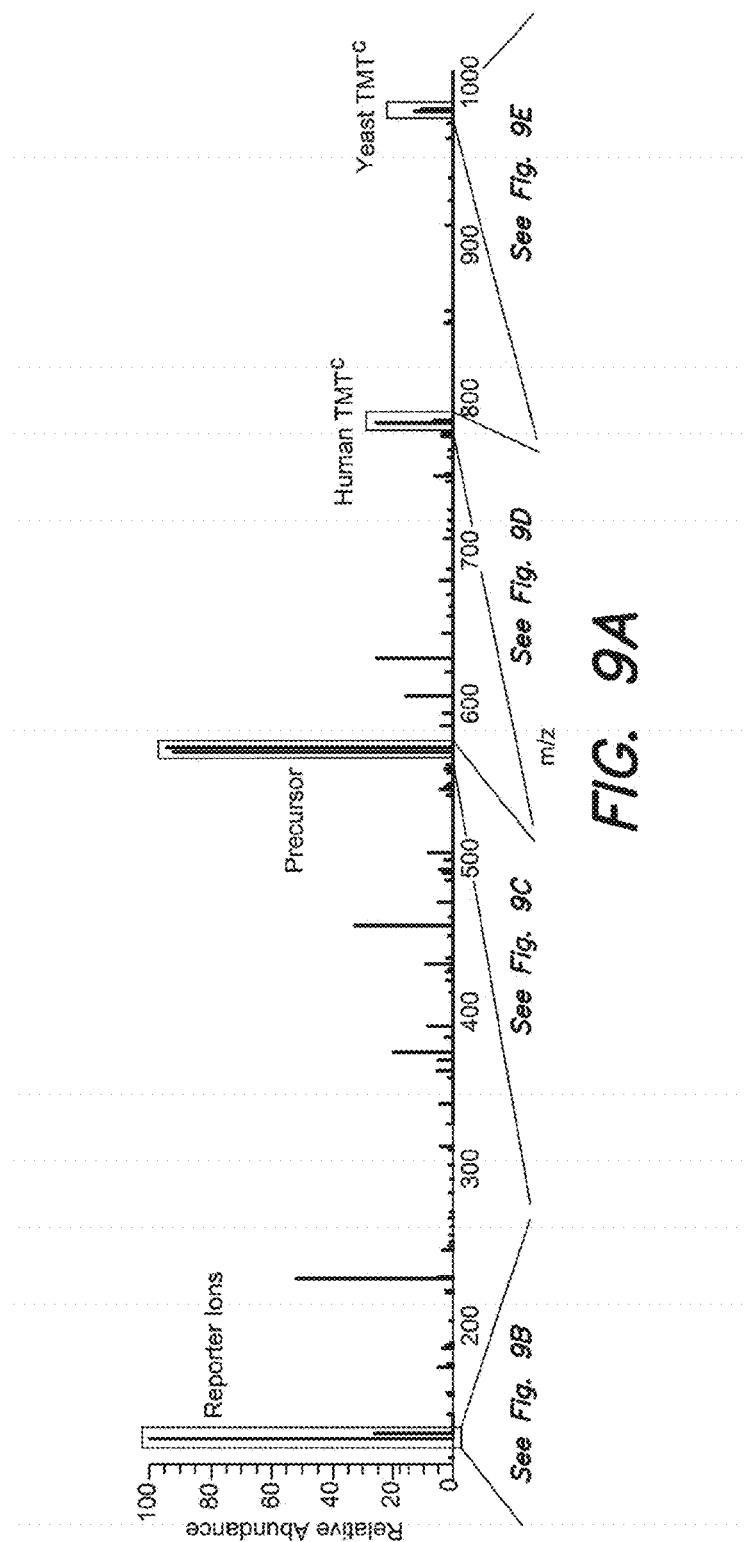

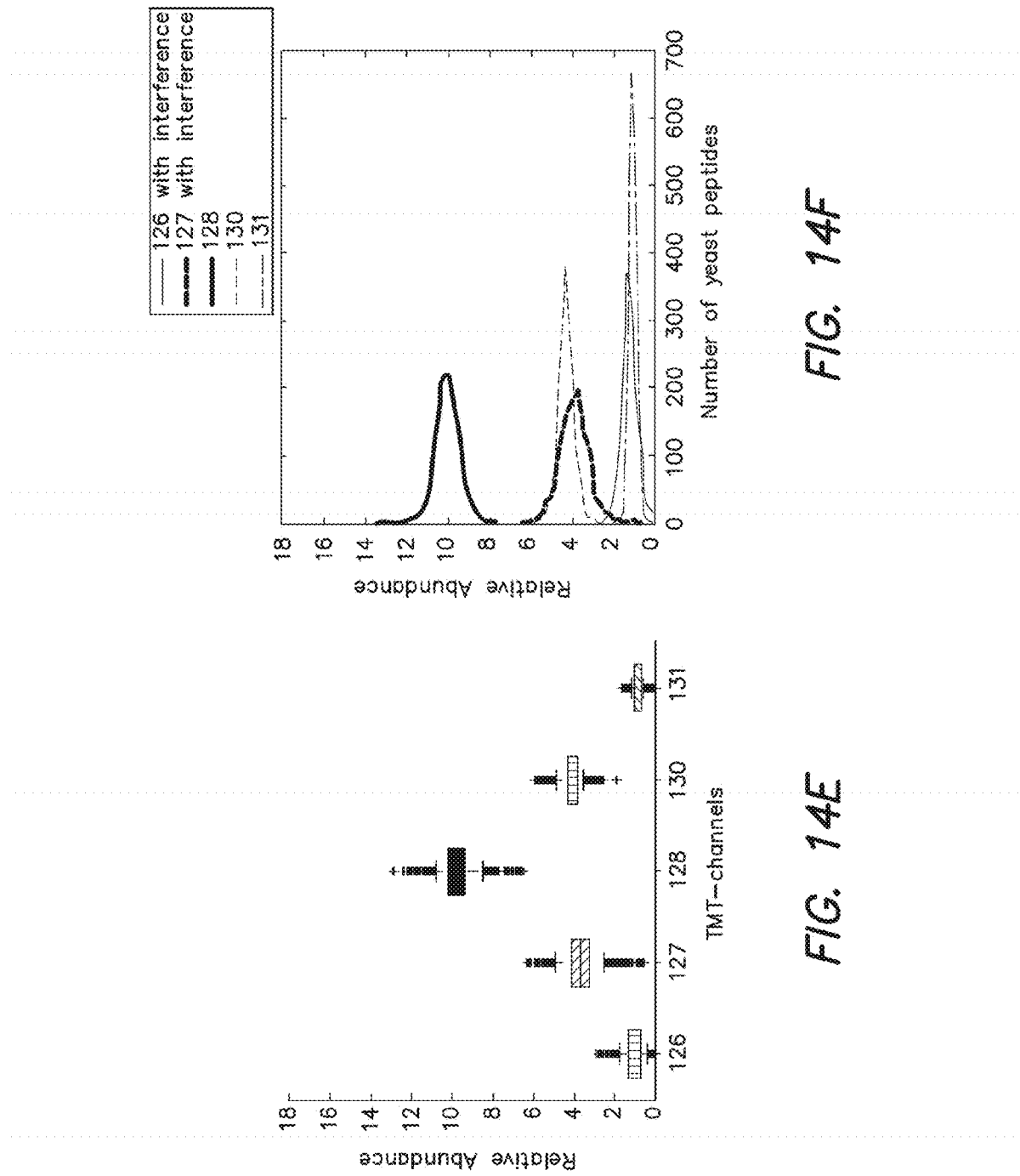

|  | +1.5 m/z, 35k, 240ms inj-time | +2 m/z, 35k, 240ms inj-time | +2.5 m/z, 35k, 240ms inj-time | +3 m/z, 35k, 240ms inj-time | +2 m/z, 18k, 60ms inj-time | +2 m/z, 35k, 120ms inj-time | +2 m/z, 70k, 240ms inj-time |
|---|---|---|---|---|---|---|---|
| Acquired MS2 spectra | 131118 | 13384 | 13555 | 13524 | 33087 | 22024 | 11109 |
| Identified peptides (FDR 1%) | 6266 | 6071 | 5902 | 3981 | 13640 | 9390 | 4514 |
| Identified yeast peptides | 2850 | 2775 | 2717 | 2699 | 5612 | 4029 | 2140 |
| >1000 ions in TMT C cluster | 1375 | 1389 | 1332 | 1243 | 1138 | 1567 | 982 |
| After "Goodness of Fit" filter | 1185 | 1185 | 1118 | 1037 | 757 | 1291 | 912 |

FIG. 15C

ACCURATE AND INTERFERENCE-FREE MULTIPLEXED QUANTITATIVE PROTEOMICS USING MASS SPECTROMETRY

RELATED APPLICATIONS

The present patent application is a national phase filing under 35 U.S.C. § 371 of International Application No. PCT/US2013/066010, titled "Accurate and Interference-Free Multiplexed Quantitative Proteomics Using Mass Spectrometry," filed Oct. 22, 2013, which claims the benefit of U.S. provisional patent application No. 61/716,806 titled "Accurate and Interference-Free Multiplexed Quantitative Proteomics Using Mass Spectrometry," filed Oct. 22, 2012, both of which are incorporated herein by reference in their entirety.

GOVERNMENT SUPPORT

This invention was made with government support under GM026875, HG3456 and GM67945 awarded by National Institutes of Health. The government has certain rights in the invention.

BACKGROUND

Mass spectrometry (MS) is a technology that allows the precise determination of the mass of molecules. It is widely used in numerous applications in life- and other sciences and today it is considered to be one of the most relevant analytical platforms in the characterization of proteins and peptides, where it allows generating a holistic picture of many properties of almost all proteins—the proteome—in a cell or tissue. Attempts to globally study all proteins in a biological sample are usually described using the umbrella term proteomics.

There are a number of approaches to use MS to identify, characterize, or quantify proteins, but the most widely applied strategy is the so-called "bottom-up" approach where specific enzymes are used to cleave proteins at well-defined positions to generate peptides, which are then subjected to MS. MS generally only allows the analysis of molecules carrying a charge (i.e., ions) and therefore peptides, prior to being subjected to the mass spectrometer, are usually ionized using one out of several ionization techniques, such as electrospray ionization (ESI), matrix-assisted laser desorption/ionization (MALDI), or any other suitable technology.

A common way of processing peptides in the mass spectrometer is to first determine the mass—actually the mass-to-charge ratio (m/z)—of the intact peptide in an $MS^1$ experiment and then generating additional information regarding the structure of the peptide ion in an $MS^2$ experiment by fragmenting the peptide ions into smaller ions followed by the measurement of the m/z values of these so-called fragment ions. Usually, the collected information used in combination with protein sequence databases of the studied organisms is sufficient to obtain the amino acid sequence of the analyzed peptides, which allows one to infer information about the proteins of the studied sample.

When a proteomics experiment, which often analyzes 10,000 s of peptides in a single experiment, is performed to obtain quantitative information, the experiment most frequently results in relative quantitative data by comparing two or more specific samples. Peptides from each sample may be derivatized or labeled with certain stable isotopes (e.g. carbon-13 or nitrogen-15), so that after pooling the samples, an identical but differentially labeled pair of peptides can be distinguished in the mass spectrometer and the measured peptide ion intensity may be used to obtain accurate quantitative information about concentration differences of this peptide between the studied samples. One shortcoming of mass spectrometry-based proteomics experiments is that they require relatively long acquisition times on rather expensive mass spectrometers. Accordingly, there is considerable effort put into the development of methods that allow multiplexed quantitative experiments—the parallel quantitative comparison of several samples in just one experiment. The development of specially designed chemical tags, such as tandem mass tags (TMTs) and isobaric tags for relative and absolute quantitation (iTRAQ), has provided the ability to perform multiplexed quantitation of a plurality of samples simultaneously. Performing a multiplexed quantitation allows the relative quantities of particular proteins or peptides between samples to be determined. For example, multiplexed quantitation may be used to identify differences between two tissue samples, which may comprise thousands of unique proteins.

The chemical tags are included in reagents used to treat peptides as part of sample processing. A different tag may be used to label each separate sample. Each of the plurality of tags may be isobaric, meaning each of the types of tags has nominally the same mass and are therefore indistinguishable in an $MS^1$ spectrum. This is achieved by using different isotopes of the same elements in the creation of the tags. For example, a first tag may use a carbon-12 atom at a particular location of the molecule, whereas as second tag may use a carbon-13 atom—resulting in a weight difference of approximately one Dalton at that particular location. This purposeful selection of particular isotopes may be done at a plurality of locations for a plurality of elements. As a whole, each isotope of each tag is selected so that the different types of tags have the same total mass resulting in tagged precursor ions with nominally the same mass despite being labeled with a different type of tag. The different isotopes are strategically distributed within the tag molecule such that, when the tag is fragmented, the portion of the tag molecule that will become a low-mass reporter ion for each type of tag has a different weight. Thus, when the different types of tags are fragmented during the $MS^2$ analysis techniques, each type of tag will yield reporter ions with distinguishable mass-to-charge (m/z) ratios. The intensity of the reporter ion signal for a given tag is indicative of the amount of the tagged protein or peptide within the sample. Accordingly, multiple samples may be tagged with different tags and simultaneously analyzed to directly compare the difference in the quantity of particular proteins, peptides or molecules in each sample.

SUMMARY

Some embodiments are directed to a method of performing a mass spectrometry analysis. The method includes creating a mixture of a plurality of samples, wherein each of the plurality of samples comprises at least one type of precursor ion labeled with at least one type of chemical tag selected from a plurality of chemical tags, wherein each of the plurality of samples comprises a plurality of precursor ions of the at least one type of precursor ion; fragmenting the labeled precursor ions to form a plurality of ions comprising a first subset of ions and a second subset of ions, wherein each ion of the first subset of ions comprises at least a portion of the respective chemical tag but not the respective molecule; and each ion of the second subset of ions comprises at least a portion of the respective chemical tag and the respective molecule. The method further includes measuring an abundance of each type of ion of the second subset of ions; and determining a relative abundance of at least one type of precursor ion in each of the plurality of samples by analyzing the abundance of each type of ion of the second subset of ions.

Some embodiments are directed to at least one computer readable medium encoded with instructions that, when executed, perform a method. The method includes labeling at least one type of molecule of each of a plurality of samples with a respective chemical tag selected from a plurality of chemical tags, wherein each of the plurality of samples comprises a plurality of molecules; fragmenting each of the labeled molecules to create at least a first portion and a second portion, wherein the first portion has a lower mass than the second portion; measuring a relative abundance of each second portion; and determining a relative abundance of the at least one type of labeled molecules in each of the plurality of samples by correcting for isotopic variations in each of the labeled molecules.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 5A-E illustrate a more detailed comparison of quantification using TMT reporter ions versus $TMT^C$ ion clusters based on exemplary experimental data;

FIGS. 9A-E illustrate the quantification of multiple peptides from a single $MS^2$ spectrum according to some embodiments;

FIGS. 14A-F illustrate an exemplary large-scale evaluation of complementary ion quantification;

FIGS. 15A-C illustrate methods of improving efficiency of complementary ion based quantification according to some embodiments.

DETAILED DESCRIPTION

The inventors have recognized and appreciated that when analyzing complex mixtures, peptides selected for fragmentation are typically contaminated by co-eluting ions of lower abundance. Reporter ions may therefore originate from both target and interfering ions, which cause a distortion of the quantification. In this case, determining the quantity of the tagged target peptide is difficult due to the reporter ions of the target peptides being indistinguishable from the reporter ions of interfering ions. Accordingly, any interfering ion that was co-isolated with the target peptide destroyed the ability to accurately determine the relative quantity of the target peptide in the sample.

Figure 1A:
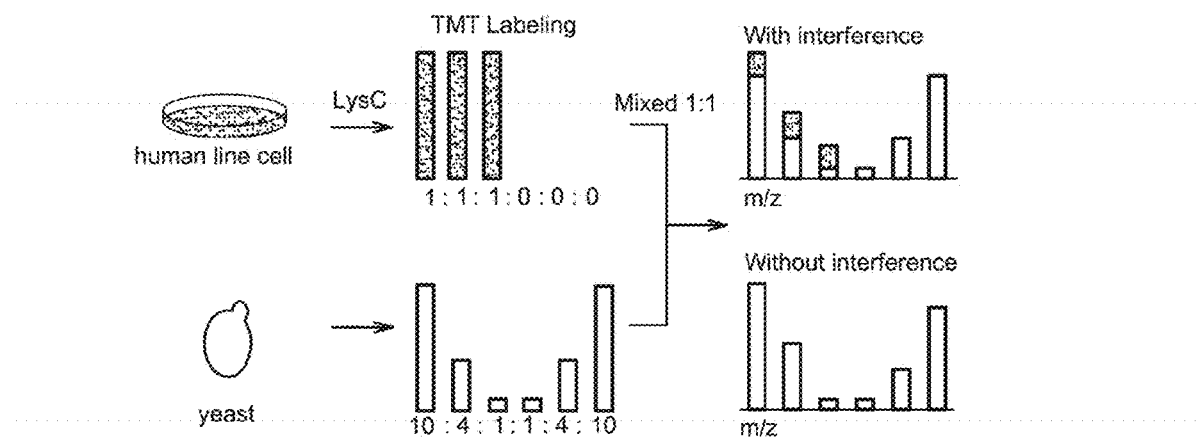
FIG. 1A illustrates an example of interference from ions other than reporter ions.

FIG. 1 illustrates this interference problem. FIG. 1A shows a complex mixture of LysC digested TMT-labeled yeast peptides mixed in a one-to-one ratio with a complex mixture of LysC digested TMT-labeled human peptides. The yeast peptides, for the purposes of this illustrative example, are considered the target and the human peptides generate the interfering ions. Yeast peptides were labeled with each of the six TMT reagents (126-131) and mixed in a ratio of 10:4:1:1:4:10 (126:127:128:129:130:131). Human peptides are labeled only with the first three TMT reagents 126-128. These were mixed in a ratio of 1:1:1 and pooled with the yeast peptides. If there was no interference from the human peptides, reporter ions in yeast peptide ion $MS^2$ spectra would perfectly match the original ratio of the target sample, i.e. 10:4:1:1:4:10. This ideal spectrum is illustrated by the reporter ion intensity distribution shown on the bottom right of FIG. 1A. However, with interference from the human peptide ions yeast peptide reporter ion intensity ratios are distorted and render the quantitative data inaccurate, as illustrated by the MS spectrum in the top right of FIG. 1A. Due to contributions in the first three TMT channels by human peptide ions, the intensity of the peaks associated with the m/z value of the first three tags are not accurate. This interference destroys the ability to accurately determine the relative ratios of each tag used in the yeast sample.

Figure 1B:
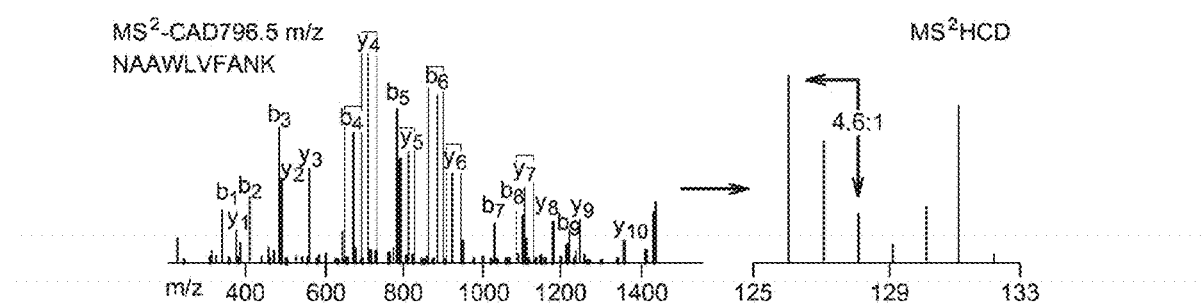
FIG. 1B illustrates an experimental example of interference from ions other than reporter ions.

This interference problem is also illustrated in the spectra of FIG. 1B based on experimental data. The peptide NAAWLVFANK was labeled with TMT labels with a ratio of 10:4:1:1:4:!0 and interrogated in back-to-back scans using $MS^2$ scans that fragmented the $MS^1$ precursors. The fragmentation could be done, for example, using CID-NCE35 or HCD-NCE45. The spectrum on the left represents the $MS^2$ product ion spectrum of the above described sample generated through fragmenting a yeast peptide ion using collision induced dissociation (CID). The spectrum on the right of FIG. 1B represents a portion of the $MS^2$ product ion spectrum showing only the m/z value range from 125-133, which is the range encompassing the m/z values of the six different reporter ions of the six different types of TMT tags used. As discussed above, the intensity ratio of the first to third TMT channel should be 10:1 in the absence of interference from the human peptides. In this particular experiment, the ratio is 4.6:1, shifted to a lower ratio than expected by a factor of more than two. This dramatic inaccuracy of the relative quantitation measurement illustrates the need to find a solution to this interference problem caused by co-isolated precursors.

The inventors have recognized and appreciated that, though the isobaric chemical tags may be designed to quantify the relative abundance of molecules in a complex sample using the low-mass reporter ions, the problem of co-isolated peptides may be remedied by measuring the intensity of each high-mass complementary ion associated with each labeled peptide, instead of quantifying the amount of each differentially labeled peptide based on reporter ion intensities. The fragmentation mechanism for labeled peptides is such that, concurrent with the formation of the low-mass reporter ions, high-mass complementary ions are formed as well (see top of FIG. 2A). Asterisks in FIG. 2A indicate sites of heavy isotopes ($^{13}C$ or $^{15}N$). TMT reporter ions and $TMT^C$ ions are formed through bond cleavage at the indicated positions. The m/z of both reporter ions and $TMT^C$ ions are channel specific. The high-mass complementary ions ($TMT^C$ ions) carry most, of the mass-balancing group of the TMT tag. Accordingly, information regarding the relative abundances of the labeled samples may be obtained by measuring the relative abundances of the complementary ions.

The inventors have recognized and appreciated that, in contrast to the use of low m/z reporter ions, the m/z values of these complementary ions (in the case of TMT tags, referred to as $TMT^C$ ions) are precursor specific. The risk that a complementary ion of a target molecule will have a spectral envelope at exactly the same location in the $MS^2$ spectrum as a complementary ion for an interfering molecule is very low. Accordingly, interfering peptides have a much smaller effect on the measurement of the $TMT^C$ ion of interest. Furthermore, should other peptides interfere with the $TMT^C$ ion cluster, it is unlikely that the interfering peptides would result in an ion cluster which could be generated only by the peptide of interest. By comparing the observed ion-clusters with theoretical ion-clusters, peptides with inaccurate quantitation can be filtered out and inaccurate quantification further reduced. Using complementary ions to quantify relative abundances may be implemented on a wide range of mass spectrometers—e.g. quadrupole time-of-flight (Q-TOF), quadrupole Orbitrap instruments (QExactive), hybrid quadrupole ion trap Orbitrap mass spectrometers, and Fourier-transform ion cyclotron resonance analyzers (FT-ICRs). This complementary ion technique not only provides higher accuracy in the quantification of labeled molecules, but also maintains the parallelization of the multiplexed tags; hence, it has the potential to multiply the number of distinct peptides that can be quantified in a given time frame.

The inventors have recognized and appreciated that, unlike some techniques that require analyzing an $MS^3$ spectrum, or that utilize a proton transfer reaction, embodiments of the present application do not require any additional gas-phase purification steps and may therefore result in higher sensitivity and faster data acquisition. The inventors have recognized and appreciated that the high mass accuracy and resolution mass-spectrometers allow the quantification of peptides using $TMT^C$ ions. As an alternative to using the low m/z reporter ions in the $MS^2$ spectrum, embodiments quantify differences between the various samples based on $TMT^C$ ions. The complementary ions carry the equivalent quantitative information about the relative levels of the differentially labeled peptides as the low m/z reporter ions, but are minimally affected by interfering peptide ions. While the low-mass m/z reporter ions are isomeric and therefore undistinguishable regarding their origin from target or contaminating ions, the resulting $TMT^C$ ions from target and contaminating ions are expected to show differences in their m/z values, which makes them distinguishable using modern mass spectrometry.

Figure 2A:
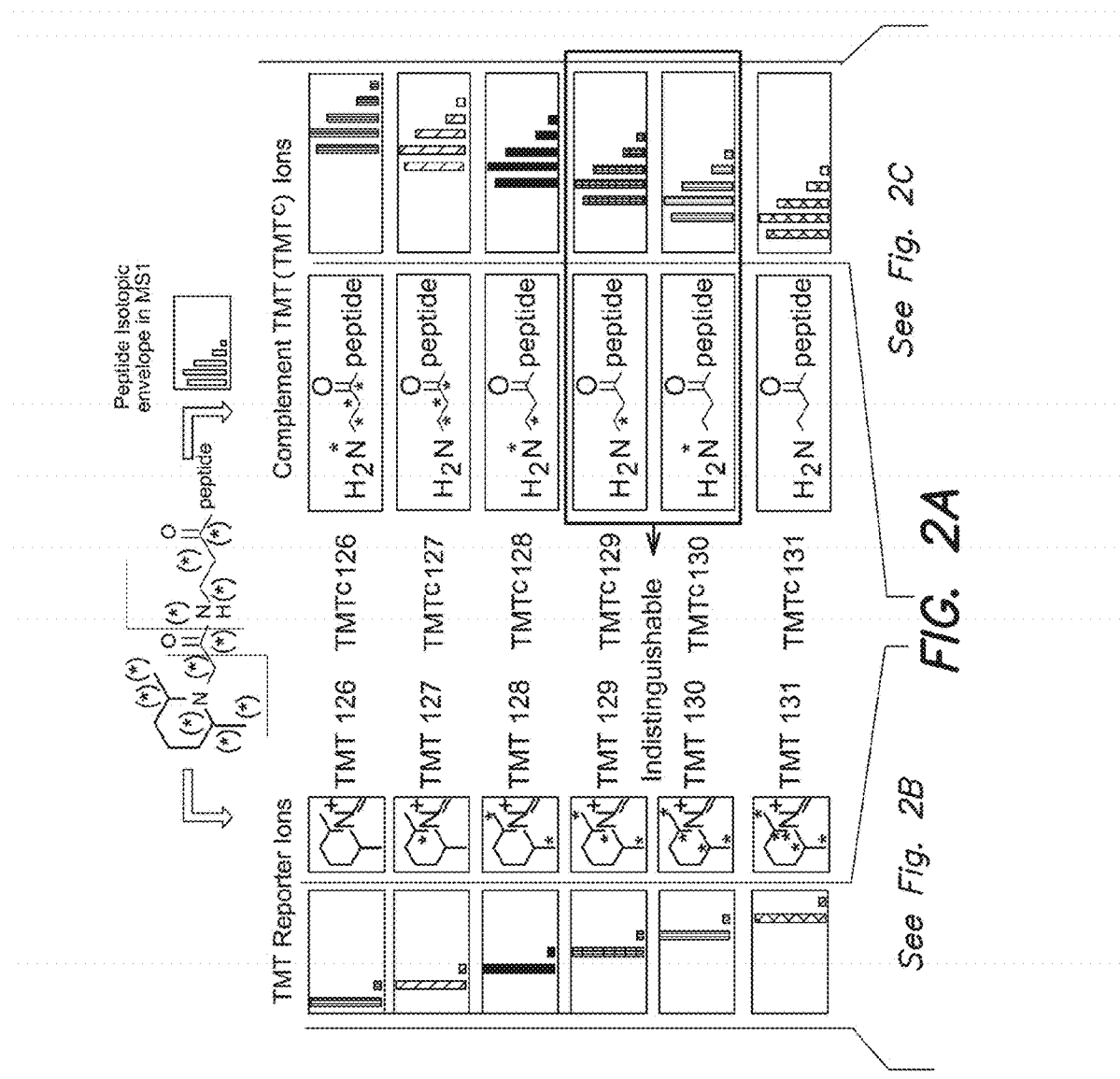
FIG. 2A illustrates a peptide isotopic envelope, reporter ion spectrums and complementary ion spectrums that result from fragmenting TMT-labeled peptides.

The inventors have recognized and appreciated that, though the observed quantities of the complementary ions do not directly give relative abundance information, this information may be extracted from the data based on a data analysis that uses details about the tags and the labeled molecule. One of the reasons that the relative abundance is not directly observable in the measured quantities is that there is natural isotope variation within the peptide being measured. For example, carbon-12 comprises ~99% of the naturally occurring carbon in the world, but carbon-13 makes a 1% contribution. A target peptide may be twelve amino acids long and have a mass of approximately 1200 Daltons (Da). Based on the natural abundance of each isotope of carbon, the mass of peptides with the same twelve amino acids may vary by a few Daltons. For example, the MS spectrum may result in a spectral envelope showing peaks at 1200 Da, 1201 Da, 1202 Da, and 1203 Da, purely from the relative abundance of isotopes as they appear in nature. FIG. 2A illustrates, in the upper-right, a peptide isotopic envelope, which represent the same peptide spectrum with peaks separated by one Dalton, representing the mass difference between e.g. carbon-12 and carbon-13. The leftmost peak represents the abundance of the peptide consisting of all carbon-12 atoms and is called the monoisotopic peak. The neighboring peak represents the abundance of the peptide where a single one of the many carbon atoms is a single carbon-13 (or single N-15). Similarly, the additional peaks, separated from each previous peak by ~one Dalton, represent peptides with additional carbon-13 atoms.

Another reason that the relative abundance is not directly observable in the measured quantities is that, despite the fact that the chemical tags are engineered to have particular isotope configurations, isotopic impurities cause variations in not only the total mass of each type of isobaric tag, but also variations in the reporter ion portion and the $TMT^C$ ions. For example, the left side of FIG. 2A illustrates the reporter ion spectrum for each of the six TMT tags. Each spectrum shows small secondary peaks one Dalton heavier or lighter than the main peak caused by a heavy isotope being inadvertently used in a location where a light isotope was designed to be or vice versa. Accordingly, FIG. 2B illustrates a reporter ion spectrum resulting from tagging a peptide with an equal number of each type of chemical tag. The different fill patterns of the reporter ion spectrum represent which type of tag was the source of the particular ion in each peak. For example, a TMT-126 tag is the sole contribution to the peak at 126 Da, but contributes a small amount to the peak at 127 Da. The other types of TMT tags contribute in a similar manner to their respective peaks. Impurities in the TMT-131 tag result in a peak at 132 Da where no other tag contributes.

The right side of FIG. 2A illustrates the isotopic envelope for each $TMT^C$ ion. The envelope may not be identical to the envelope for the peptide itself because there may be additional contributions from impurities in the portion of the chemical tag that stays attached to the peptide after fragmentation. Note that there may be a portion of each isobaric tag that neither stays attached to the reporter ion nor the $TMT^C$ ion after fragmentation. This portion may result in two $TMT^C$ ions (e.g., $TMT^C$-129 and $TMT^C$-130, which are the complementary ions associated with the TMT-129 tag and the TMT-130 tag, respectively) with the same mass. These two $TMT^C$ ions may therefore be indistinguishable and should not be used simultaneously for tagging different samples. The convolution of these two complementary ions is a result of how these particular chemical tags were engineered. Some embodiments may use a set of chemical tags that have no such distinguishability problem.

Figure 2C:
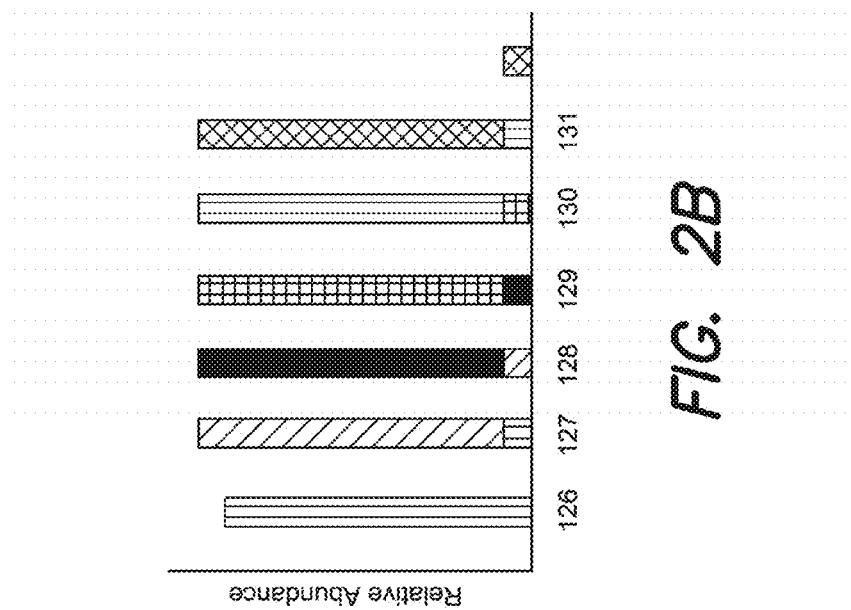
FIG. 2C illustrates a complementary ion spectrum for a peptide that is labeled with an equal ratio of each type of chemical tag.
Figure 2B:
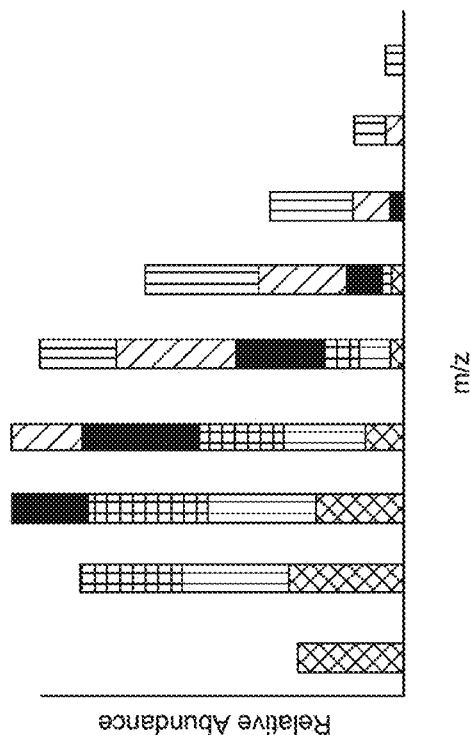
FIG. 2B illustrates a reporter ion spectrum for a peptide that is labeled with an equal ratio of each type of chemical tag.

FIG. 2C illustrates the $TMT^C$ ion spectrum that results from tagging a peptide with an equal number of each type of chemical tag. Just as in the reporter ion spectrum in FIG. 2B, the different fill patterns of the $TMT^C$ ion spectrum represent which type of tag was the source of the particular ion in each peak. However, the $TMT^C$ ion spectrum is more complicated than the TMT reporter ion spectrum due to each $TMT^C$ ion contributing to more than two peaks. In the example shown, each $TMT^C$ ion contributes to the overall isotopic envelope, which spans a region of 5 m/z. Embodiments are not limited to 5 m/z. $TMT^C$ ions may contribute to any number of peaks, either more or less, depending on the size of the tags and the size of the peptide. Neglecting isotopic impurities the lowest mass peak of the $TMT^C$ ion spectrum results solely from the $TMT^C$-131 ion. The next peak receives contributions from the $TMT^J$-131 ions and the $TMT^J$-129 and $TMT^J$-130 ions (which both contribute due to their indistinguishability). Each of the other peaks receives contributions from their respective $TMT^C$ ions. The $TMT^C$ ion spectrum has nine peaks, which originate from the five original peaks of the peptide envelope being convoluted with the five tags with distinguishable $TMT^C$ ions. Reading the relative abundance of each peak does not directly give the abundance of each type of tagged peptide in the multiplexed samples. Instead, this information is buried within the $TMT^C$ ion spectrum and must be extracted. Due to the overlap of the high m/z $TMT^C$ ion envelopes of each TMT channel, peptides are quantified by deconvolving the $TMT^C$ cluster using ion intensity distributions of the isotopic envelope of the precursor peptide, which may be obtained theoretically or experimentally.

To determine the relative abundance of each type of tagged peptide from the $TMT^C$ ion spectrum, both the isotopic variation in the target molecule and the isotopic impurities of the tags must be taken into account. The details of the impurities may differ depending on how, when, and where the chemical tags are manufactured. Each batch of the chemical tags that is manufactured may differ from the previous batch. The manufacturer of the chemical tags may provide the details of the impurities for a particular batch to the user of the MS device. Alternatively, the user of the MS device may determine the impurity details by performing one or more experiments using the chemical tags. In some embodiments, the chemical tags may be designed such that the impurities of the tags are negligible and the analysis may omit accounting for this these impurities.

Figure 3A:
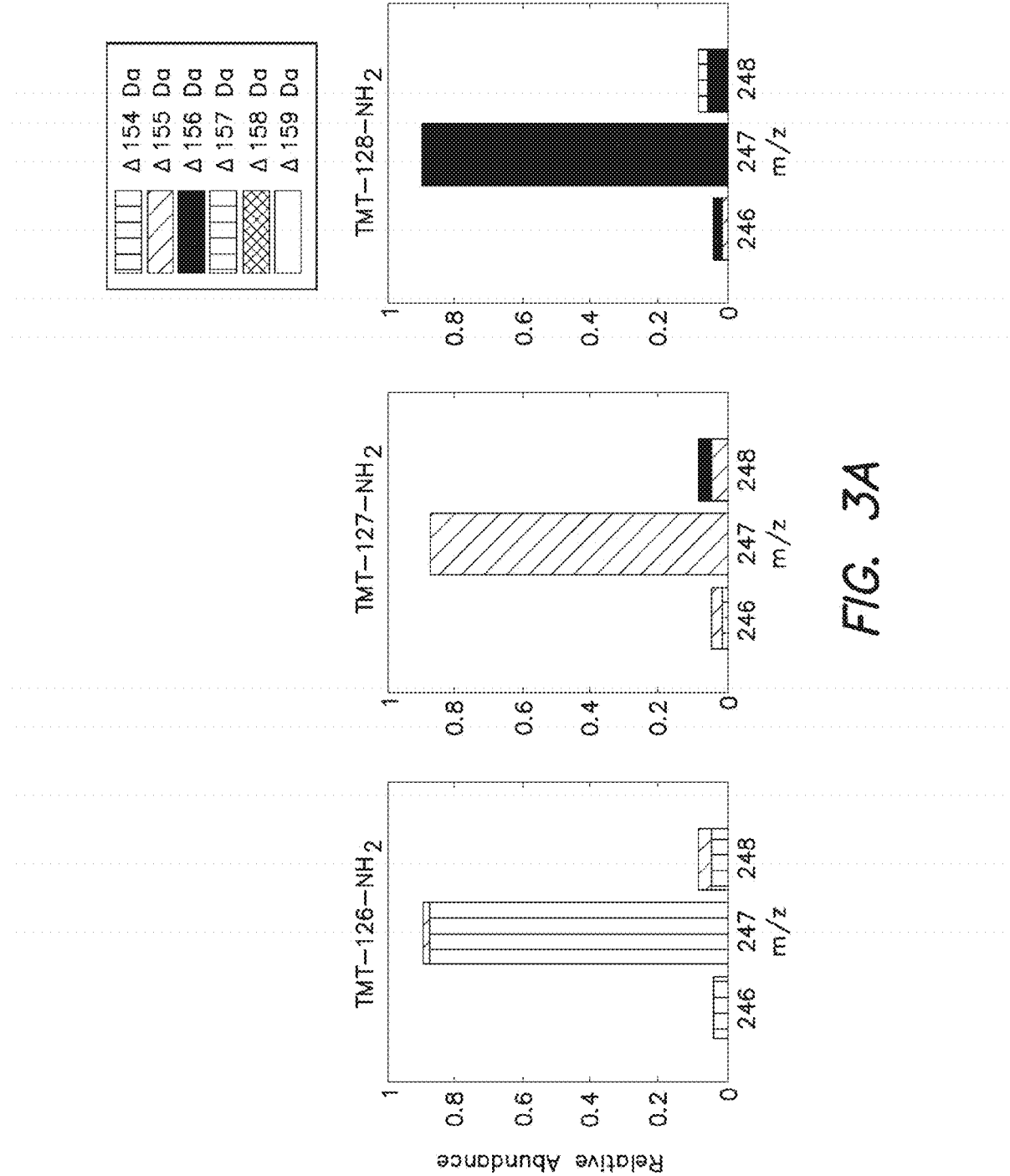
FIGS. 3A-B illustrate impurity information for an exemplary embodiment of six types of TMT tags.
Figure 3B:
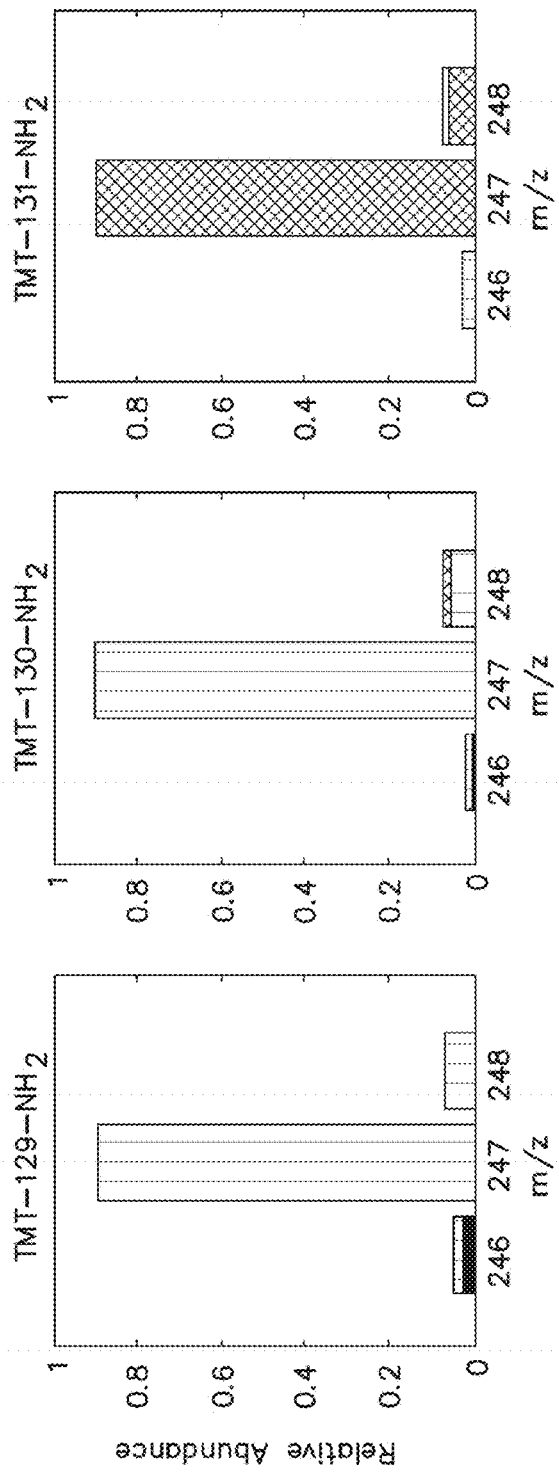

FIGS. 3A-B illustrate the results of one such example experiment used to determine impurity information for the six types of TMT tags. The experiment determines the isotopic composition of each of the TMT tags. In the experiment, each of the tag types is separately reacted with ammonium bicarbonate, and the resulting $NH_2$-TMT isotopic envelopes are measured using MS on an Orbitrap Elite mass spectrometer. The target m/z of the entire $NH_2$-TMT ion is 247 Da. The spectral envelopes in FIGS. 3A-B illustrate the main peak for each of the six types of $NH_2$-TMT ions at 247 Da. An additional peak on either side of the main peak results from isotopic impurities that cause the entire $NH_2$-TMT ion to have a mass one Dalton more or less than the target mass. The relative populations of each peak provide information about the different masses of the $NH_2$-TMT ion as a whole, but provide no information about where the impurities are located within the molecule. This information may be inferred by fragmenting each individual peak of each spectral envelope and measuring the $MS^2$ spectrum. The $MS^2$ spectrum provides information about the mass of the portion of the tag that stays attached to the $NH_2$ molecule. Each of the six types of tags is represented by a different type of shading, and its contribution to each of the peaks in each of the isotopic envelopes is illustrated in FIGS. 3A-B. For example, the central peak at 247 Da for the TMT-128-$NH_2$ envelope originates solely from a chemical tag that lost 156 Da upon fragmentation. The peak at 248 Da (representing a $NH_2$-TMT ion with one additional mass overall), on the other hand, receives contributions from the chemical tag that lost 156 Da and a chemical tag that lost 157 Da upon fragmentation.

The impurity information obtained by the above experiment and illustrated in the spectral envelopes of FIGS. 3A-B may be written in matrix form. Accordingly, each of the six tags may be associated with an "impurity matrix," $I_{TMT}$ which, for the batch of tags used in the above experiment, are:

$$I_{126} = \begin{bmatrix} 0.032 & 0.875 & 0.047 \\ 0.000 & 0.014 & 0.032 \\ 0.000 & 0.000 & 0.000 \\ 0.000 & 0.000 & 0.000 \\ 0.000 & 0.000 & 0.000 \\ 0.000 & 0.000 & 0.000 \end{bmatrix} I_{127} = \begin{bmatrix} 0.004 & 0.000 & 0.000 \\ 0.036 & 0.880 & 0.040 \\ 0.000 & 0.004 & 0.036 \\ 0.000 & 0.000 & 0.000 \\ 0.000 & 0.000 & 0.000 \\ 0.000 & 0.000 & 0.000 \end{bmatrix}$$

$$I_{128} = \begin{bmatrix} 0.000 & 0.000 & 0.000 \\ 0.010 & 0.000 & 0.000 \\ 0.018 & 0.896 & 0.051 \\ 0.000 & 0.000 & 0.026 \\ 0.000 & 0.000 & 0.000 \\ 0.000 & 0.000 & 0.000 \end{bmatrix} I_{129} = \begin{bmatrix} 0.000 & 0.000 & 0.000 \\ 0.000 & 0.000 & 0.000 \\ 0.029 & 0.000 & 0.000 \\ 0.021 & 0.900 & 0.073 \\ 0.000 & 0.000 & 0.000 \\ 0.000 & 0.000 & 0.000 \end{bmatrix}$$

$$I_{130} = \begin{bmatrix} 0.000 & 0.000 & 0.000 \\ 0.000 & 0.000 & 0.000 \\ 0.001 & 0.000 & 0.000 \\ 0.021 & 0.906 & 0.065 \\ 0.000 & 0.000 & 0.008 \\ 0.000 & 0.000 & 0.000 \end{bmatrix} I_{131} = \begin{bmatrix} 0.000 & 0.000 & 0.000 \\ 0.000 & 0.000 & 0.000 \\ 0.000 & 0.000 & 0.000 \\ 0.026 & 0.000 & 0.000 \\ 0.000 & 0.900 & 0.062 \\ 0.000 & 0.000 & 0.012 \end{bmatrix}.$$

The columns of the impurity matrices represent how impurities in the tags affect the mass of the entire chemical tag before fragmentation, i.e. the columns define the position in the TMT-$NH_2$ precursor isotopic envelope (~246, 247, 248 Da left to right). For example, the central column reflects the proportion of the tags in the batch that have an actual mass equal to the target mass of 247 Da. The other two columns represent a shift of one Dalton up/down in mass. The matrices are cut-off at a one Dalton difference, because ions showing a higher mass difference are expected to be of such low intensity that they would not significantly contribute to changes in the overall distribution of the $TMT^C$ ion envelope. However, one of ordinary skill in the art would recognize that in embodiments where larger mass shifts are likely, the impurity matrices may be expanded to include more columns. Also, more rows may be added if a set of chemical tags with more than six different tag types is used.

The rows of the impurity matrices represent the six different mass decrements (Δm) that result from fragmentation in the MS$^2$ experiment, i.e. the mass difference between this precursor ion and its resulting TMT$^C$ ion after fragmentation (~154 Da to ~159 Da, top to bottom). For example, the topmost row represents tags that lost ~154 Da of mass upon fragmentation. Each row after the first represents a tag that, in one Dalton increments, lose more mass upon fragmentation, continuing to the bottommost row, which represents the tag that loses 159 Da upon fragmentation. The six different mass decrements arise from 5 different TMT channels (126 to 131, without 129 as there is no Δm between the TMT-129 and TMT-130 is, as described above) and an additional ion at ~132 Da, which is the result of an isotopic impurity in the TMT-131 tag.

For each of the types of tag, an "isotopic impurity vector" $t_{126} \ldots t_{131}$ may be defined by summing the rows of the respective matrices $I_{126} \ldots I_{131}$. For example, the isotopic impurity vector $t_{126}$=[0.032 0.889 0.079], where the numbers represent the relative abundance, regardless of fragmentation pattern, of the TMT-NH2 ions with ~246, 247 and 248 Da respectively. In other words, the isotopic impurity vectors represent the data that was obtained in the above experiment to characterize the chemical tag impurities after the MS 1 stage, prior to fragmenting each peak to determine the MS$^2$ spectrum.

Figure 4:
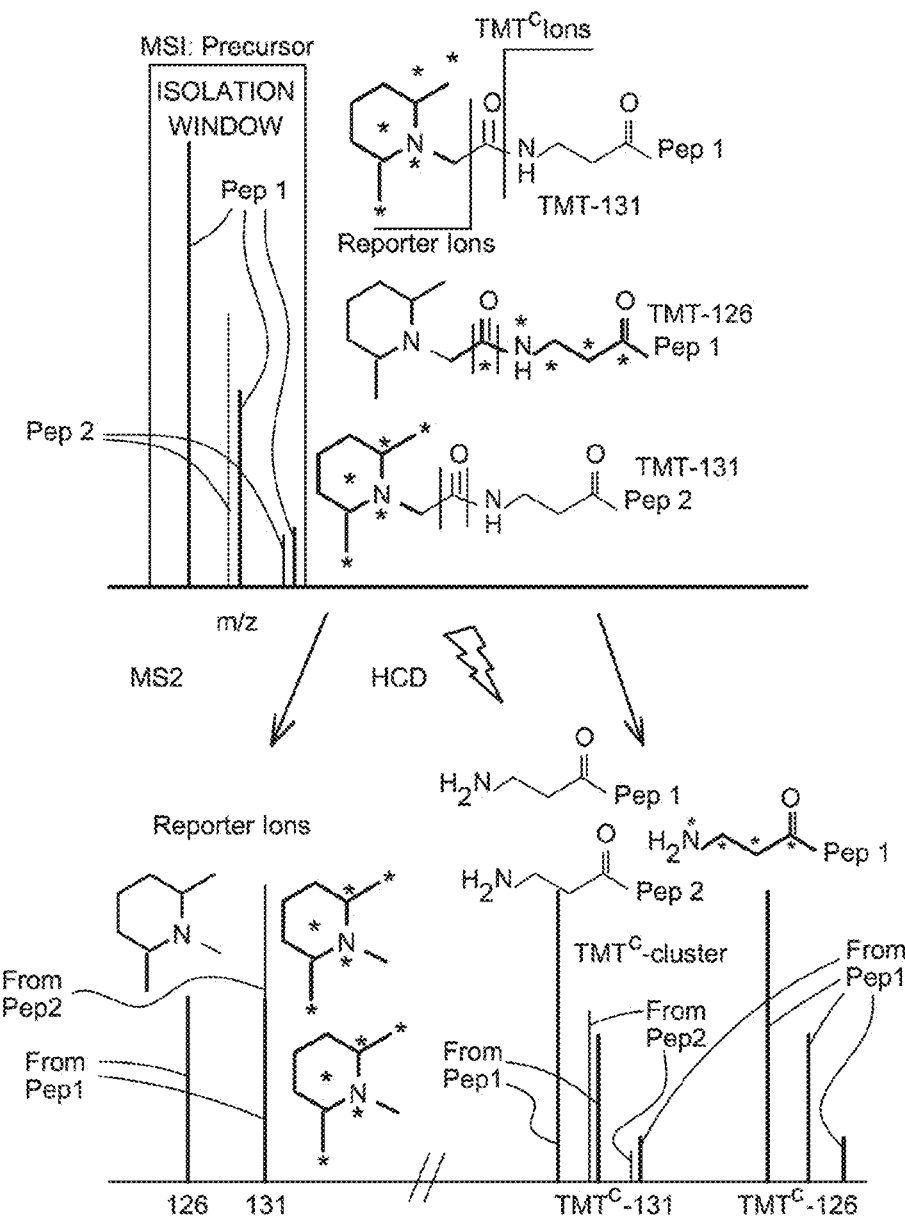
FIG. 4 illustrates the general principle by which complementary ion clusters may be used to quantify the relative abundance of each of the labeled samples in an exemplary multiplexed $MS^2$ experiment.

Based on the above description of how isotopic impurities affect the spectral envelopes of the complementary ions, it should be clear how the complementary ions result in a cluster of peaks which may overlap. FIG. 4 illustrates the general principle by which these complementary ion clusters may be used to quantify the relative abundance of each of the labeled samples in a multiplexed MS$^2$ experiment. The top of FIG. 4 illustrates a first sample of a target peptide (Pep1) labeled with a TMT-131 tag and a second sample of the target peptide labeled with a TMT-126 tag. Both forms are mixed in a ratio of 1:1. The MS$^1$ precursors are isolated in the MS device using an isolation window, as is known in the art. However, an interfering peptide (Pep2) tagged with TMT-131 also falls within the isolation window and co-elutes with the target peptide. When the isolated peptides are fragmented, using, e.g., HCD, the two tag types fragment at the two positions indicated by the dashed lines in the top of FIG. 4. The leftmost portions are the low-mass reporter ions, which are used in the prior art for determining the relative abundance of each sample. The right most portion are the high-mass complementary ions, which include the peptide and at least a portion (i.e., the mass-balancing portion) of the TMT tag. The asterisks along the ion indicate locations where carbon-13 isotopes are intentionally used instead of carbon-12 isotopes or nitrogen-15 is intentionally used instead of nitrogen-14.

The bottom of FIG. 4 illustrates the resulting MS$^2$ spectrum and clearly shows the aforementioned problems that arise from basing a relative abundance measurement on the reporter ion peaks at 126 Th and 131 Th. The two target peptide samples were mixed in a 1:1 ratio, but the interfering peptide, which was also tagged with the TMT-131 tag, increases the TMT-131 contribution. Because the signal from the interfering peptide is indistinguishable from the signal from the target peptide, it is not possible to use the relative abundance of the TMT-126 and TMT-131 reporter ions to accurately quantify the relative abundance of each sample of the target peptide. However, as described above, the complementary ion clusters from the target peptide are distinguishable from the complementary ion clusters from the interfering peptide. Accordingly, the measurement of the TMT$^C$ ion clusters may be used to accurately obtain the relative abundance of the target peptide from each sample without interference from the interfering peptides. Thus, the TMT$^C$ ion clusters comprises accurate quantitative information which may be used to quantify multiple peptides in a single MS$^2$ spectrum. In the example shown in the FIG. 4, it can be seen, for example, that peptide 1 and peptide 2 can each be quantified because the TMT$^C$ ions for each peptide do not overlap.

Figure 5A:
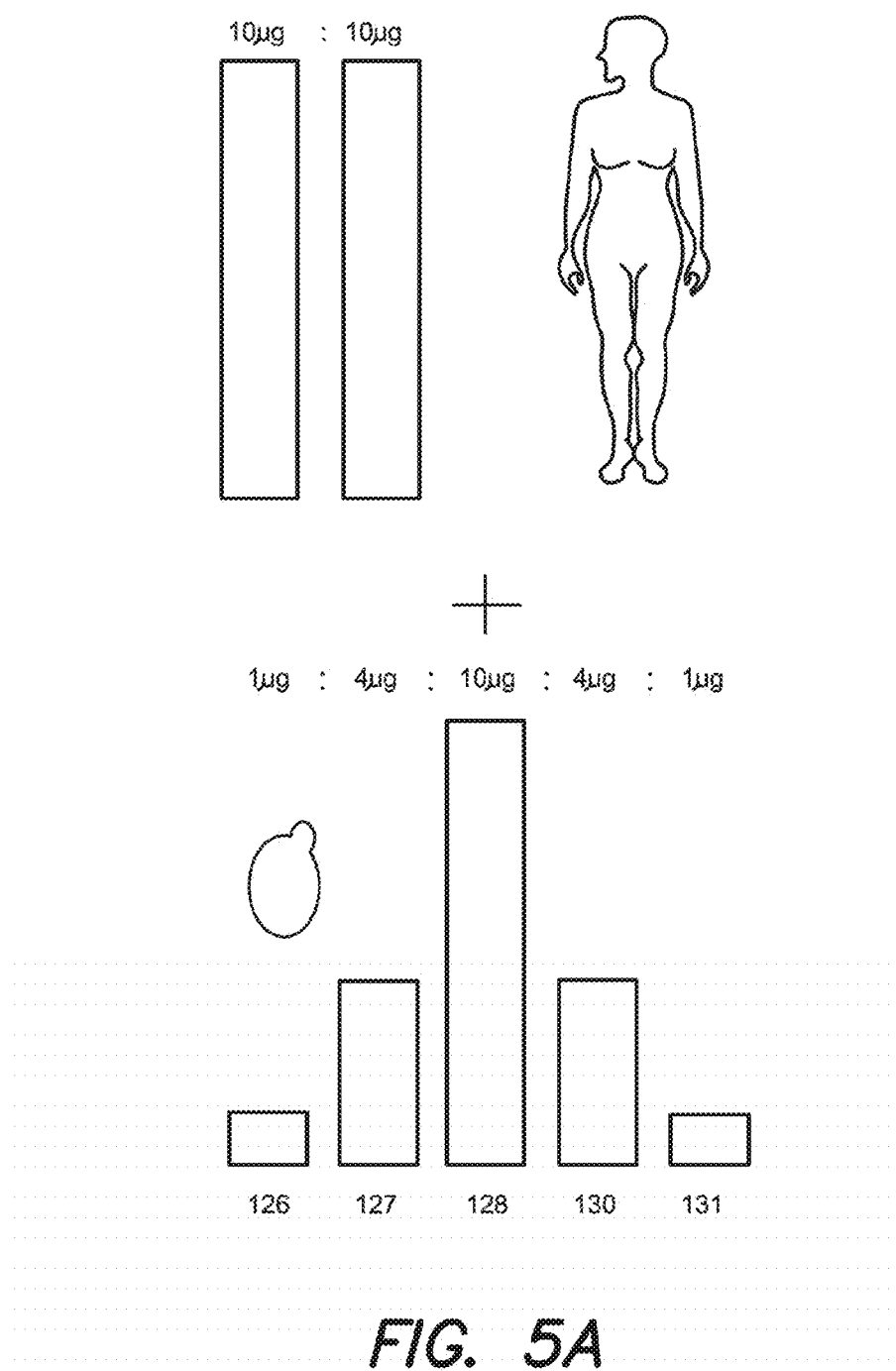

FIGS. 5A-E illustrate a more detailed comparison of quantification using TMT reporter ions versus TMT$^C$ ion clusters based on experimental data. The preparation of the samples are illustrated in FIG. 5A. Two samples of known mixing ratios and known quantities of interfering peptides are used to investigate the accuracy of the quantification and the effects of interference. The sample comprises 1 μg:4 μg:10 μg:4 μg:1 μg of Lys-C-digested yeast peptides labeled with TMT in the channels 126, 127, 128, 130, and 131, respectively. Interference is simulated by adding a mixture of 10 μg:10 μg human Lys-C-digested peptides labeled with TMT-126 and TMT-127, respectively. The TMT-129 channel is omitted because, as previously described, the TMT$^C$-129 and TMT$^C$-130 ions are indistinguishable.

Figure 5D:
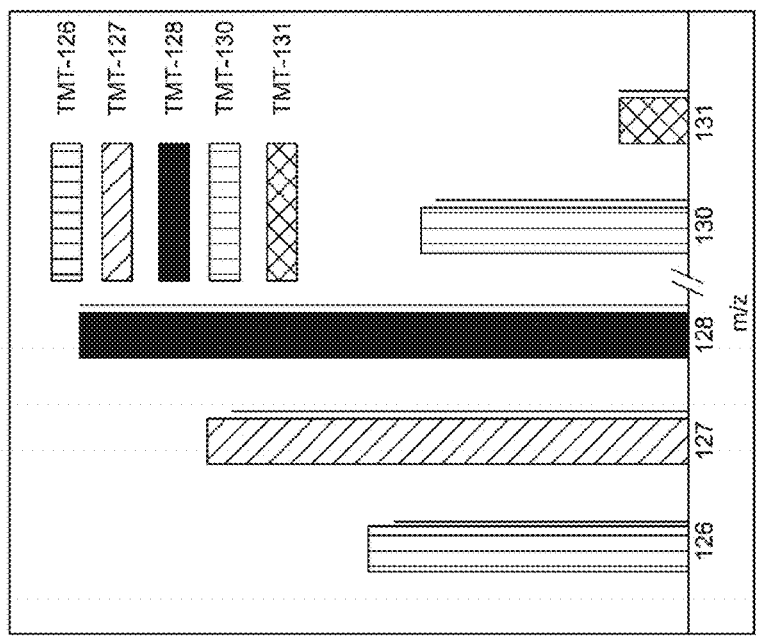
Figure 5D:
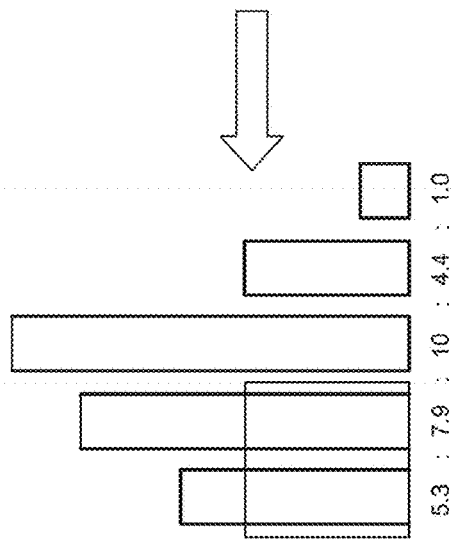
Figure 5E:
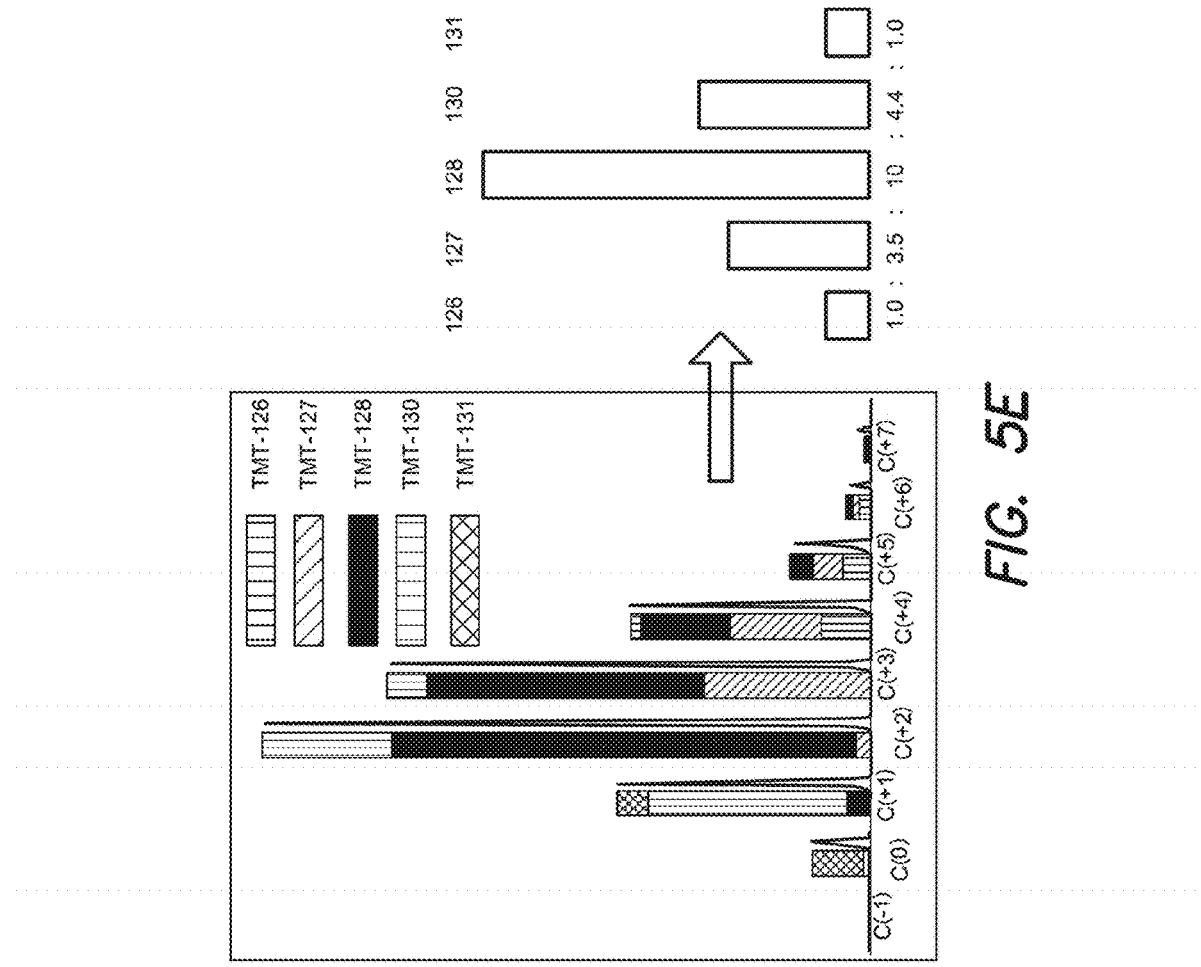

FIG. 5C illustrates the MS$^1$ precursor spectrum region within the set isolation window. Many small peaks resulting from interfering ions are visible within the isolation width used to capture the larger target peaks for MS$^2$ analysis. Accordingly, when the precursor is fragmented using, e.g., HCD, both target and interfering peptides are fragmented and contribute to the MS$^2$ spectrum shown in FIG. 5B. FIG. 5B illustrates the full MS$^2$ spectrum of yeast peptide AIELFTK labeled with the five TMT tags taken from the human-yeast interference sample described in FIG. 5A. The MS$^2$ spectrum was taken on a QExactive with 35 k nominal resolution setting and ±2 m/z isolation windows. The MS$^2$ spectrum has two areas of interest: the low-mass range showing the relative abundance of the reporter ions for each of the five tags (located in the range of 126-131 m/z); and the high-mass range showing the relative abundance of the TMT$^C$ clusters (located at about 1125 m/z). A zoomed in illustration of both of these m/z regions is illustrated in FIG. 5D and FIG. 5E, respectively. The relative abundance of each of the target samples, as determined using the low-mass reporter ions, is also shown in FIG. 5D. The ratios of each of the samples should match the original ratios shown in FIG. 5A, namely: 1:4:10:4:1. However, while reporter ion quantification is accurate in the interference free channels (128 to 131), the interference from the human peptide distorts the ratios between the channels and destroys the ability to accurately determine the relative abundance of the TMT-126 and TMT-127 labeled samples. The ratios obtained after correcting for isotopic impurities is shown in the left side of FIG. 5D. In a real biological sample, where the mixing ratios would be unknown, the user of the MS device would be unable to distinguish which fraction of the reporter ions originated from the peptide of interest and which fraction originated from interfering peptides.

Embodiments may use the high-mass TMT$^C$ ion clusters to obtain the relative abundance of the samples with reduced interference from interfering ions. FIG. 5E illustrates the detected TMT$^C$ ion cluster associated with the target peptide. Unlike the reporter ions, the position of this ion cluster is dependent on the exact mass and charge state of the precursor ion. Nine channels are illustrated, labeled c(−1) through c(+7). The peak at c(0) is the peak derived from the TMT-131 labeled pseudo-monoisotopic precursor and the other peaks are labeled relative to this position. Each peak is a result of one or more TMT-labeled peptides of different types. The shadings of each portion of each bar represent which type of TMT tag was labeling the peptide resulting in that respective portion. Using a method described in more detail below, the aforementioned impurity matrices may be used to determine the actual relative abundances of each of the labeled samples, as illustrated in the right-hand side of FIG. 5E. The ratio distortion measured for the reporter ion intensities of peptides labeled with TMT-reagents 126 and 127 is not present when quantitation is based on the intensities of high-mass complementary ions, resulting in interference-free quantitation.

Figure 6:
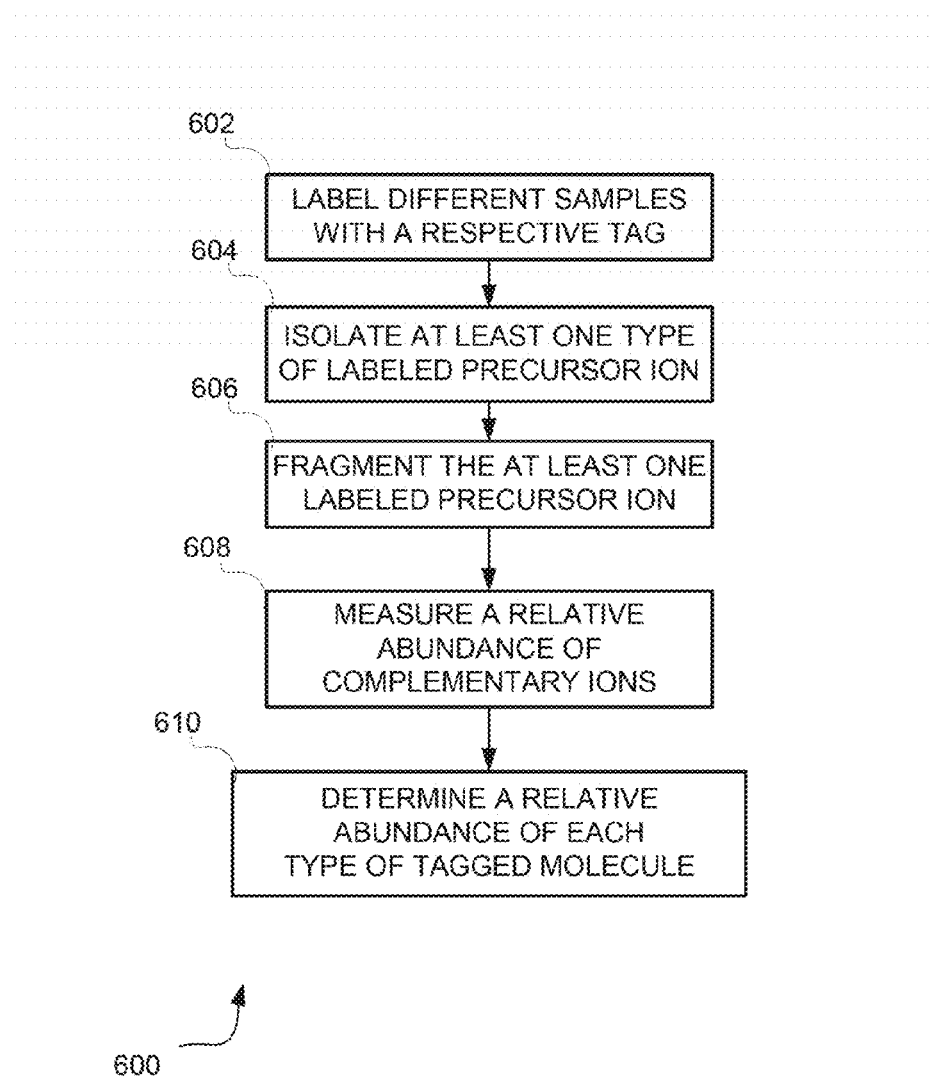
FIG. 6 is a flowchart of a method of performing mass spectrometry according to some embodiments.

FIG. 6 illustrates an exemplary method of performing mass spectrometry in accordance with some embodiments. At act 602, the different samples that are being analyzed are labeled with a respective chemical tag. Any suitable chemical tag may be used. The tags may be isobaric such that, prior to fragmentation, the different types have the same mass. For example, the isobaric tags may be tandem mass tags (TMTs) or isobaric tags for relative and absolute quantitation (iTRAQ), which are two commercially available types of reagents, though embodiments are not so limited.

At act 604, at least one type of labeled precursor ion is isolated. This may be done in any suitable way and depends on the specifics of the MS device. For example, an isolation window may be created using a waveform generator that controls an ion trap of the MS device. However, embodiments are not limited to any particular way of isolating precursor ions.

At act 606, the at least one labeled precursor ion isolated in the MS device is fragmented. This may be achieved in any suitable way, such as HCD. The fragmentation occurs when a portion of each chemical tag breaks off from the rest of the labeled ion. The portion of the chemical tag that breaks off may be known as the reporter ion, as this is the portion of the chemical tag that was designed to be measured in accordance with the prior art.

The reporter ions from the various tags form a first subset of molecules that are generated via fragmentation. A second subset of molecules, representing a portion of the original labeled molecule with a higher mass than the reporter ion, is also generated by the fragmentation act. The second subset of molecules comprises a portion of the chemical tag that remains attached to the labeled molecule from each sample and the molecule itself and potentially other non-fragmented or fragmented tags. The second subset of molecules may be the complementary ions, e.g., $TMT^C$ ions in the case of TMT tags. However, embodiments are not so limited.

At act 608, the relative abundance of each type of ion of the second subset of molecules is measured. In some embodiments, this measurement is an $MS^2$ measurement. The details of how the measurement is performed depends on the type of MS device used and is known in the art.

At act 610, the relative abundance of each type of tagged molecule is determined. An exemplary embodiment of act 610 is described below in connection with FIGS. 7A-B and FIG. 8.

A method of determining the relative abundance of the labeled samples is described in connection with FIGS. 7A-B, which illustrate various relative intensities used in the analysis, and FIG. 8, which is a flow chart illustrating an exemplary method according to one embodiment. The embodiment of the method described herein uses the aforementioned impurity matrices for each type of tag. These impurity matrices may be obtained in any suitable way. For example, they may be provided from the manufacturer of the chemical tags. Alternatively, the user of the MS device may experimentally obtain the impurity matrices as described above in connection with FIGS. 3A-B. Embodiments are not limited to using the impurity matrices as described above. For example, one of skill in the art would recognize that the impurity matrices may have any number of rows and columns, depending on the details of the chemical tags. Furthermore, while writing the impurity information in matrix form is convenient, the impurity information describing isotopic variations within the chemical tags used to label the molecules may be represented in any suitable way.

Figure 8:
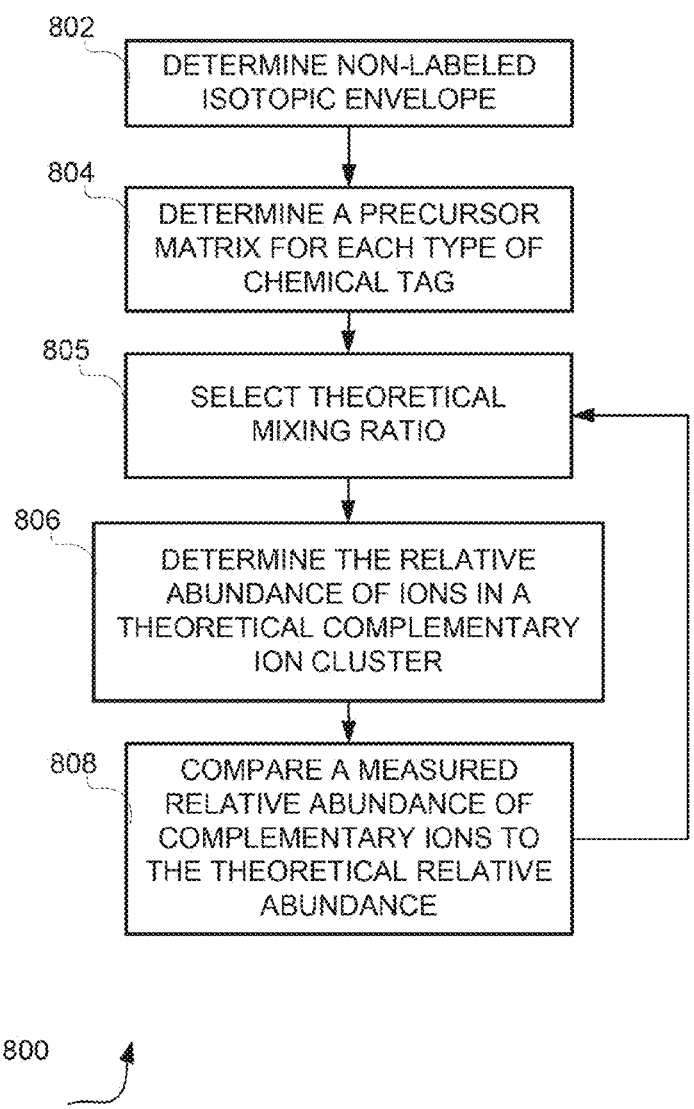
FIG. 8 is a flowchart of a method of determining the relative abundance of each type of tagged molecule according to some embodiments.

The method begins at act 802 of FIG. 8 by determining an isotopic envelope for the unlabeled molecule being quantified, the isotopic envelope representing the relative populations of each m/z channel. This envelope is represented by a vector p. The vector p may be determined in any suitable way. In some embodiments, the vector p may be calculated based on the composition of the molecule and information detailing the natural abundance of various isotopes in nature. Other embodiments may determine the vector p by experimentally determining the isotopic envelope for the molecule using, for example, mass spectrometry. Alternatively, some embodiments may simply look up the spectral envelope from a database that stores spectral envelope information for a library of molecules.

Figure 7A:
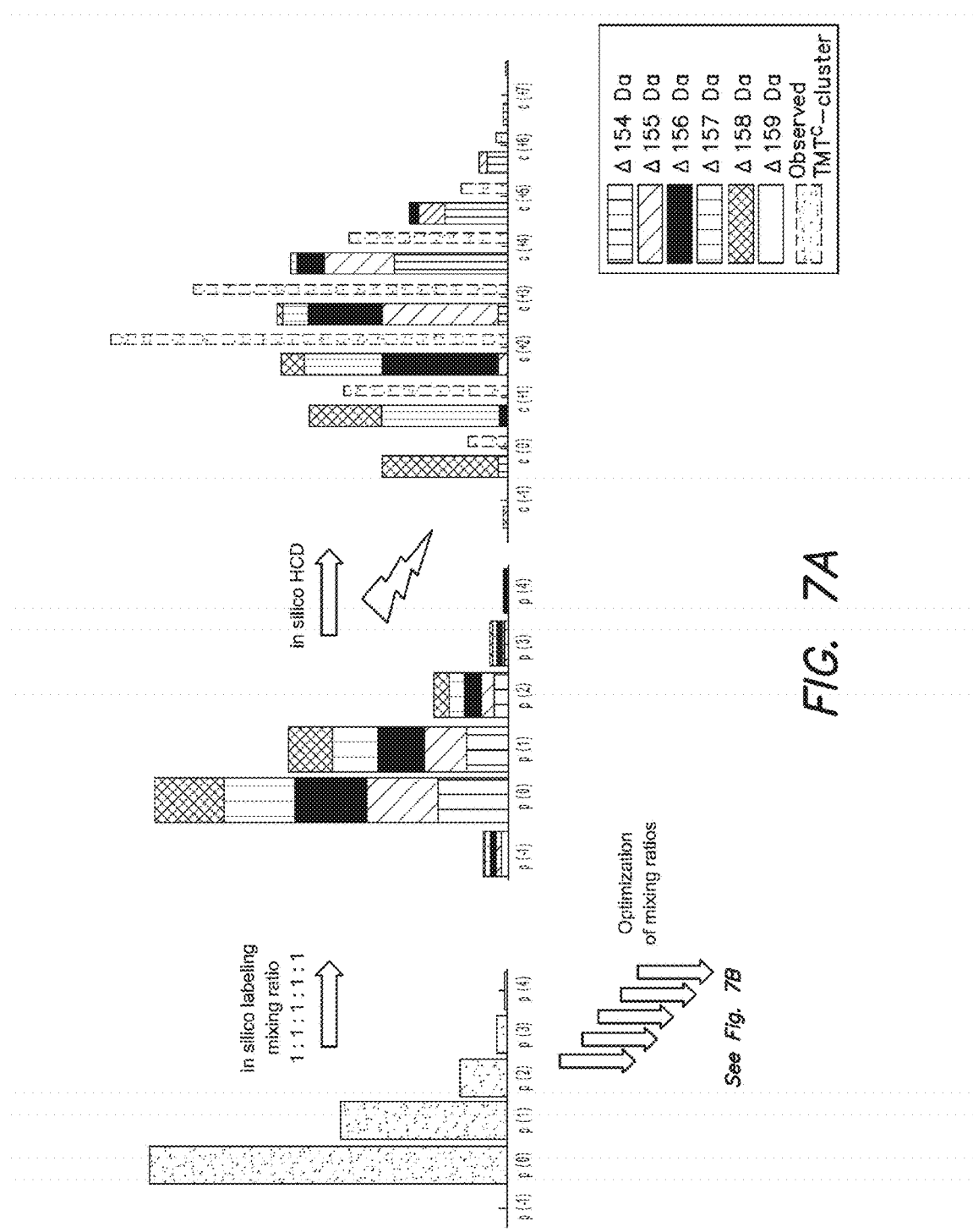
FIGS. 7A-B illustrate a method of determining the relative abundance of each type of tagged molecule according to some embodiments.
Figure 7B:
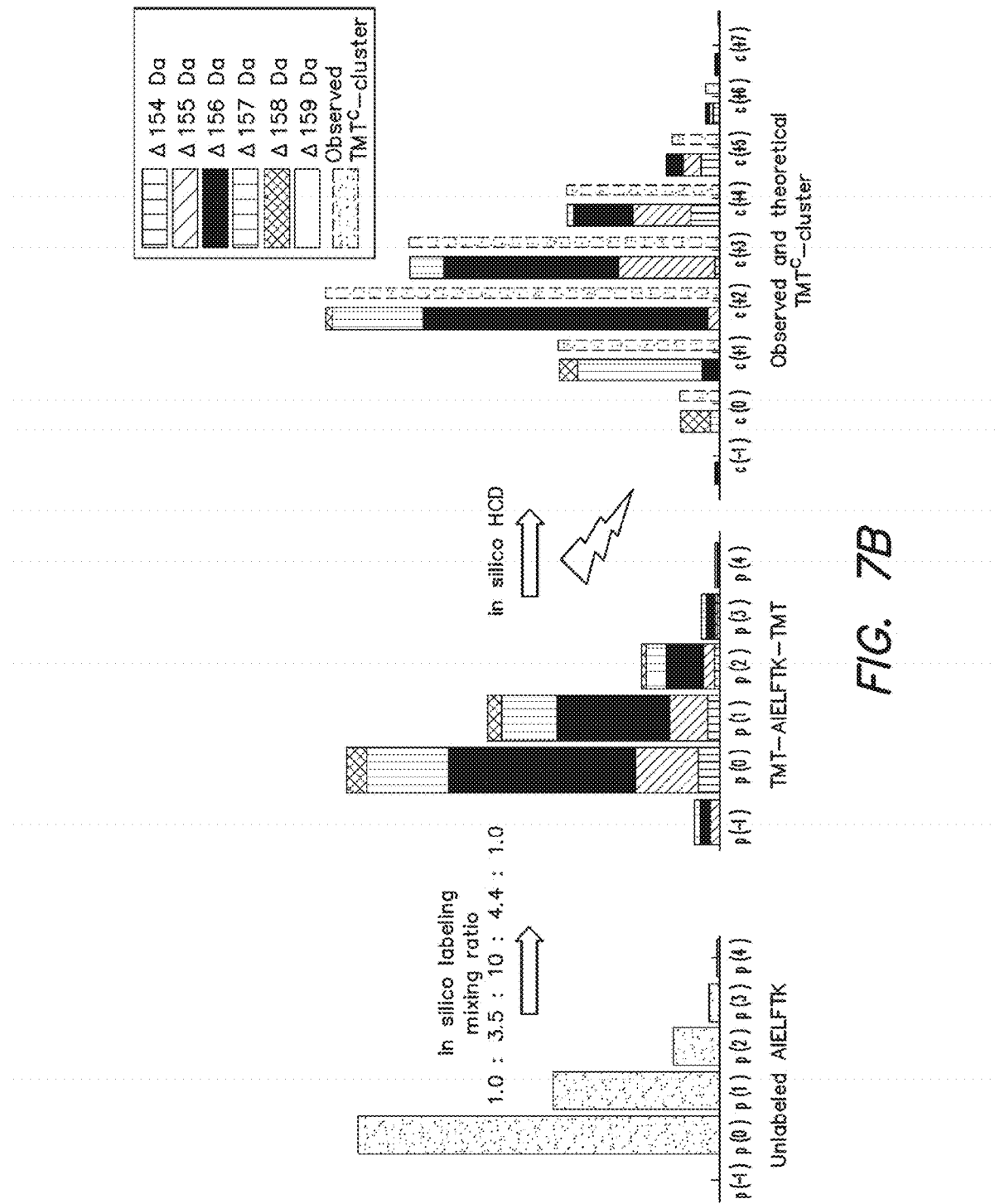

The leftmost graph of FIG. 7A illustrates the isotopic envelope for the unlabeled molecule, i.e., the vector p. The first position in the vector, p(0), is the position of the monoisotopic peak. The other positions in the vector p correspond to peaks that are one Dalton heavier than the monoisotopic peak. The vector p may be normalized to 1. The isotopic envelope of the unlabeled molecule may be determined theoretically based on the atomic makeup of the molecule and the probability that one or more of the atoms will be an isotope other than the most abundant isotope occurring in nature. Alternatively, the peaks of the isotopic envelope of the unlabeled molecule may be an experimentally measured using MS.

At act 804 of FIG. 8, a multiplexed precursor matrix $P_M$, which may be used to calculate theoretical relative abundances for the labeled molecules, is determined based on the unlabeled isotopic envelope of the molecule. The multiplexed precursor matrix may be determined by first determining individual precursor matrices $P_{TMT}$ for each of the types of tags being used. The individual precursor matrix $P_{TMT}$ may be determined based on, for example, the impurity matrices ($I_{TMT}$), the isotopic impurity vectors ($t_{TMT}$), the number of TMT-tags bound to the molecule (k) and the isotopic envelope for the unlabeled molecule (p). For TMT=126, 127, 128, 129, 130, 131, the individual precursor matrix for each type of tag may be determined as:

$$P_{TMT} = I_{TMT} * p^{*k-1} t_{TMT},$$

where the * symbol represent a convolution operation and $*^{k-1}$ indicates performing (k−1) convolution operations. The resulting $P_{TMT}$ matrices have rows that indicate the delta mass after fragmentation as described for $I_{TMT}$ and columns that indicate the position within the isotopic envelope. Columns p(−1) to p(10) are calculated in this example, but any suitable number of columns may be used. The (pseudo)-monoisotopic peak again defines the p(0) position.

The precursor matrix $P_M$ may then be determined for a given mixing ratios $r_{TMT}$ (expressed as $r_{126}$:$r_{127}$:$r_{128}$:$r_{130}$:$r_{131}$, which may be normalized to 1) by performing a weighted sum of the $P_{126}$ ... $P_{131}$ matrices:

$$P_M = \Sigma_{i=126\ldots 131} r_i P_i.$$

The middle graph of FIG. 7A illustrates the precursor matrix $P_M$ visually, each peak represents a position within the isotopic envelope of the tagged samples (i.e., the columns of the precursor matrix) and the different fill patterns represent the contribution from each of the delta masses of the tags after fragmentation (i.e., the rows of the precursor matrix).

The mixing ratio that results in a relative abundance of complementary ions that best matches the experimental data may be determined using an iterative technique. At act 805 of FIG. 8, a theoretical mixing ratio may be arbitrarily selected. For example, the starting point for the iterative technique may be the mixing ratio 1:1:1:1:1.

At act 806 of FIG. 8, the relative abundance of ions in a theoretical complementary ion cluster is determined based on the selected mixing ratio, as represented by the vector $\hat{c}$. The position $\hat{c}(0)$ is defined as the position which results from loss of the TMT-131 reporter ion of the pseudo monoisotopic peak $p(0)$. In this example, $\hat{c}$ is calculated for positions −1 to 14 using the formula:

$$\hat{c}_k = \sum_{i,j} P_{M_{i,j}}$$

with $i+k-5=j$, $k=-1 \ldots 14$, $i=1 \ldots 6$, $j=-1 \ldots 10$, which corresponds to summing the diagonals of the multiplexed precursor matrix $P_M$. An example relative abundance of ions in a theoretical complementary ion ($\hat{c}$) is illustrated in the leftmost graph of FIG. 7A. This example uses the arbitrarily selected mixing ratios for the TMT channels 126:127:128:130:131 of 1:1:1:1:1, which, as discussed above, may be the starting point of an iterative algorithm to determine the mixing ratio that best matches the experimental data. The graph compares the predicted intensity distribution in the $TMT^C$ cluster based on the distribution of mass decrements in the precursor ion cluster relative (the bars with varying fill patterns) to observed values (dashed bars).

At act 808, the theoretically calculated vector $\hat{c}$ for the $TMT^C$ ion cluster is compared with the observed ion cluster c. This comparison may use a similarity function or a difference function. Any suitable difference function may be used. For example, a cosine distance or a Euclidean distance function may be used to calculate the difference between the two vectors, c and $\hat{c}$.

In some embodiments, fitting noise of empty positions may be avoided by first calculating which positions in the theoretically predicted $TMT^C$ envelope $\hat{c}$ are populated with less than 1% of the total ion cluster for the theoretical ratios $\hat{r}_{TMT}$=0.2:0.2:0.2:0.2:0.2. For example, for some peptides, this requirement is fulfilled for the monoisotopic position $\hat{c}(0)$ to $\hat{c}(+6)$ to $\hat{c}(+8)$.

The ratios in $r_{TMT}$ may then be varied by returning to act 805 and choosing a different theoretical mixing ratio based on the comparison in act 808. By iterating and refining the theoretical mixing ratio to better represent the experimental data, the difference function is minimized. For example, a Diff function may be defined as a quadratic difference function such that the minimization is achieved by performing the operation:

$$\min_{\hat{r}} Diff(c, \hat{c}(\hat{r})) = \min_{\hat{r}} \sum_i (\hat{c}_i(\hat{r}) - c_i)^2$$

for all i where $\hat{c}_i(\hat{r}_{TMT}$=0.2:0.2:0.2:0.2:0.2$) > 0.01$ with $\Sigma_i \hat{c}_i = 1$ and $\Sigma_i \hat{c}_i = 1$. Determining the mixing proportions which minimizes the ion envelop difference function is a standard multi-variate optimization problem. In some embodiments, the minimization is an instance of convex optimization and may be solved with a local search solver, such as the fmincon function in MATLAB.

Embodiments are not limited to any particular method of determining the mixing ratio. In some embodiments, a theoretical envelope may be estimated based on some mixing ratio and compared to the experimental measurement. The process may be iterated by changing the theoretical envelope and comparing it to the experimental data. In this manner, a theoretical envelope that best matches the experimental data may be determined. This best match is what is determined to be the actual mixing ratio used in the experiment. In some embodiments, for example, different constraints may be placed on the analysis routine, such as the requirement that the components of the theoretical envelope be real and non-negative values. An alternative constraint might be that peptides derived from the same protein share the same mixing ratio.

The rightmost graph of FIG. 7A illustrates a comparison of an observed $TMT^C$ cluster envelope (the dashed bars) with ratios for the TMT channels 126:127:128:130:131 of 1.0:3.5:10:4.4:1.0 with a theoretical envelope based on an arbitrarily selected mixing ratios for the TMT channels 126:127:128:130:131 of 1:1:1:1:1 (shown as the bars with various fill patterns). Note that the height of the shaded bars do not match well with the measured result. However, when the above optimization routine is used to calculate the optimal mixing ratio, the observed and theoretical $TMT^C$ ion cluster envelopes are very closely matched, as illustrated in the rightmost graph of FIG. 7B.

Figure 9B:
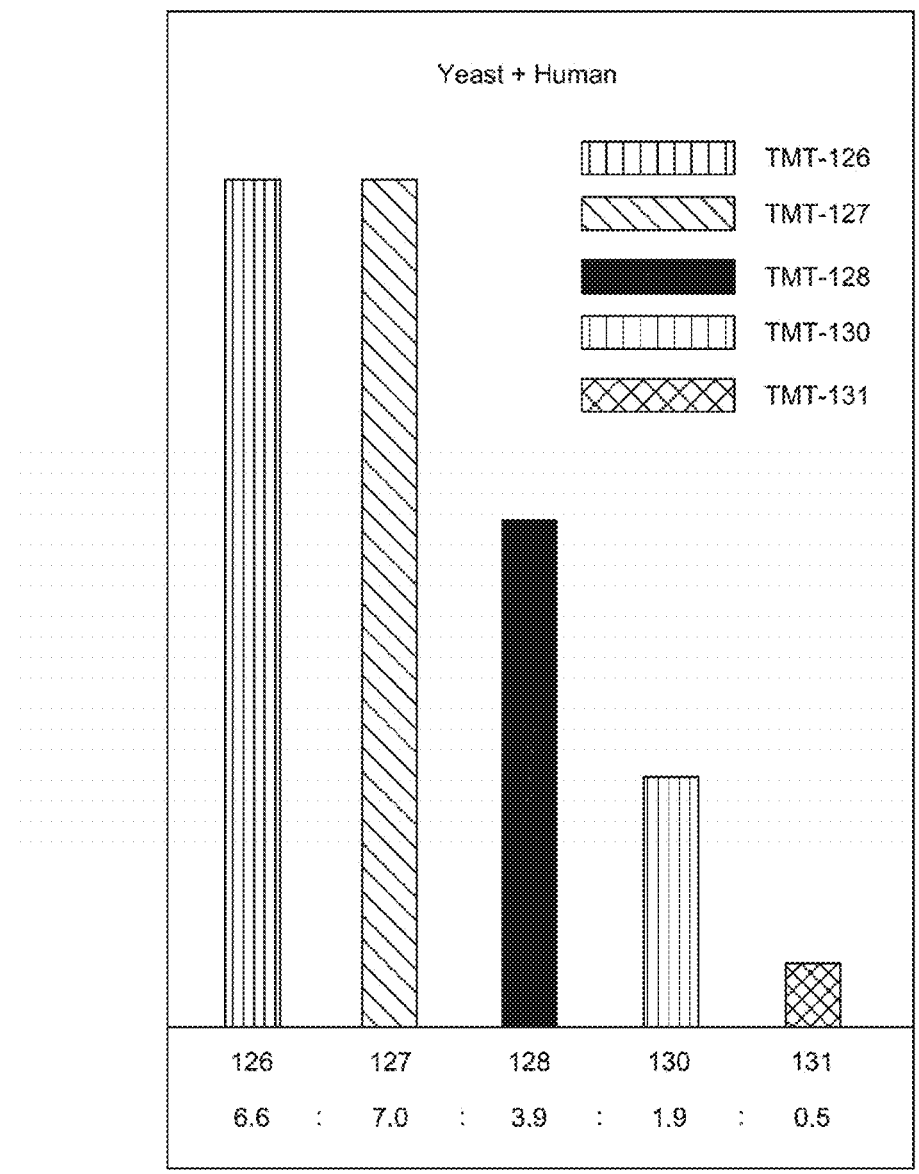
Figure 9C:
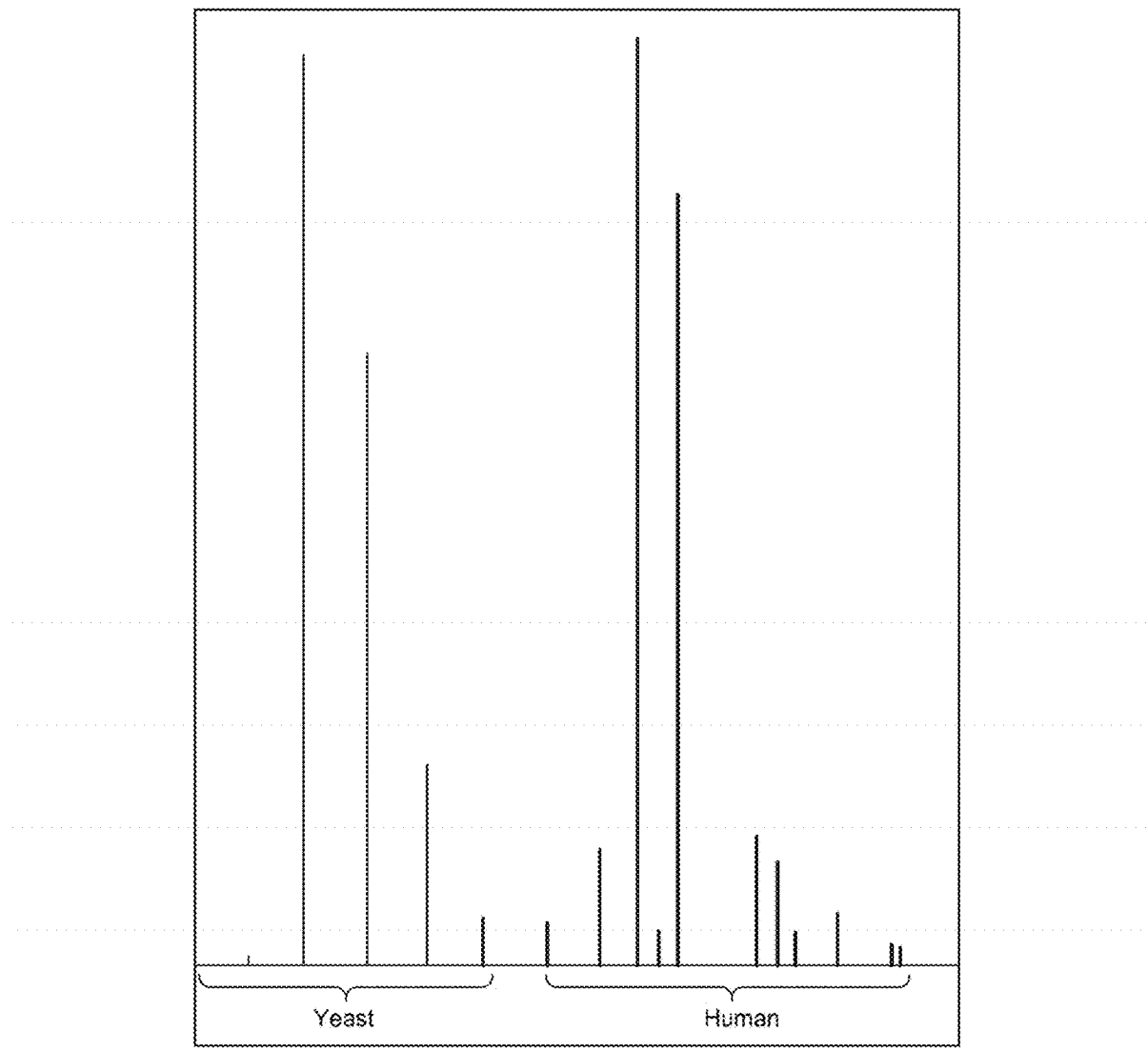

FIGS. 9A-E illustrate a further advantage of using the $TMT^C$ ion clusters for quantifying the relative abundance of a molecule in a plurality of samples. Because the position of the isotopic envelope in the $MS^2$ spectrum is dependent on the m/z of the molecule being labeled, more than one molecule may be quantified in a single experiment. The prior art, which uses the indistinguishable reporter ions to quantify the labeled molecules, cannot quantify multiple types of molecules in a single experiment because the reporter ions from each of the labeled molecules overlap in precisely the same m/z channel. FIG. 9A illustrates an $MS^2$ spectrum from an analysis where two different peptides (YTTLGK from yeast and LDEREAGITEK from a human) are labeled with the same five chemical tags. FIG. 9C illustrates labeled precursor ion clusters that are still intact and did not fragment. The positions of the two isotopic envelopes are close enough together such that a single isolation window may be used to isolate the two precursor ions simultaneously. In this particular example, a ±3 m/z isolation window was used. In some embodiments, if the two precursor isotopic envelopes are not near one another, a multi-notch isolation window, which isolates portions of the precursors at different locations, may be used.

FIG. 9B shows a zoomed in portion of the $MS^2$ spectrum corresponding to the positions of the reporter ions. There are five reporter ion channels with no way to discern what proportion of each channel was generated from either the yeast or the human peptide ion. Thus, a quantification of multiple peptides is not possible using the reporter ions.

Figure 9D:
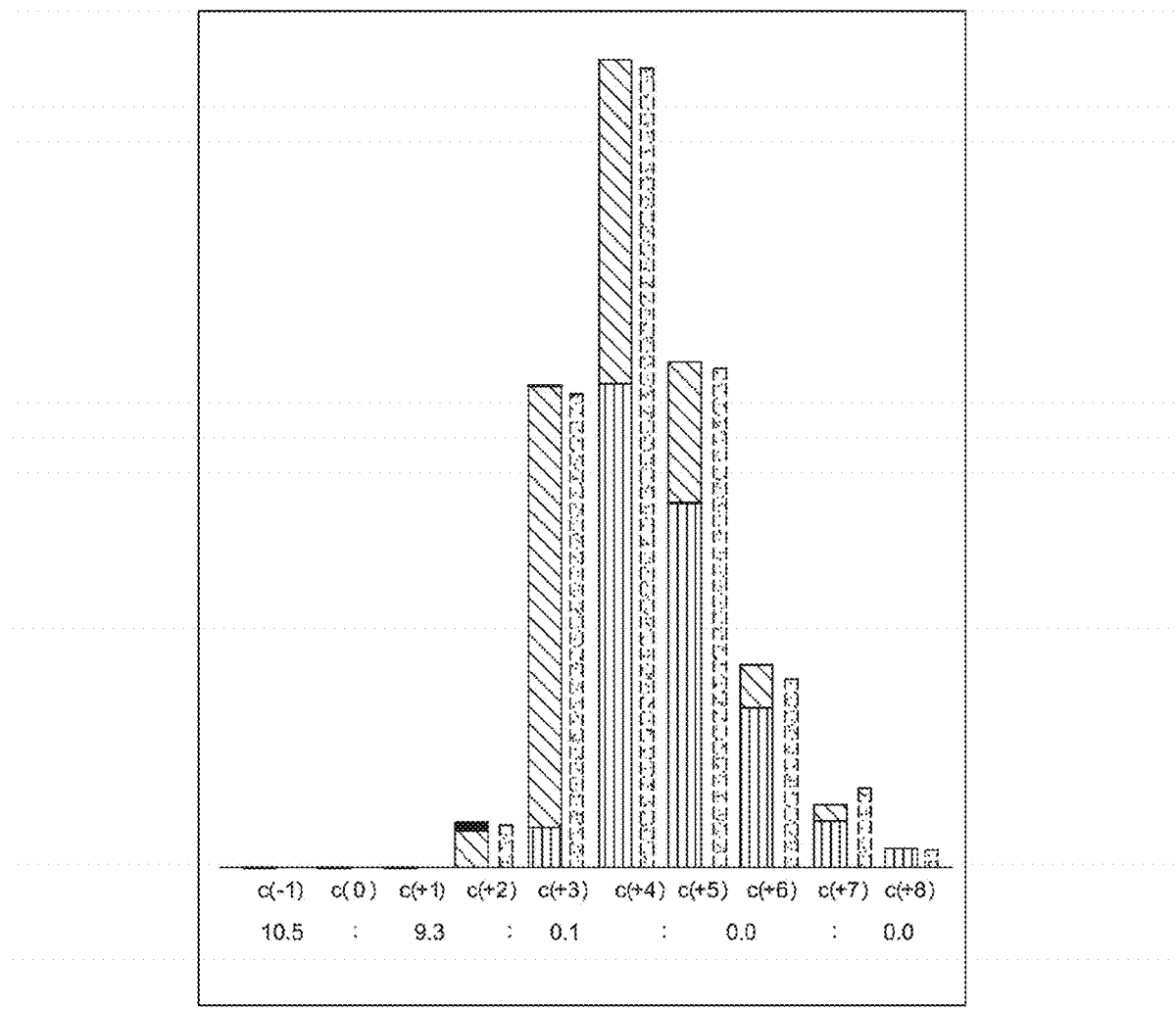
Figure 9E:
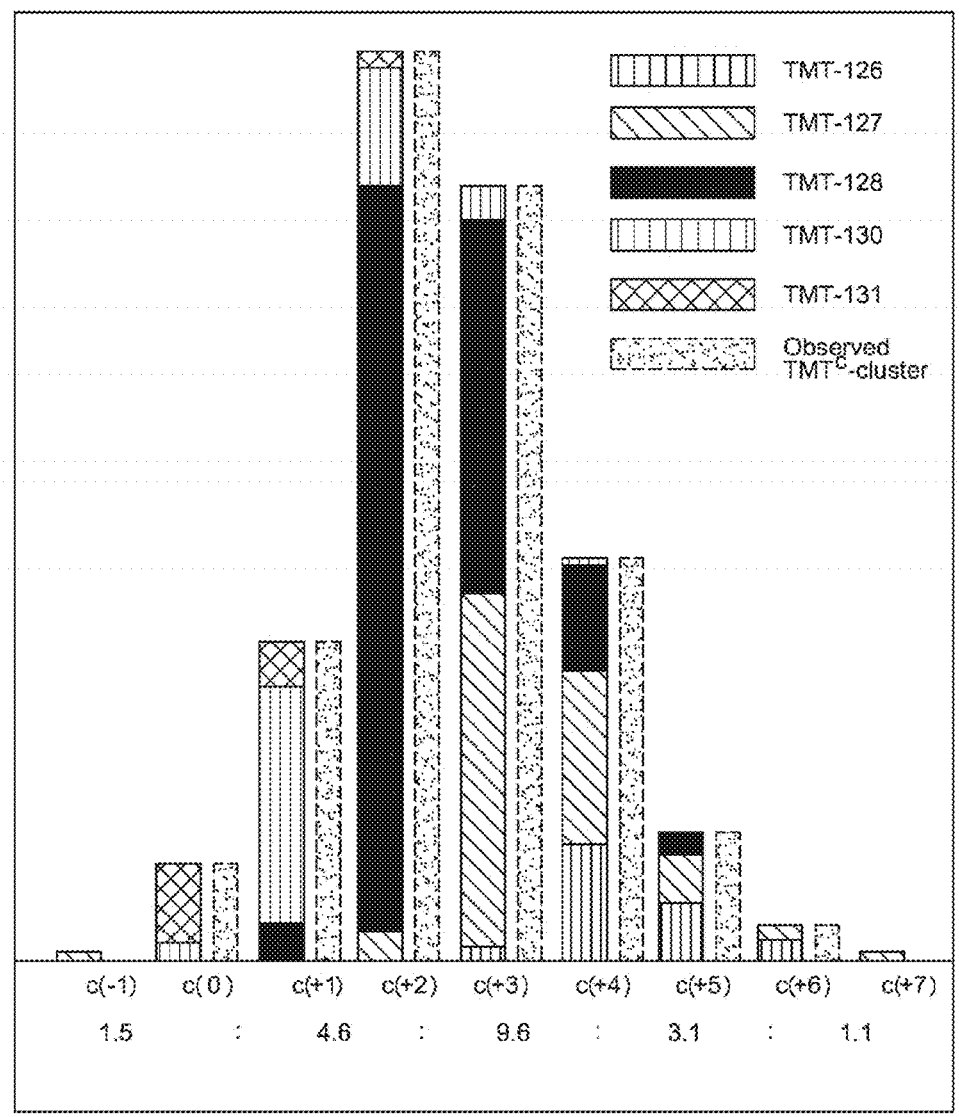

FIGS. 9D and 9E illustrate zoomed in portions of the $MS^2$ spectrum corresponding to the human $TMT^C$ ion cluster and the yeast $TMT^C$ ion cluster, respectively. The contribution from each TMT channel to the $TMT^C$ ion cluster is shown using different fill patterns and is determined through deconvolution. The resulting predictions based on deconvolution are near the actual mixing rations of the yeast and human peptides in the two-proteome sample. The ability to distinguish between the $TMT^C$ ions in the spectrum allows both peptides to be analyzed using, for example, the above analysis techniques. Embodiments are not limited to quantifying two molecules simultaneously. Any suitable number of molecules may be quantified if the isotopic envelopes of each of the molecules are distinguishable.

In other embodiments two or more precursors may be deliberately isolated, fragmented, and analyzed at once. In some embodiments the deliberate co-isolation of multiple precursors may involve using a very wide isolation window that captures multiple precursor ions simultaneously. In other embodiments each precursor ion may be isolated in a discrete step or with an isolation waveform with multiple discrete notches. In some embodiments all precursor ions are fragmented together, and in other embodiments each precursor ion may be analyzed individually.

Figure 10A:
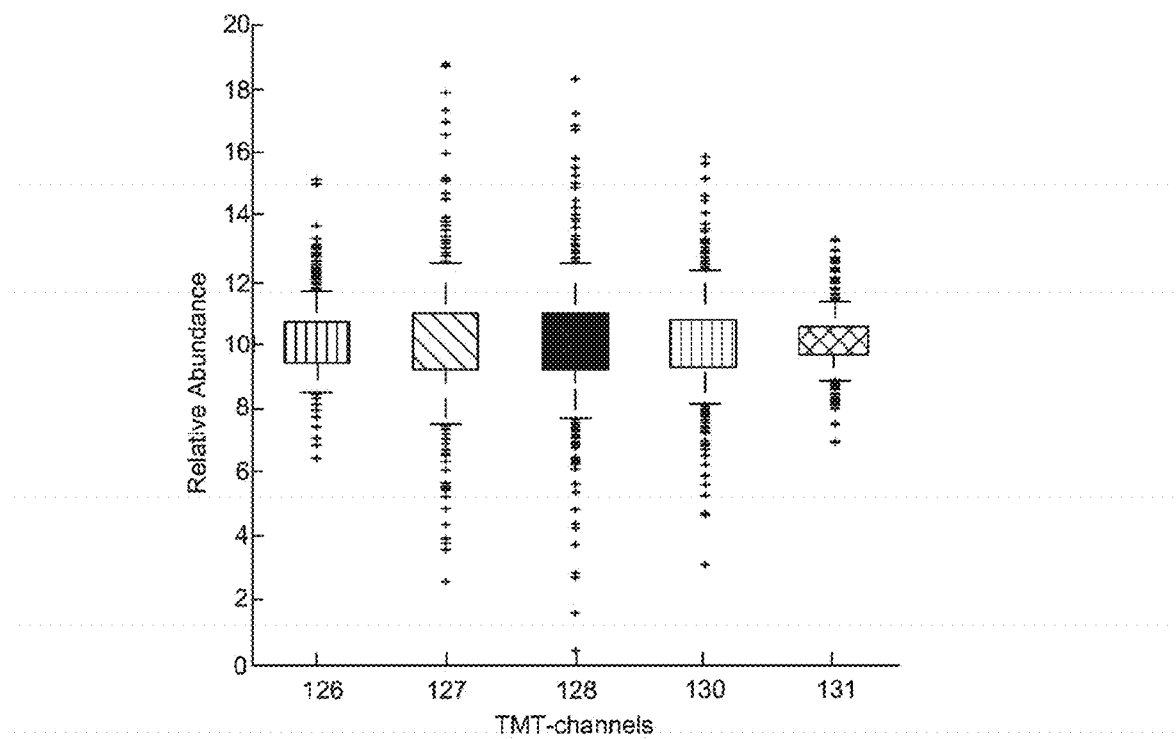
FIGS. 10A-H illustrate, using boxplots for simulated experiments, the effect of channel number and inter-channel spacing on the precision of the quantification.
Figure 10B:
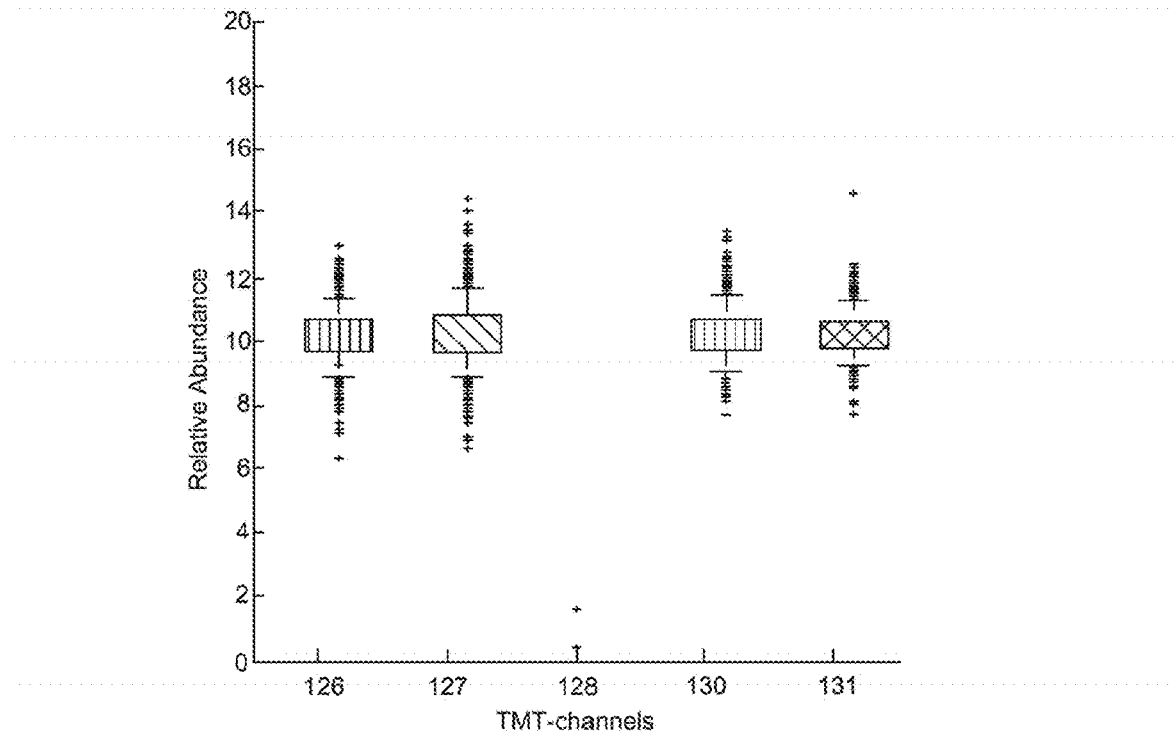
Figure 10C:
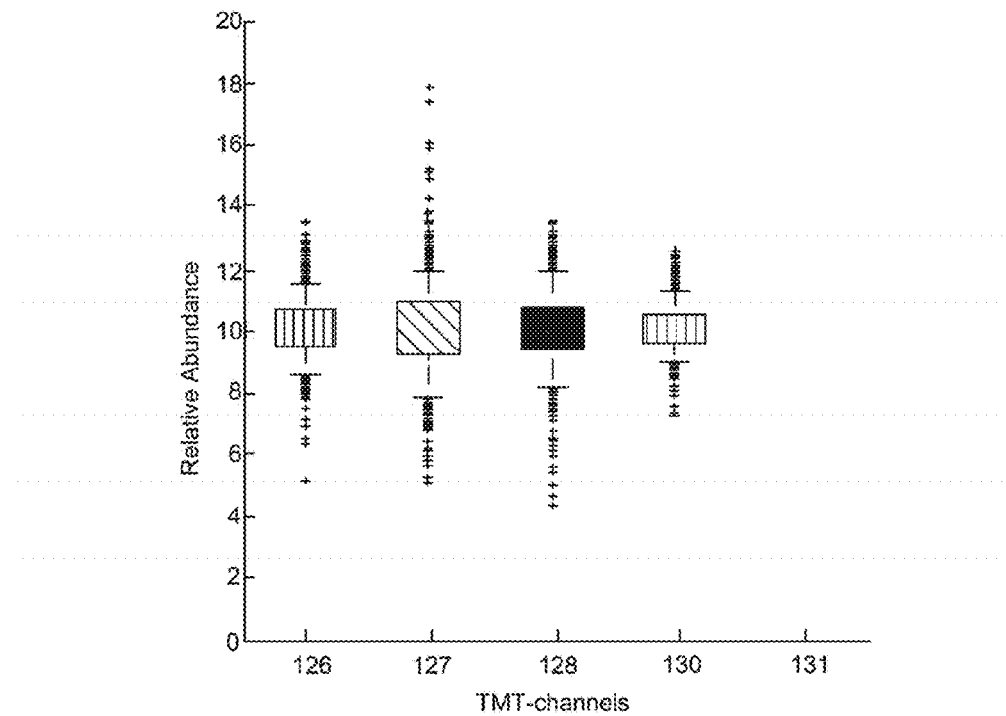
Figure 10D:
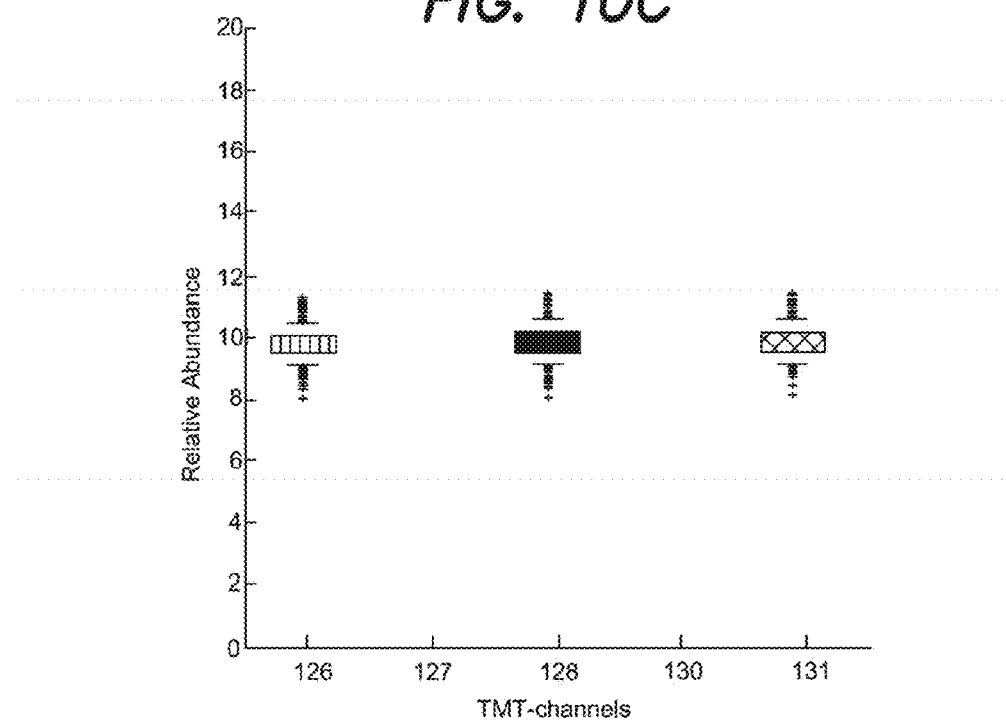
Figure 10E:
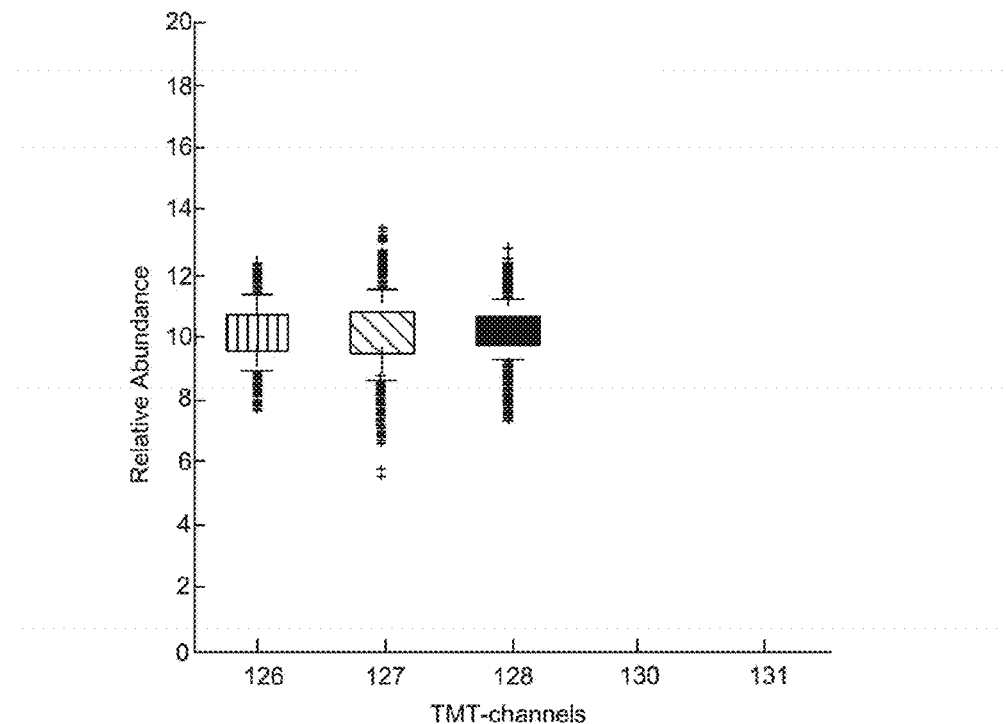
Figure 10F:
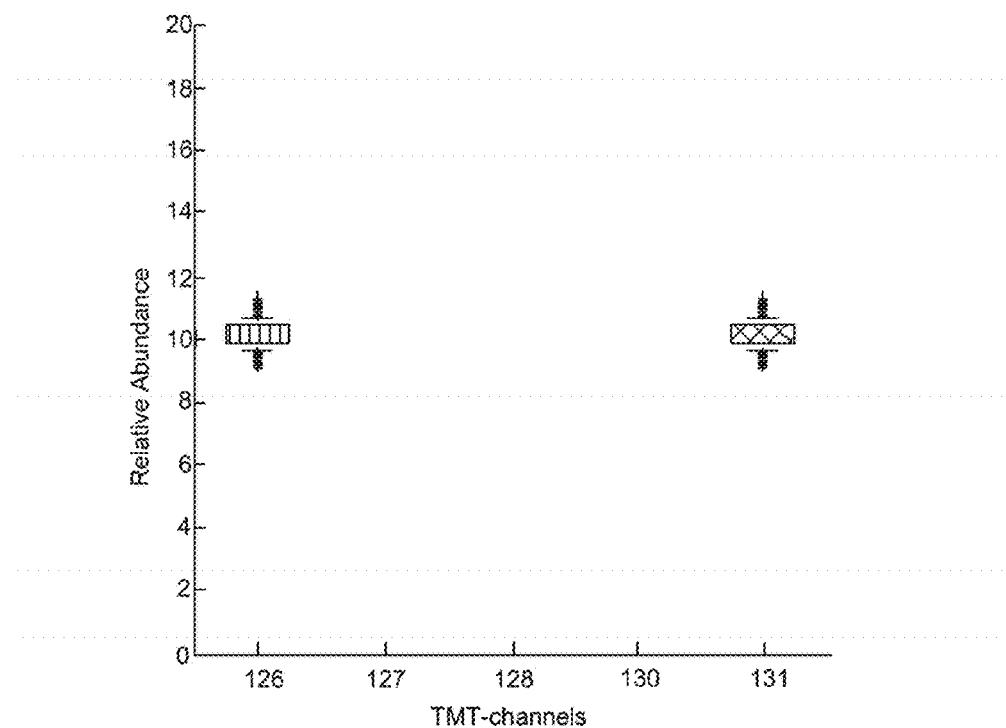
Figure 10G:
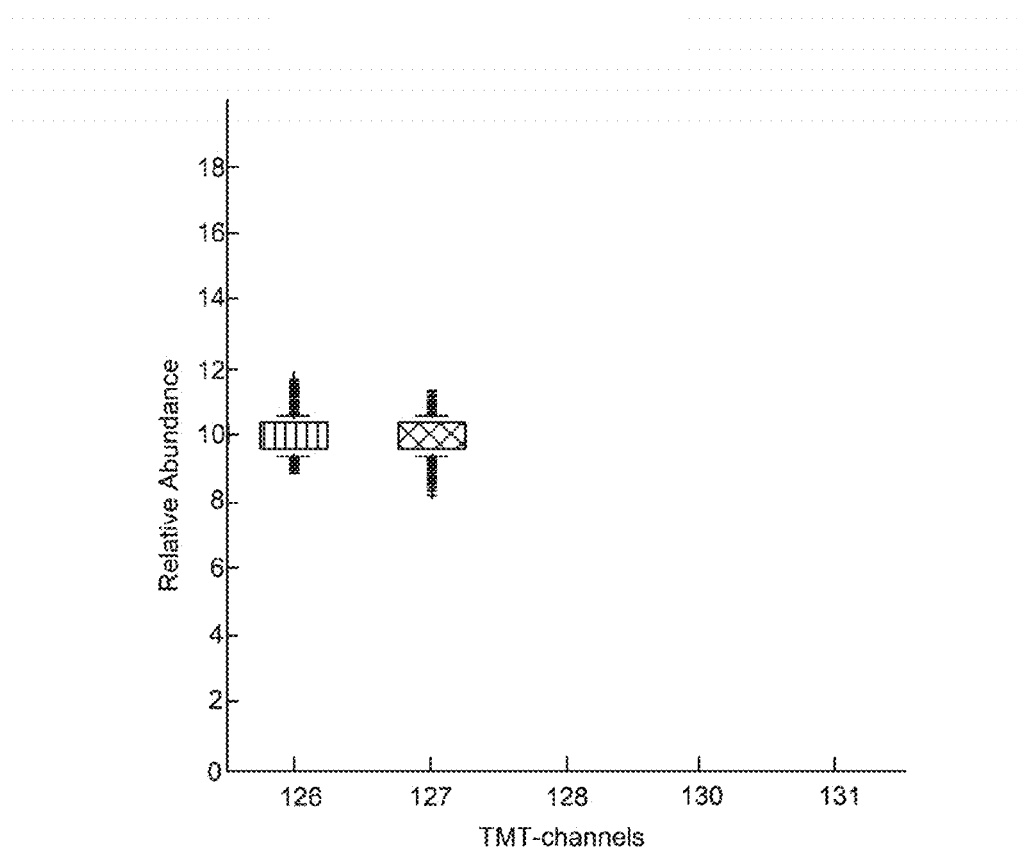
Figure 10H:
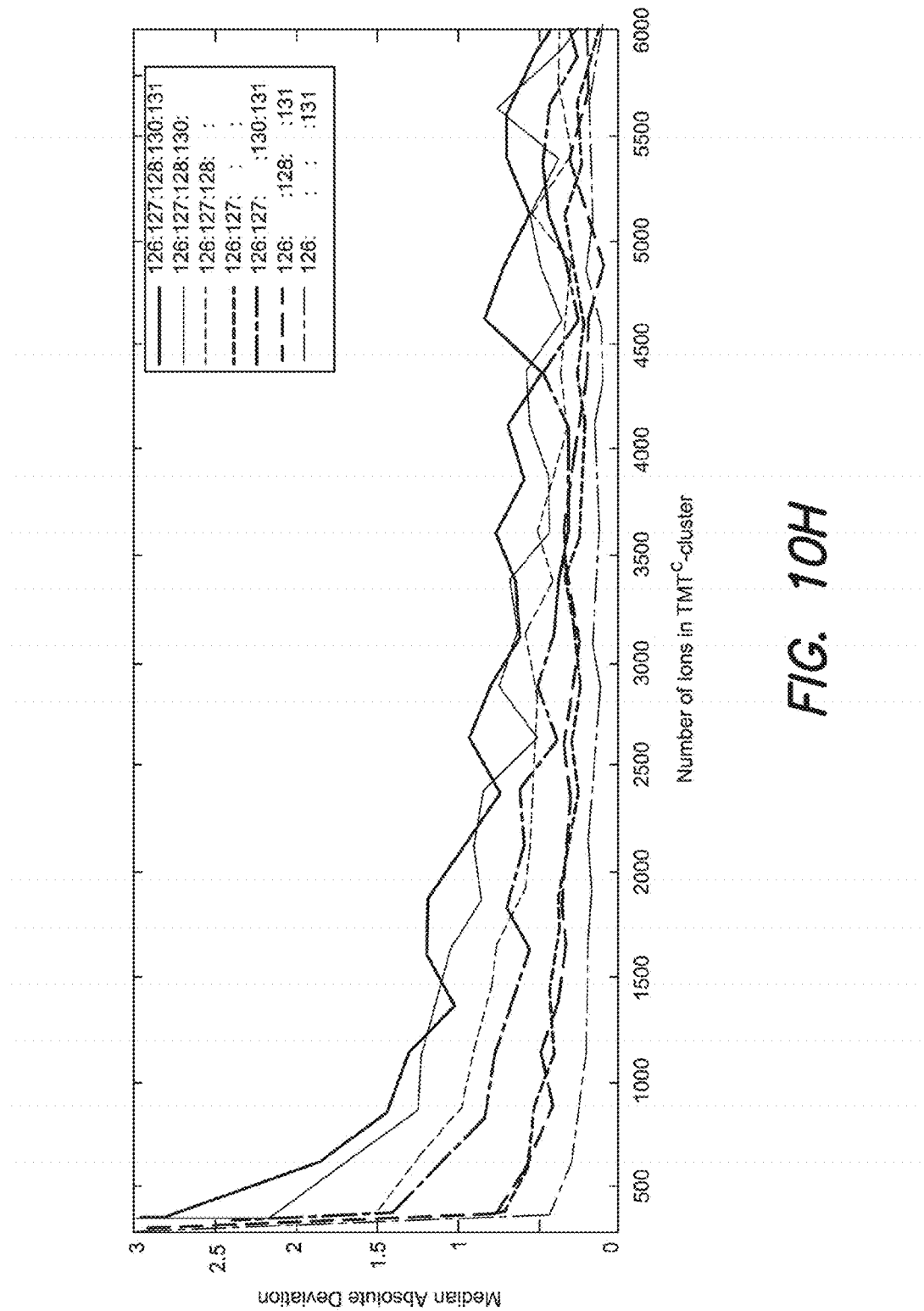

Embodiments of the invention are not limited to using any particular type of chemical tag. The above embodiments were described using TMT tags as an example. However isobaric tags for relative and absolute quantitation (iTRAQ) or any other suitable set of chemical tags may be used. Furthermore, it may be advantageous to use chemical tags that are separated in mass by more than one Dalton. For example, FIGS. 10A-H illustrate boxplots for simulated experiments similar to those described above. FIG. 10A illustrates a boxplot when five chemical tags are used to quantify the data, whereas FIG. 10B-G illustrate the results of removing one or more chemical tags from the experiment. For example, FIG. 10D shows the precision of the of the resulting quantifications to be higher when only three tags are used and each of the tags are separated by a two Dalton mass difference rather than a one Dalton mass difference. Similarly, FIG. 10F shows an increased precision resulting from using only two chemical tags with a four Dalton mass difference between the two tags. Moreover, FIG. 10H illustrates the relationship between the median deviation and the number of ions in the $TMT^C$ cluster for the different tag configurations illustrated in FIG. 10A-G. While the precision improves with increasing number of ions for all experiments, as should be expected, approximately ten-times more ions are required for the 5-plex sample to obtain a precision similar to that achieved in the experiment using 3 channels separated by 2 Da mass-spacing. Accordingly, in some embodiments, it may be advantageous to use chemical tags with mass differences greater than one Dalton.

Embodiments of the invention are not limited to interrogating each precursor using only a single scan. In certain embodiments each precursor may be interrogated using two or more scans. For example, in embodiments utilizing a pair of scans, the first scan may be used to quickly determine the $TMT^C$ production efficiency for a given precursor. Based on this initial survey scan, the subsequent repeat analysis may be tailored to produce enough $TMT^C$ signal for adequate quantitation. In some embodiments the second scan may differ from the survey scan in any suitable way. For example, the injection time used to accumulate the precursor population may be changed. In other embodiments, the second scan may differ in the fragmentation method used (e.g., HCD vs. CID), the fragmentation energy (low vs. high normalized collision energies), etc. In some embodiments the scan range for the survey scan is kept small (only encompass the $TMT^C$ ions) for the sake of keep the survey scan analysis time brief.

In other embodiment of the invention each precursor is interrogated using a pair of scans; wherein, the first scan is collected for the sake of identifying the precursor ion and the second scan is collected for the sake of determining the relative contribution of each sample to the precursor population. In this manner, the two scan are optimized for their specific goals. As such, the fragmentation method, analysis method, scan rate, etc. may differ between the two scans.

Figure 11:
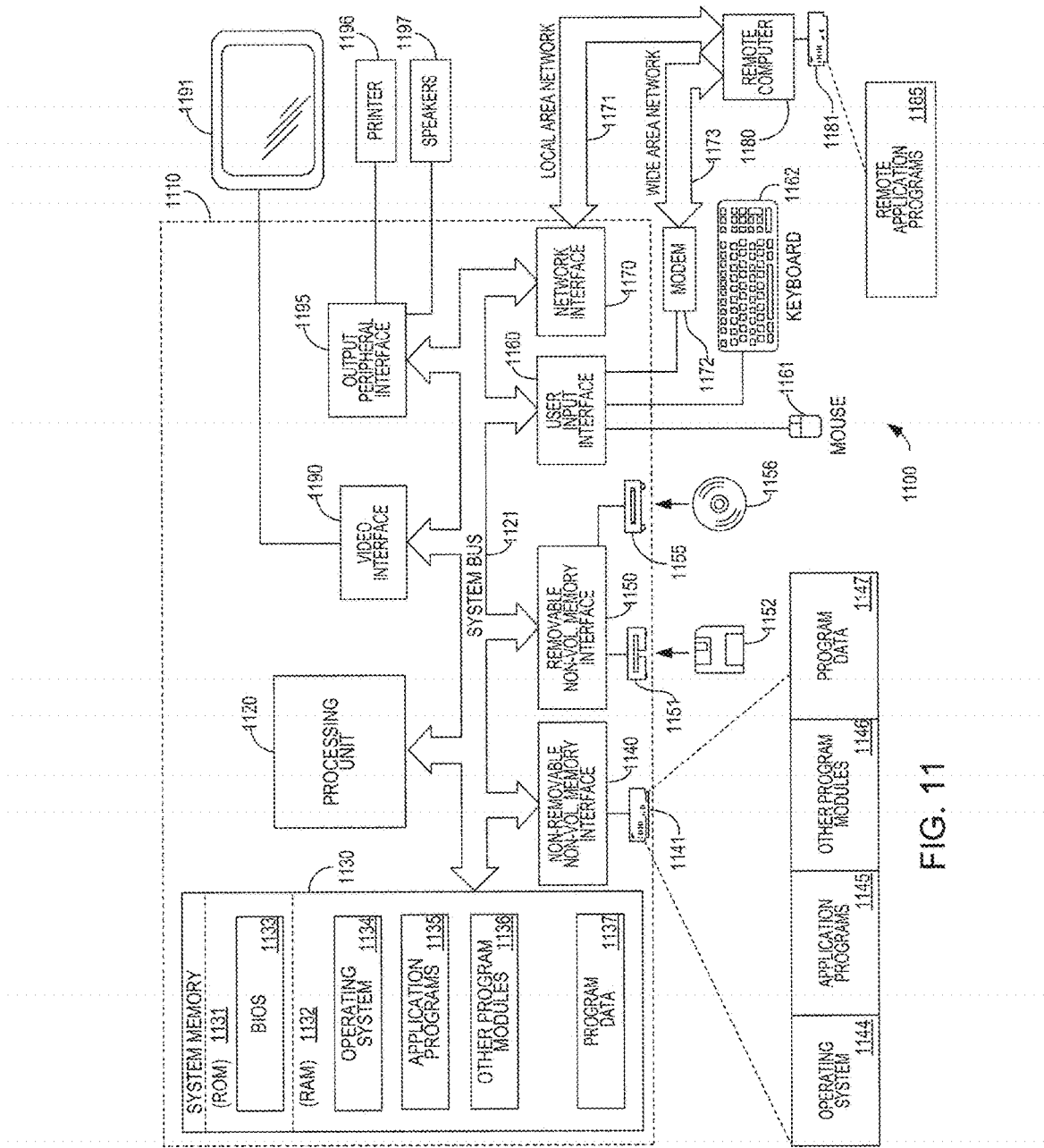
FIG. 11 is a schematic diagram of a suitable computing system environment according to some embodiments.

FIG. 11 illustrates an example of a suitable computing system environment 1100 on which embodiments of the invention may be implemented. Embodiments of the invention, such as the methods described in FIG. 6 and FIG. 8, may be implemented partially or entirely in computing system environment 1100. For example, such a computing system environment may execute software controlling a mass spectrometer used in performing some or all of the acts in FIG. 6 and FIG. 8 and also calculations to match the theoretical vector ĉ to the observed vector c.

The computing system environment 1100 is only one example of a suitable computing environment and is not intended to suggest any limitation as to the scope of use or functionality of the invention. Neither should the computing environment 1100 be interpreted as having any dependency or requirement relating to any one or combination of components illustrated in the exemplary operating environment 1100.

The invention is operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The computing environment may execute computer-executable instructions, such as program modules. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

With reference to FIG. 11, an exemplary system for implementing embodiments of the invention includes a general purpose computing device in the form of a computer 1110. Components of computer 1110 may include, but are not limited to, a processing unit 1120, a system memory 1130, and a system bus 1121 that couples various system components including the system memory to the processing unit 1120. The system bus 1121 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA)

bus, Enhanced ISA (EISA) bus, Video Electronics Standards Association (VESA) local bus, and Peripheral Component Interconnect (PCI) bus also known as Mezzanine bus.

Computer 1110 typically includes a variety of computer readable media. Computer readable media can be any available media that can be accessed by computer 1110 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 1110. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 1130 includes computer storage media in the form of volatile and/or nonvolatile memory such as read only memory (ROM) 1131 and random access memory (RAM) 1132. A basic input/output system 1133 (BIOS), containing the basic routines that help to transfer information between elements within computer 1110, such as during start-up, is typically stored in ROM 1131. RAM 1132 typically contains data and/or program modules that are immediately accessible to and/or presently being operated on by processing unit 1120. By way of example, and not limitation, FIG. 11 illustrates operating system 1134, application programs 1135, other program modules 1136, and program data 1137.

The computer 1110 may also include other removable/non-removable, volatile/nonvolatile computer storage media. By way of example only, FIG. 11 illustrates a hard disk drive 1141 that reads from or writes to non-removable, nonvolatile magnetic media, a magnetic disk drive 1151 that reads from or writes to a removable, nonvolatile magnetic disk 1152, and an optical disk drive 1155 that reads from or writes to a removable, nonvolatile optical disk 1156 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 1141 is typically connected to the system bus 1121 through an non-removable memory interface such as interface 1140, and magnetic disk drive 1151 and optical disk drive 1155 are typically connected to the system bus 1121 by a removable memory interface, such as interface 1150.

The drives and their associated computer storage media discussed above and illustrated in FIG. 11, provide storage of computer readable instructions, data structures, program modules and other data for the computer 1110. In FIG. 11, for example, hard disk drive 1141 is illustrated as storing operating system 1144, application programs 1145, other program modules 1146, and program data 1147. Note that these components can either be the same as or different from operating system 1134, application programs 1135, other program modules 1136, and program data 1137. Operating system 1144, application programs 1145, other program modules 1146, and program data 1147 are given different numbers here to illustrate that, at a minimum, they are different copies. A user may enter commands and information into the computer 1110 through input devices such as a keyboard 1162 and pointing device 1161, commonly referred to as a mouse, trackball or touch pad. Other input devices (not shown) may include a microphone, joystick, game pad, satellite dish, scanner, or the like. These and other input devices are often connected to the processing unit 1120 through a user input interface 1160 that is coupled to the system bus, but may be connected by other interface and bus structures, such as a parallel port, game port or a universal serial bus (USB). A monitor 1191 or other type of display device is also connected to the system bus 1121 via an interface, such as a video interface 1190. In addition to the monitor, computers may also include other peripheral output devices such as speakers 1197 and printer 1196, which may be connected through a output peripheral interface 1195.

The computer 1110 may operate in a networked environment using logical connections to one or more remote computers, such as a remote computer 1180. The remote computer 1180 may be a personal computer, a server, a router, a network PC, a peer device or other common network node, and typically includes many or all of the elements described above relative to the computer 1110, although only a memory storage device 1181 has been illustrated in FIG. 11. The logical connections depicted in FIG. 11 include a local area network (LAN) 1171 and a wide area network (WAN) 1173, but may also include other networks. Such networking environments are commonplace in offices, enterprise-wide computer networks, intranets and the Internet.

When used in a LAN networking environment, the computer 1110 is connected to the LAN 1171 through a network interface or adapter 1170. When used in a WAN networking environment, the computer 1110 typically includes a modem 1172 or other means for establishing communications over the WAN 1173, such as the Internet. The modem 1172, which may be internal or external, may be connected to the system bus 1121 via the user input interface 1160, or other appropriate mechanism. In a networked environment, program modules depicted relative to the computer 1110, or portions thereof, may be stored in the remote memory storage device. By way of example, and not limitation, FIG. 11 illustrates remote application programs 1185 as residing on memory device 1181. It will be appreciated that the network connections shown are exemplary and other means of establishing a communications link between the computers may be used.

Figure 12:
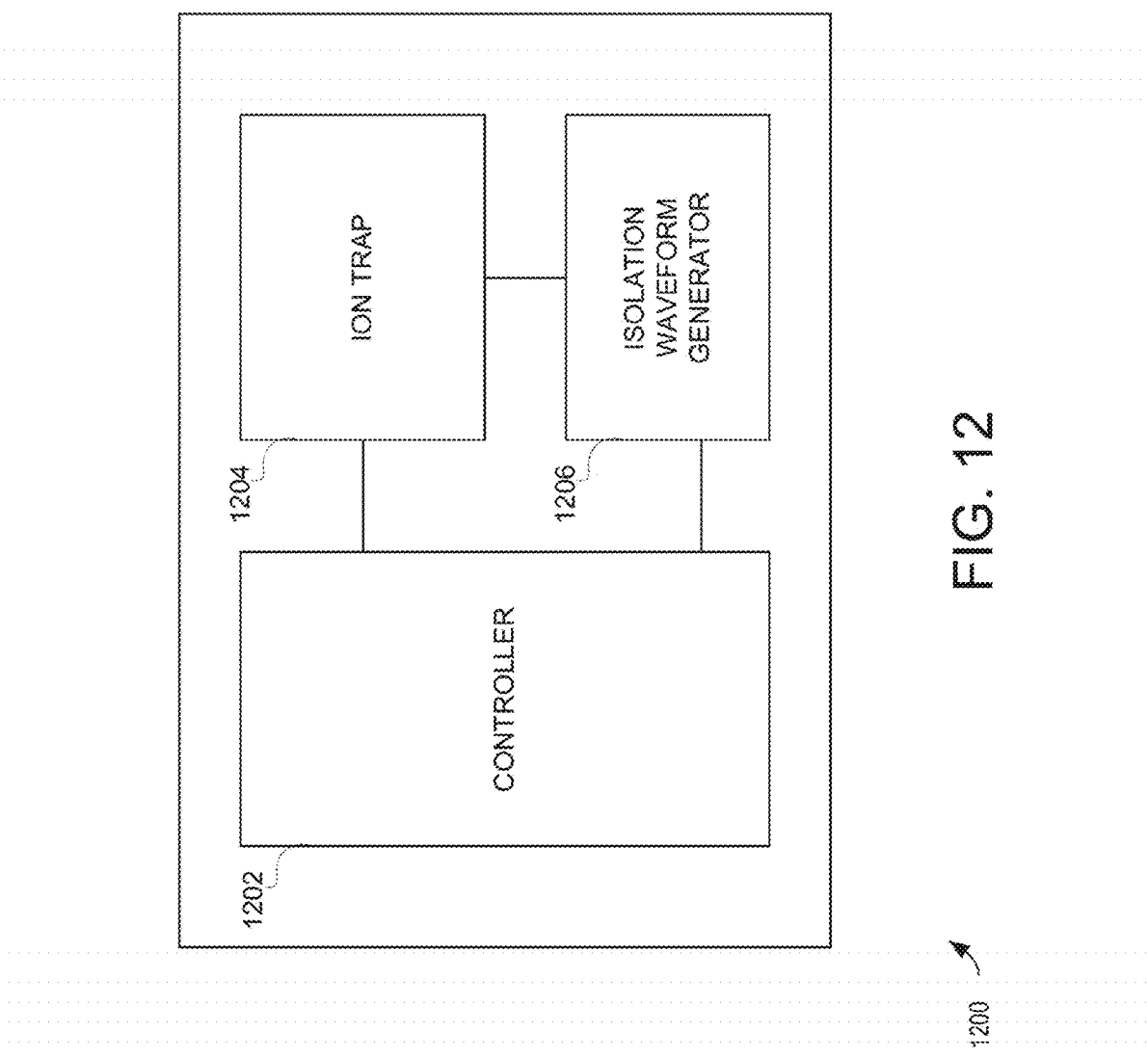
FIG. 12 is a schematic diagram of a mass spectrometry apparatus according to some embodiments.

FIG. 12 illustrates a block diagram of a mass spectrometry apparatus 1200 that may perform aspects of embodiments of the present invention. The apparatus 1200 itself may also embody aspects of the present invention. Apparatus 1200 is not intended to suggest any limitation as to the scope of use or functionality of the invention. Neither should the apparatus 1200 be interpreted as having any dependency or requirement relating to any one or combination of components illustrated in the exemplary apparatus 1200.

Apparatus 1200 may comprise a controller 1202, which may be comprised of hardware, software, or a combination of hardware and software. In some embodiments, controller 1202 determines the center and width of one or more notches used to isolate ions. For example, controller 1202 may perform at least some of the acts described in FIG. 6 and FIG. 8. Apparatus 1200 is not limited to a single controller Apparatus 1200 may comprise an ion trap 1204 and an isolation waveform generator 1206. Controller 1202 may be coupled to the ion trap 1204 and/or isolation waveform generator 1206 to allow communication. Any suitable form of coupling may be used. For example, the components may be coupled via a system bus. Alternatively, the components of apparatus 1200 may be coupled via a communications network, such as an Ethernet network. Embodiments of the invention are not limited to any specific type of coupling.

Ion trap 1204 may be any ion trap suitable for use in mass spectrometry. For example, ion trap 1204 may be a quadrupole ion trap, a Fourier transform ion cyclotron resonance (FTICR) MS, or an Orbitrap MS.

Isolation waveform generator 1206 may be any suitable device for generating the isolation waveforms used to isolate precursor ions in the ion trap 1204 prior to fragmentation. For example, isolation waveform generator 12 06 may be a radio frequency (RF) signal generator.

The inventors have recognized and appreciated that for multiplexed quantitation, using complementary ion cluster may for isobaric quantitation may overcome problems caused by interfering ions when low-mass reporter ions are used.

Accordingly, aspects of the invention may be embodied as a method determining relative abundances of one or more labeled molecules using complementary ion clusters. Some aspects may be embodied as an MS apparatus capable determining relative abundances of one or more labeled molecules using complementary ion clusters. Some embodiments may be implemented as at least one computer readable medium encoded with instructions that, when executed, perform a method for determining relative abundances of one or more labeled molecules using complementary ion clusters. The method may be, but is not limited to, the methods described in FIG. 6 and FIG. 8.

The invention is not limited to using any specific number of chemical tags or type of chemical tag. Further, it should be appreciated that the invention is not limited by the techniques used to fragment precursor ions to generate the $MS^2$ spectrum. Moreover, it should be appreciated that the invention is not limited by the techniques used to isolate the precursor ions prior to fragmentation.

A Specific Example of the Above Techniques

Having thus described several aspects of at least one embodiment of this invention, the following is a specific example of the techniques described in some embodiments.

Introduction

Mass spectrometry (MS)-based proteomics has undergone remarkable improvements over the last few years, resulting today in the identification of more than 10,000 proteins from mammalian samples in a single experiment. While protein identification is now mature, accurate quantification among multiple conditions remains a challenge. Unpredictable ionization efficiencies currently prevent absolute quantification of protein abundance in high-throughput experiments. To avoid this limitation, methods have been developed where peptides from different conditions can be isotopically labeled, so that their chemical structure is identical but their isotopic composition differs. When analyzed by MS the relative change in protein abundance can be inferred from the relative abundance of the ions, which are unique to the different conditions investigated.

Most commonly, peptides are quantified from $MS^1$ spectra, based on relative abundance of differentially-labeled species. One example is metabolic labeling. Alternatively, peptides from proteins obtained from different experimental conditions can be chemically modified to incorporate stable isotopes for quantification. A major disadvantage of these $MS^1$ based quantification methods is that the complexity of the $MS^1$ spectrum increases with the number of differentially modified peptides, so that data acquisition speed and sensitivity is reduced due to redundant $MS^2$ collection. While multiplexed proteomics with $MS^1$-based quantification is feasible—e.g. reductive dimethylation with Lys-C digested peptides allows the generation of five distinguishable species—the number of proteins that can be identified and quantified is reduced due to the increased complexity of the spectra. Hence, deep coverage of complex mixtures using $MS^1$-based quantification is currently only used for 2 or maximally 3 conditions. Thus there is a great need for a practical means of comparing a large number of samples in a single experiment, without sacrificing depth of coverage.

Isobaric tags, like TMT or iTRAQ, promised such quantitative multiplexed proteomics with deep coverage. Peptides labeled with these tags have undistinguishable mass in the $MS^1$ spectrum, thus not increasing the complexity of the spectrum, but after fragmentation each component of a multiplexed sample produces a reporter ion with unique mass in the low m/z region, which can be used for relative quantification. Presently up to 8 channels have been commercialized. Isobaric labeling can be combined with traditional $MS^1$-based quantification to increase the multiplexing capacity. An 18-plex experiment has been demonstrated.

There is a serious shortcoming of isobaric labeling. When analyzing complex mixtures, peptides, selected for fragmentation are typically contaminated by co-eluting ions of lower abundance. Reporter ions therefore originate from both target and interfering ions, which cause a distortion of the quantification. Two strategies have been introduced to overcome this problem. Ting et al. re-isolated the most abundant ion in the $MS^2$ spectrum and re-fragmented it. The resulting reporter ions in the $MS^3$ spectrum were then almost exclusively derived from the target peptide. Alternatively, Wenger et al. reduced the charge state of the precursor peptide using proton transfer ion-ion reactions (PTR) prior to fragmentation, thereby removing interfering ions with different charge states. While both methods drastically improve the accuracy and precision of quantification, they come at the cost of decreased data acquisition speed and sensitivity.

Here, we introduce an alternative approach for accurate isobaric quantification. It does not require an additional purification step but rather exploits the high mass accuracy and resolution of modern mass-spectrometers, including Orbitrap, FT-IR, and TOF instruments. As an alternative to using the reporter ions in the low m/z region of the $MS^2$ spectrum (TMT reporter ions), we quantify sample differences based on the complement TMT fragment ion cluster ($TMT^C$ cluster), which originates from partial loss of the TMT-tag (FIG. 2A-C, FIG. 4). $TMT^C$ clusters carry the equivalent quantitative information about the relative levels of the differentially labeled peptides as the low mass reporter ions and are essentially their complement. The position of the $TMT^C$ cluster is charge-state specific and the mass accuracy of modern instruments can easily distinguish fragment ions that differ by less than 0.02 m/z, sufficient for accurately quantifying the $TMT^C$ clusters. By analyzing mixtures of TMT-labeled yeast and human peptides with known but different mixing ratios, we show that this method generates accurate quantitative data unaffected by interfering peptide ions. Finally, we demonstrate that this method can quantify multiple distinct peptides in the same $MS^2$ spectrum if they are co-fragmented. This opens up the future possibility to parallelize quantification of isobarically labeled peptides, potentially multiplying the number of quantified peptides in a multiplexed proteomic experiment.

Results and Discussion

The Complement TMT Ion Cluster

Peptides labeled with any one of six different TMT channels are indistinguishable in the $MS^1$ spectrum but can be quantified upon fragmentation based into their low m/z reporter ions (reporter ions). Upon closer inspection of $MS^2$ spectra from TMT-labeled peptides, we observed another ion cluster that we assigned to peptide ions solely fragmented at a bond within the TMT tags (FIG. 4, 5B). These ions are generated by cleavage of the bond between the carbonyl carbon and the secondary amine of the TMT label (FIG. 2A). The leaving group typically takes a charge; hence, the $TMT^C$ product ions have one less charge than the precursor. We termed these fragment ions complement TMT ($TMT^C$) ions.

$TMT^C$ ions carry most of the mass-balancing group, and therefore contain information about the relative differences of the labeled peptides. Because the labeled carbonyl carbon is part of the leaving group, the $TMT^C$-130 and $TMT^C$-129 ions are indistinguishable in our analysis (FIG. 2A). These complementary ion clusters are more complicated than their related low mass reporter ions because each also reflects the isotopic envelope of the labeled peptide. Hence the $TMT^C$ ion clusters of neighboring TMT channels overlap. To obtain the relative peptide level ratios we essentially have to de-convolve the $TMT^C$ ion cluster with the isotopic envelope of the precursor-peptide ions (FIG. 4). While it seems counterintuitive to use the $TMT^C$ cluster for quantification when the low m/z reporter ions quantitative information is easily obtainable, the $TMT^C$ ions have the principle advantage that their unique location in the spectrum depends on the exact mass and charge of the tagged peptide (FIG. 4). In contrast the small TMT reporter ions from both the target and any co-isolated peptides are indistinguishable. We therefore reasoned that the peptide-specific $TMT^C$ cluster would allow quantification at the $MS^2$-level with negligible interference from co-eluting peptides, avoiding the need of an additional gas-phase purification step.

Deconvolution of $TMT^C$ Cluster in a $MS^2$ Spectrum with Significant Interference To evaluate the accuracy of quantification using the $TMT^C$ cluster, and in particular to test its susceptibility to interference, we created a sample of known mixing ratios in which we could identify and quantify the interference of co-eluting peptides. We combined 1 µg:4 µg:10 µg:4 µg:1 µg of Lys-C-digested yeast peptides labeled with TMT in the channels 126, 127, 128, 130, and 131, respectively. To simulate interference, we added a mixture of 10 µg:10 µg human Lys-C-digested peptides labeled with TMT-126 and TMT-127, respectively (FIG. 5A). We omitted the TMT-129 channel as the $TMT^C$-129 and $TMT^C$-130 ions are indistinguishable (FIG. 2A). When we analyzed the interference sample using the traditional TMT reporter ions, we found that peptides exclusive to yeast were accurately quantified in the interference free channels (128, 130, and 131), but the relative abundance in the channels with human interference (126, and 127) were heavily distorted due to contaminating reporter ions of human origin (FIG. 5D). In a real biological sample, where the mixing ratios would be unknown, we would be unable to distinguish which fraction of the reporter ions originated from the peptide of interest and which fraction originated from interfering co-eluting peptides.

The $MS^2$ spectrum shown in FIG. 5C is from an experiment analyzed on a QExactive with ±2 m/z isolation width, a 90-min gradient, and 35 k nominal resolution at 200 m/z. The spectrum identifies the yeast peptide AIELFTK. In the preceding $MS^1$ spectrum, the precursor's isotopic envelope is marked in brown. Many other peaks are also visible within the isolation width for the $MS^2$ analysis (FIG. 5C). The TMT reporter ions are located in the low m/z region of the $MS^2$ spectrum. The spectrum's peak height and deduced relative abundance in FIG. 5D do not completely agree as the intensity information is derived from the peak area, and we apply correction factors provided by the vendor to compensate for isotopic impurities. The $TMT^C$ cluster is located in the high m/z region of the spectrum (FIG. 5B, E). In this example the precursor ions carry two charges while the $TMT^C$ ions are singly charged. Unlike the reporter ions, the position of this ion cluster is dependent on the exact mass and charge state of the precursor. We define the peak of $TMT^C$ ions that are derived from the TMT-131 labeled pseudo-monoisotopic precursor as the c(0) position and label all other peaks relative to this position. While in some spectra the $TMT^C$ clusters of co-isolated peptides are easily observable (e.g. see FIGS. 9A-E), often this is not the case. We believe this is due to interference originating from many different, low abundant peptides, presumably often with different charge states, resulting in very low abundant and highly dispersed $TMT^C$ ions throughout the spectrum. We note that PTR experiments performed in the Coon lab demonstrated that isolation of ions with the charge state of the precursor peptide alone was sufficient to remove most interference.

Deducing the original mixing ratios from the $TMT^C$ ion cluster is more complicated than deriving it from the low m/z reporter ions. While the mass-balancing part of the TMT-tag essentially encodes the relative quantitative information in the same way as the reporter ions, this information is convolved with the isotopic envelope of the labeled peptide. To deduce the original mixing ratio we therefore essentially have to de-convolve the $TMT^C$ cluster with the isotopic envelope of the precursor peptide. Also, isotopic impurities from the TMT tags need to be considered (for detailed description of our calculation see Materials and Methods (below) and FIGS. 3A-B and 7A-B). The $TMT^C$ quantification in FIG. 5 reports relative ratios of 1.0:3.5:10:4.4:1.0, which indicates similar ratios for channels with and without interference close to the known mixing ratios (FIG. 5 E). In contrast the reporter ion ratios are reported as 5.3:7.9:10:4.4:1.0 with a strong ratio distortion in the channels with interference (compare FIG. 5D).

Figure 13A:
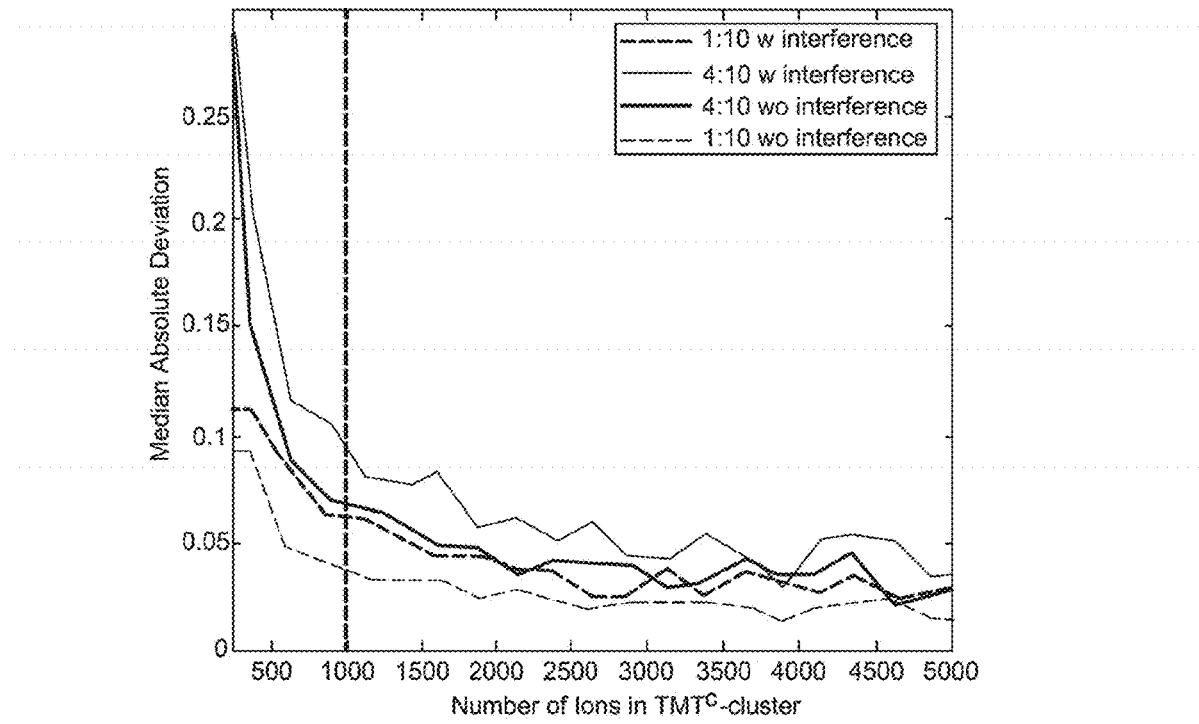
FIGS. 13A-F illustrate the filtering of quantitative data based on complementary ions according to some embodiments.
Figure 13B:
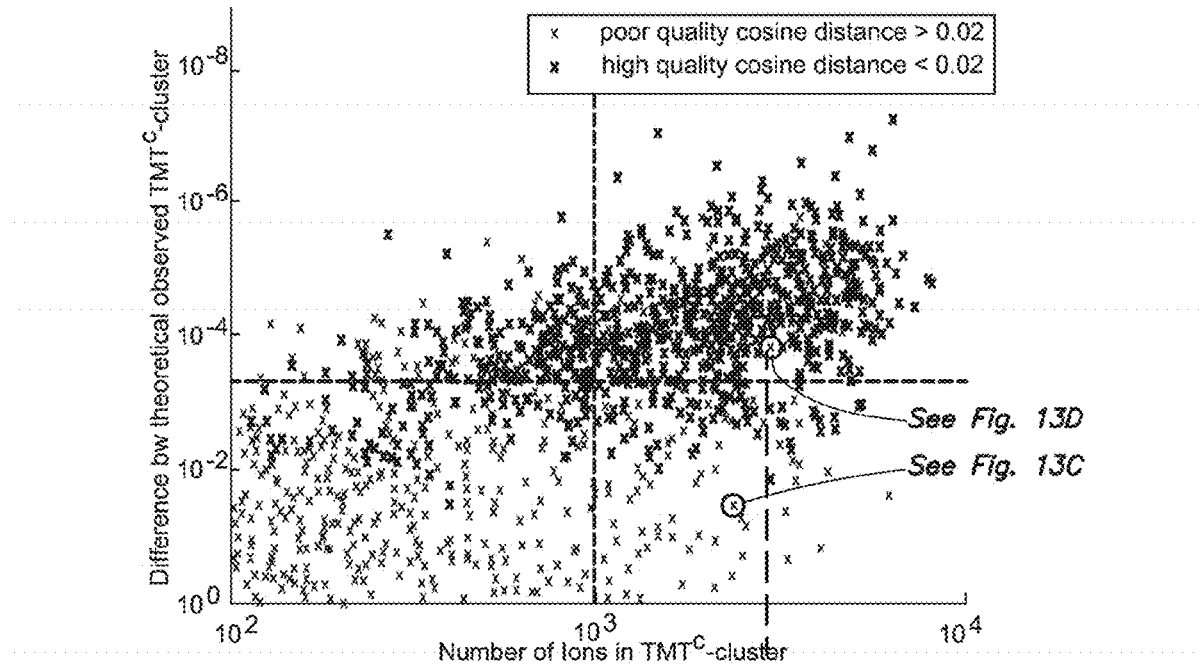
Figure 13C:
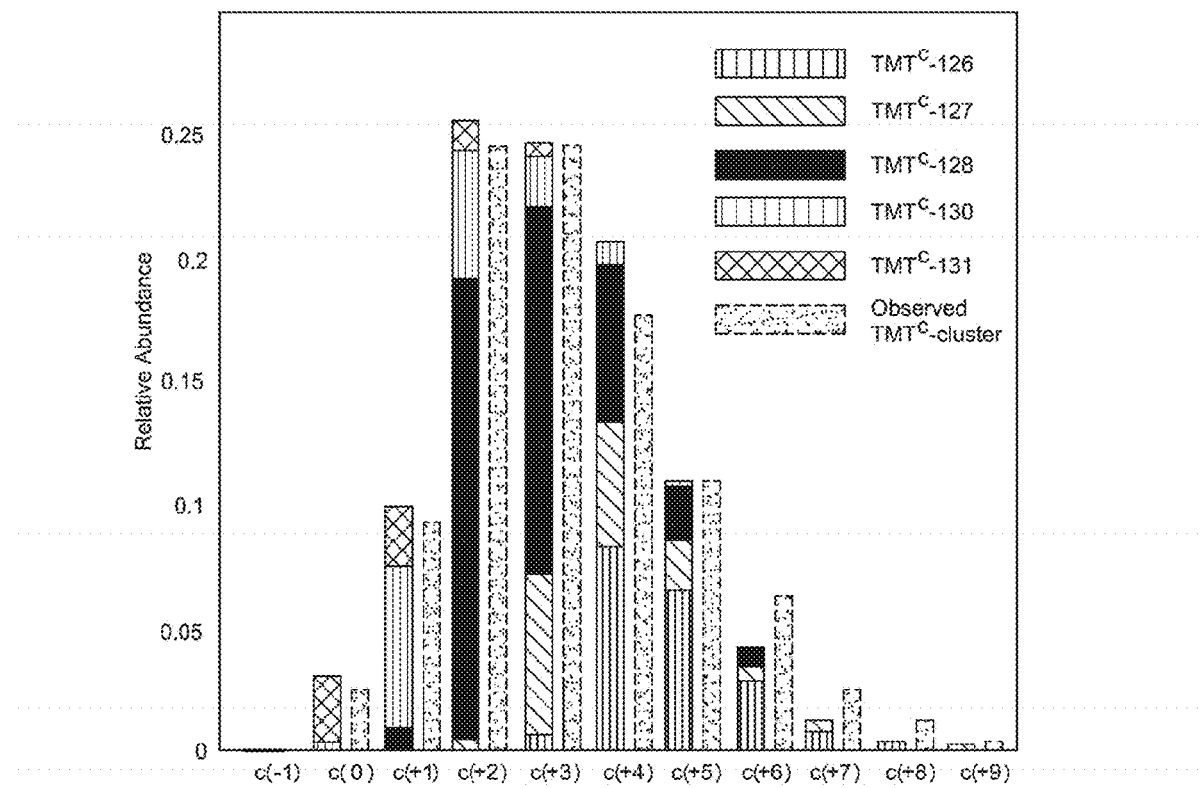
Figure 13D:
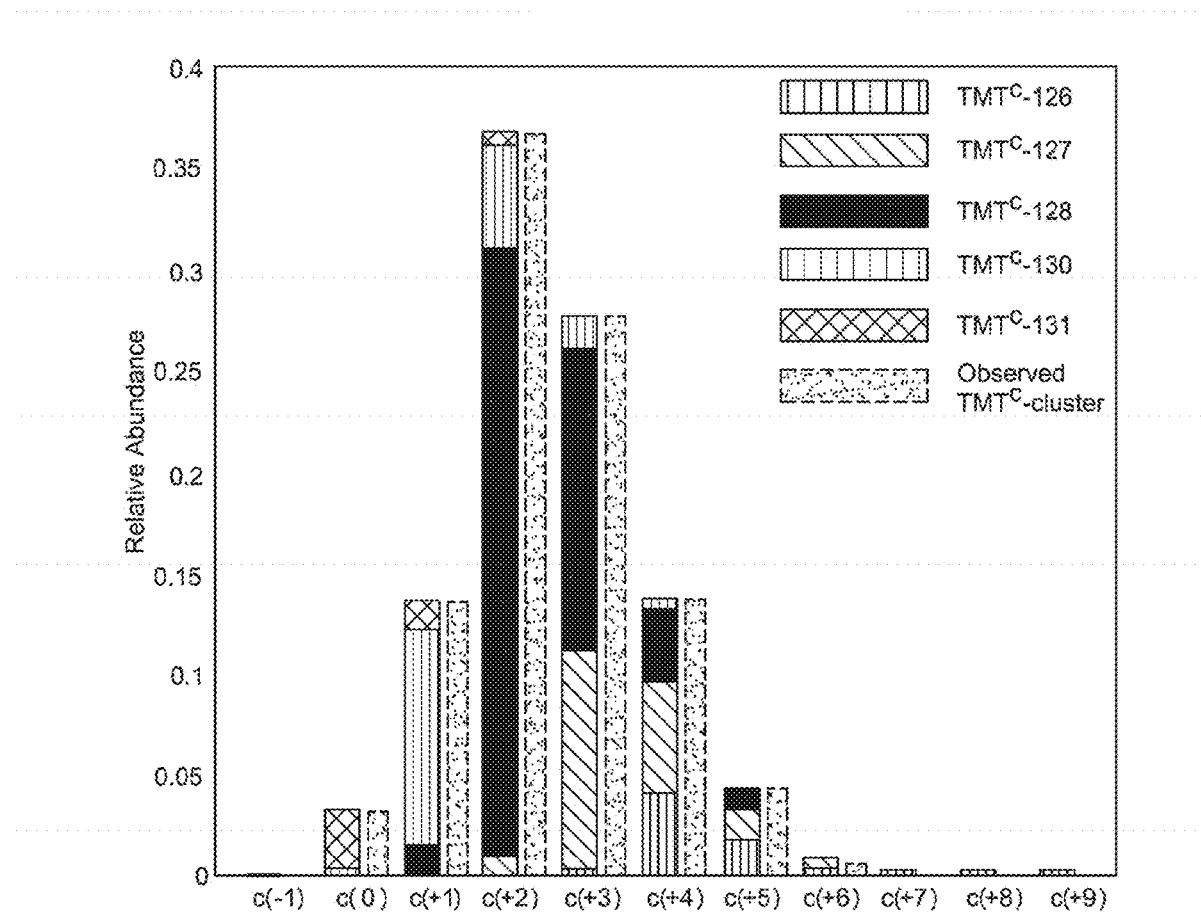
Figures 14A, 14B:
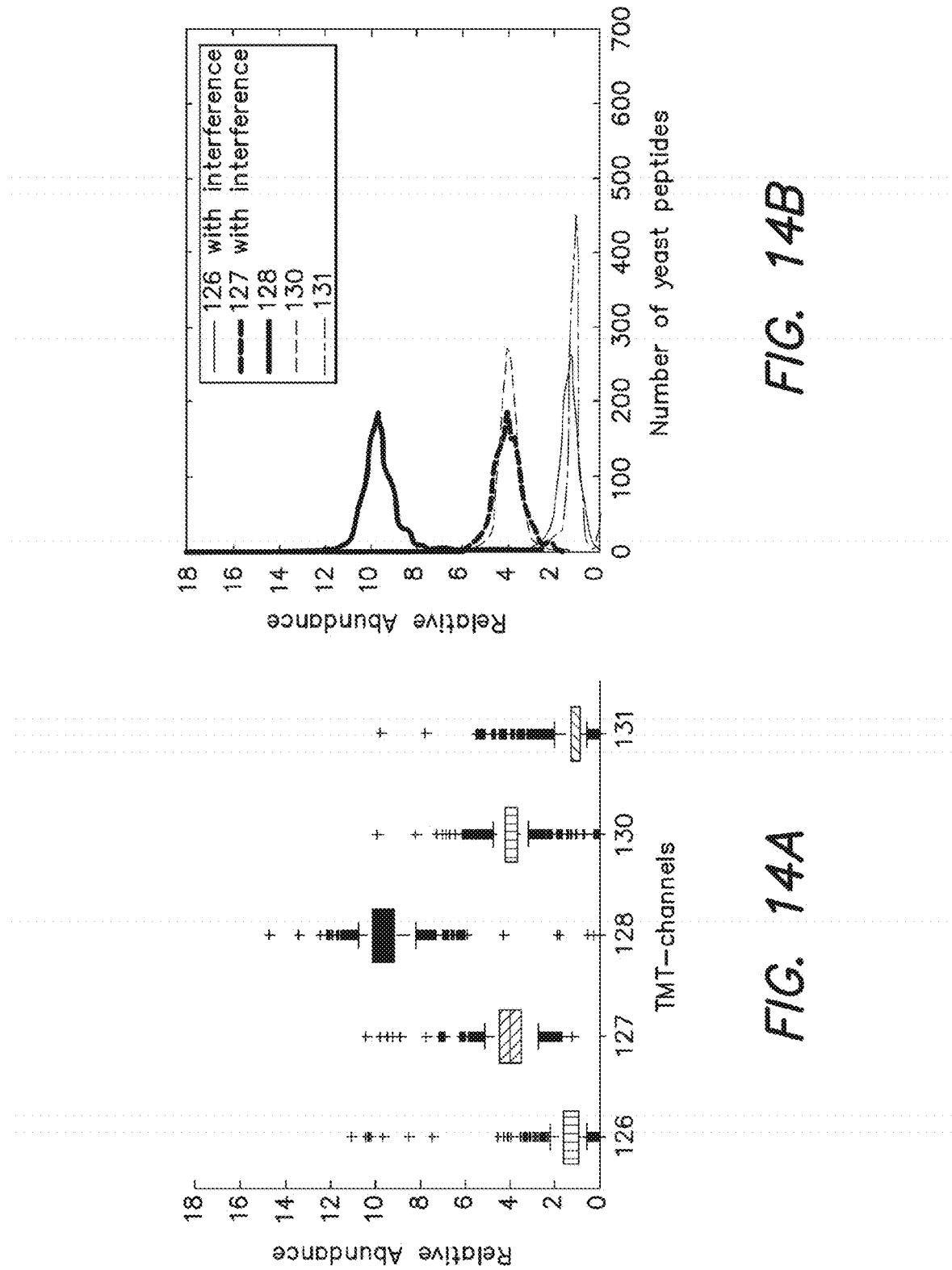

Evaluating $TMT^C$ Quantification in a Complete Experiment $TMT^C$ quantification across a complete experiment (of which FIGS. 5A-E is a sample) is shown in FIG. 14. To evaluate the method, relative yeast peptide TMT channel intensities were calculated by deconvolving the $TMT^C$ ion cluster and the median of the absolute deviation for the 1:10 and 4:10 channels with and without interference were plotted against the number of ions that we could observe in the $TMT^C$ cluster (FIG. 13A). Measurements were taken in the absence and under the influence of interference by human peptides. For further analysis we excluded peptides of fewer than 1000 ions in the $TMT^C$ cluster, which is the cutoff point for confident quantification. As an additional measure of quality, we evaluated how well the observed $TMT^C$ cluster fit the theoretical distribution (FIG. 13B). The summed square difference (Diff) between predicted and observed $TMT^C$ ion cluster was used as a second filter criterion. Peptides with a cosine distance of less than 0.02 between measured and predicted TMT channel ratios were defined as well quantified peptides. The graph shows well-quantified peptides and other peptides for their sum of ions in $TMT^C$ cluster and the sum of squared difference between observed and calculated $TMT^C$ cluster. FIG. 13C represents a predicted and observed $TMT^C$ cluster for a peptide which did not meet the filer criteria (Diff=0.0017) and FIG. 13D represents a predicted and observed $TMT^C$ cluster for a peptide which did meet the filer criteria (Diff=0.002). FIG. 14A shows a boxplot of the filtered yeast peptides with ratios normalized to 20. The whiskers reach from 5 to 95 percentile. FIG. 14B depicts the corresponding frequency distributions for the ratios shown in FIG. 14A. While interference does not cause systematic errors, the ratio distribution for channels with interfering ions is wider than that for channels without interference. Also, as seen in FIG. 14A, while the 126 and 127 channels show a wider ratio distribution than the 130 and 131 channels, the median for equivalent channels with and without interference are remarkably similar and very close to the known mixing ratios. Outliers seem to be fairly equally distributed among channels with and without interference. We will address the wider distribution for the channels with interference below. Taken together, the boxplot and histograms demonstrate that deconvolution of the $TMT^C$ ion cluster faithfully quantifies the isobarically-labeled peptides in the $MS^2$ spectrum, despite co-eluting human peptides with different mixing ratios.

Figures 14C, 14D:
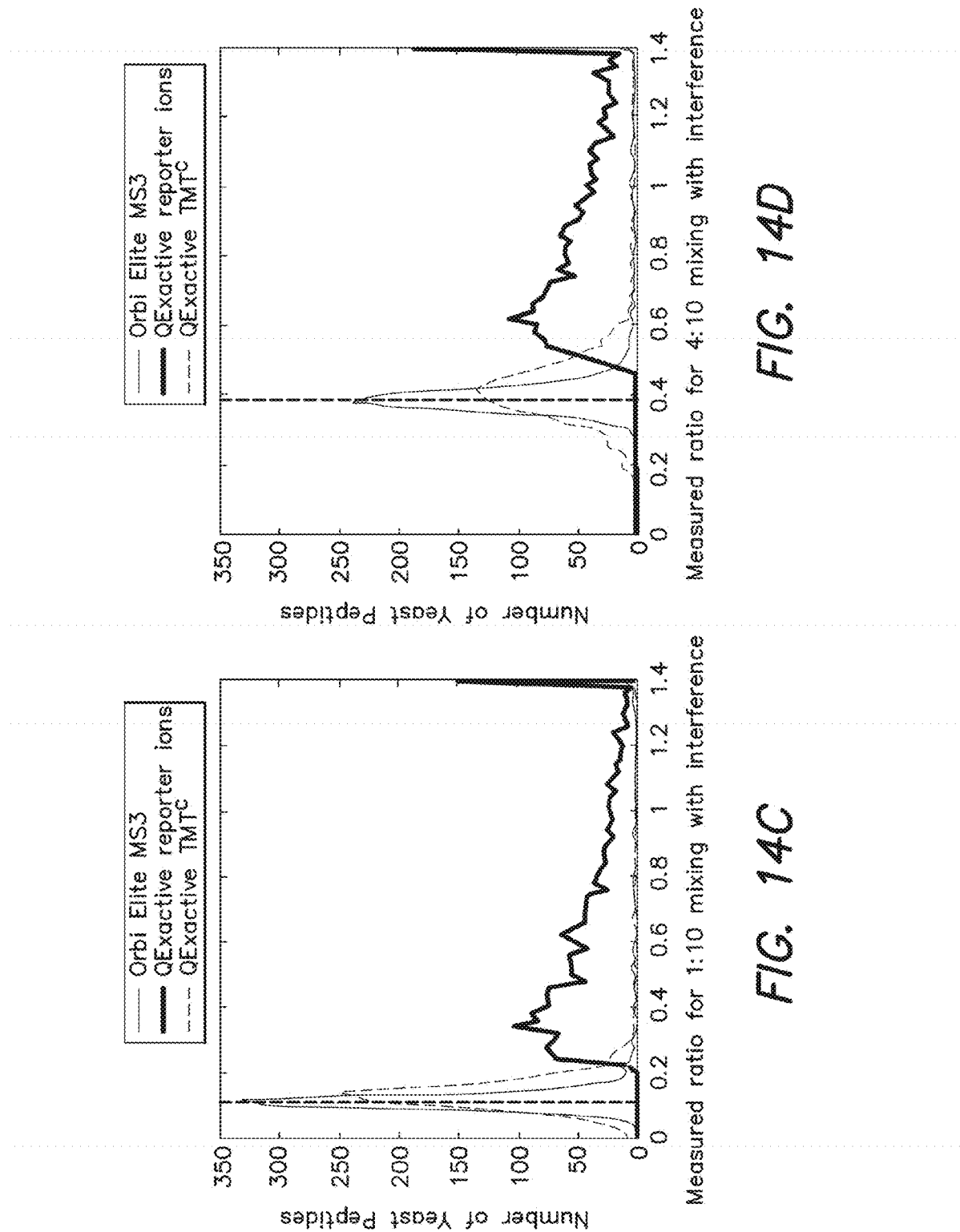

We also compared the performance of $TMT^C$ quantification with both the conventional $MS^2$ reporter ion method and with the interference-free, $MS^3$ method. We quantified the yeast 1:10 and 4:10 ratios with interference (126/128 and 127/128) for $TMT^C$ and reporter ions on the QExactive (same experiment as described above) and compared it to the same sample analyzed on the Orbitrap Elite with the $MS^3$ method and comparable elution gradient. The ratios obtained by the $MS^2$ reporter ions were strongly distorted (FIG. 14 C, D). By contrast, the $TMT^C$ derived medians for the 1:10 and 4:10 ratios with interference were centered close to the known mixing ratios with negligible distortion due to interference. The same was true for the ratios obtained with the $MS^3$-method. While in this example we quantified ~30% more peptides with the $TMT^C$ approach compared to the $MS^3$ method (see table 1 below), the ratio distribution is notably wider for $TMT^C$, especially for the 4:10 ratio (FIG. 14D).

Figure 13E:
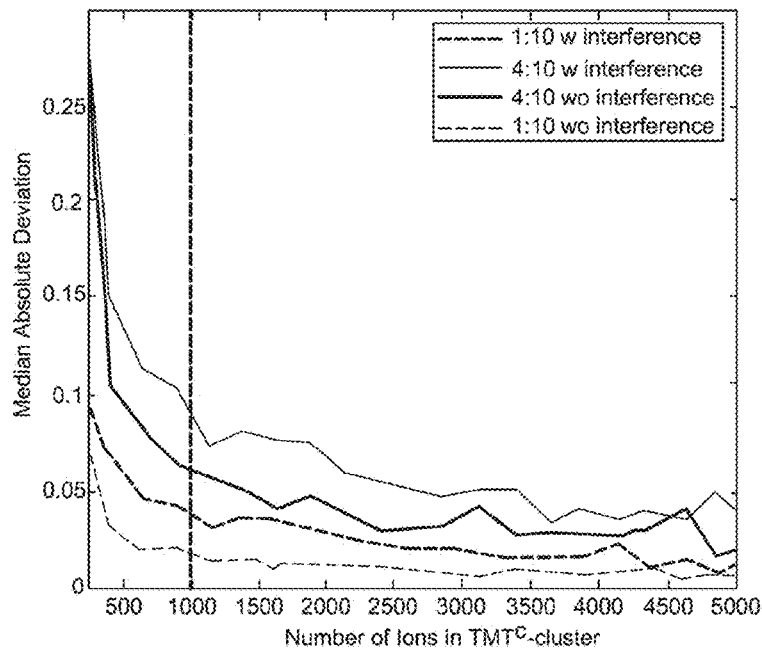
Figure 13F:
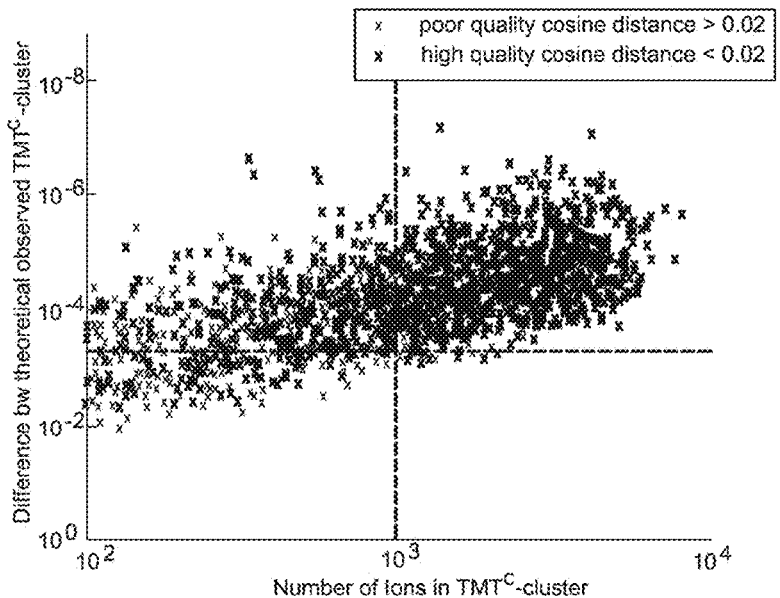

To evaluate the theoretical limit of the precision of the $TMT^C$ quantification, we simulated experimental sampling error for the number of ions observed in a Monte Carlo calculation, ignoring interference and other measurement errors. The resulting median absolute deviations of the simulated and measured ratios were remarkably similar (FIG. 13 A, E). FIG. 13A represents median absolute deviation of the measured ratios from actual experiments, whereas FIG. 13E represents data for Monte Carlo simulated yeast peptides with known mixing ratios based on amino-acid sequence and number of ions observed in the experiment of FIG. 13A and FIG. 13D. The simulated experiment was free of extreme outliers (FIG. 13F, which shows the Monte Carlo results plotted as described in FIG. 13B). FIG. 14E is a boxplot of Monte Carlo simulated yeast peptide ratios. The $TMT^C$ envelopes were simulated based on the known mixing ratios. Interestingly, the boxplot and histograms of the simulated experiment showed a wider distribution of 126 and 127 channels compared to the 130 and 131 channels (FIG. 14E, F). We originally attributed this widening that we also observed in the actual experiment to interference. But the simulation is interference free. We therefore conclude that the wider distribution in the lower TMT channels is likely due to the burying of the $TMT_{126,127}{}^C$ ions in the $TMT^C$ cluster (FIG. 5 E). As a result measuring errors seem to accumulate and the precision of the measurement decreases. Overall, the simulated data were very similar to the real experiment, except for extreme outliers, suggesting a proximity to the theoretical limit of the present method.

Improving the Precision of the $TMT^C$ Method

We took advantage of the apparent agreement between actual experiment and Monte Carlo simulation (FIG. 14 A, B, FIG. 14 E, F) and tested if the precision of the $TMT^C$ quantification could be improved by a larger mass separation between the TMT channels. To this end, we simulated 10:10:10:10:10 ratios based on amino-acid sequences and numbers of ions observed in the experiment described in FIG. 14A, B. We then analyzed the simulated $TMT^C$ cluster by the same method we used for the actual experiments. FIG. 10A shows a boxplot of the obtained ratios. The precision of the middle channels (127-130) is notably worse than the precision of the channels at the edges. When we removed the 128 channel the precision of all channels increases (FIG. 10B). In contrast when removing only the 131 channel, there was less gain in precision (FIG. 10C). This suggests that the improvement of precision is mostly due to the wider spacing of ions in the $TMT^C$ cluster rather than the higher number of ions per channel. A larger gain of precision could be achieved if each channel were separated by at least 2 Daltons (FIG. 10D-H). We would like to note that the ion-clusters which originate from the removal of multiple TMT-reporter ions would have this desired property for a five-plex sample (data not shown).

Efficiency of $TMT^C$ Ion Formation

Figure 15A:
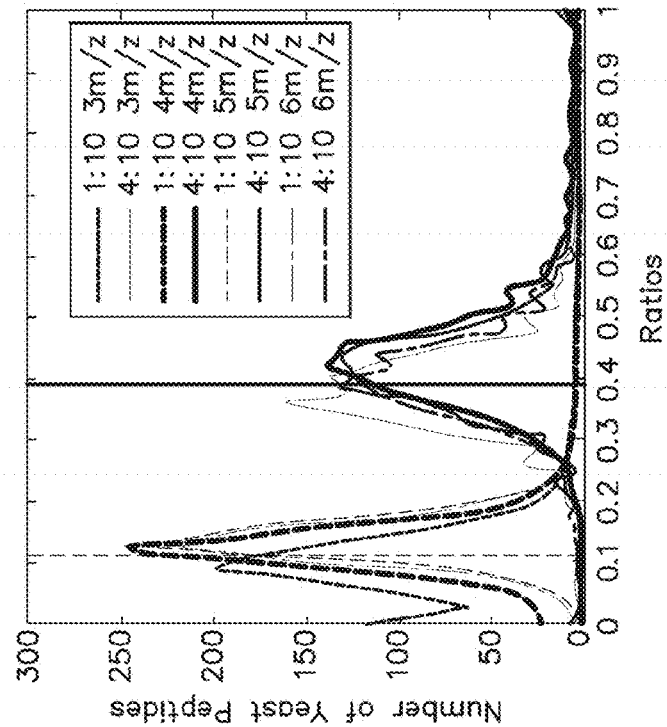

FIG. 15A compares complementary ion based quantification using different $MS^2$ resolution settings: 18 k, 35 k and 70 k. Maximum ion injection times were set in accordance with Orbitrap scan times at different resolution settings: 60 ms, 120 ms and 240 ms, respectively. The vertical lines indicate the known mixing rations of 1:10 (dotted) and 4:10 (solid). FIG. 15A illustrates that even at the low resolution setting of 18 k, systematic error due to interference is minor. However, the shorter ion injection time associated with the 18 k resolution—and consequently the low number of accumulated ions—resulted in an increase of $TMT^C$ cluster ions that did not fulfill the data filtering criteria described in connection with FIGS. 13A-F. At 35 k resolution, most peptides passed the filtering criteria, and a narrower ratio distribution show that these settings increase the precision of the acquired quantitative data.

Figure 15B:
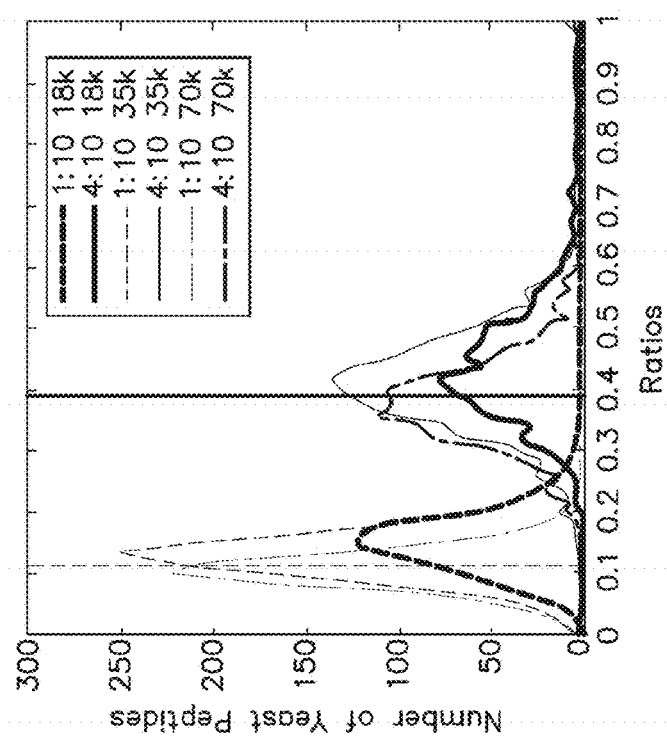

FIG. 15B shows a comparison of different isolation width settings and the effect on $TMT^C$ ion based quantification at 35 k resolution. An isolation width of ±1.5 m/z results in incomplete isolation of the precursor ion envelope and strongly affects the accuracy of the quantitative results. The accuracy is improved by extending the isolation notch width to ±2.0 m/z. Further extensions of the isolation notch width to ±2.5 m/z and ±3.0 m/z do not significantly improve the accuracy of quantification, but decrease the number of identified peptides due to the increased co-isolation of contaminating peptide ions.

FIG. 15C shows a table with the number of MS² spectra, identified, and quantified peptides from the experiments shown in FIGS. 15A-B.

The table 1, below, summarizes the interference sample experiments run on the QExactive and Orbitrap Elite using the TMT$^C$ and MS³ quantification methods.

TABLE 1

|  | QExactive TMT$^C$ 35k | Orbi Elite TMT$^C$ 42k | Orbi Elite MS3 21k |
|---|---|---|---|
| Acquired MS² Spectra | 22024 | 10173 | 8843 |
| Acquired MS³ Spectra | — | — | 7494 |
| Identified Peptides | 9390 | 4511 | 4063 |
| Identified Yeast Peptides | 4029 | 2046 | 1879 |
| Identified Yeast peptides with sufficient ions for quantification | 1567 | 1039 | 1024 |
| Filter for Agreement bw predicted and observed TMT$^C$ cluster | 1291 | 924 | 1024 |

Each analysis employed comparable elution gradients of ~90 minutes. Notably, the number of acquired MS² spectra and the number of identified peptides on the QExactive—with 120 ms injection time and 35 k nominal resolution—is nearly double the number of MS² spectra acquired when an equivalent TMT$^C$ experiment was run on the Orbitrap Elite with only slightly higher nominal resolution (42 k resolution, 50 k AGC target, 250 ms maximum injection time). While the different experimental setups prevent an exact comparison, the different duty cycles are likely due to the parallelization of ion injection and spectrum acquisition on the QExactive. In contrast, ion injection and spectrum acquisition on the Orbitrap Elite are sequential.

Figure 16A:
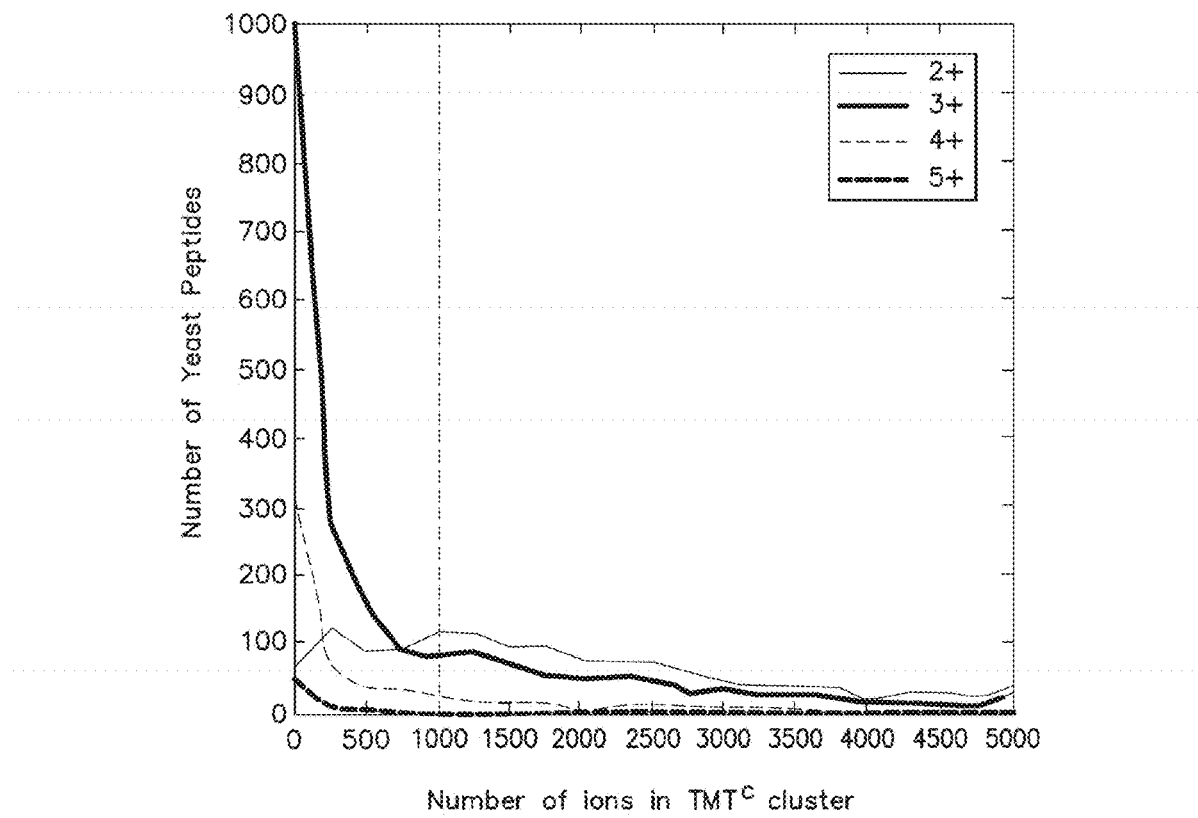
FIGS. 16A-C illustrate an example of the influences of amino acid sequence on complementary ion cluster intensity.
Figure 16B:
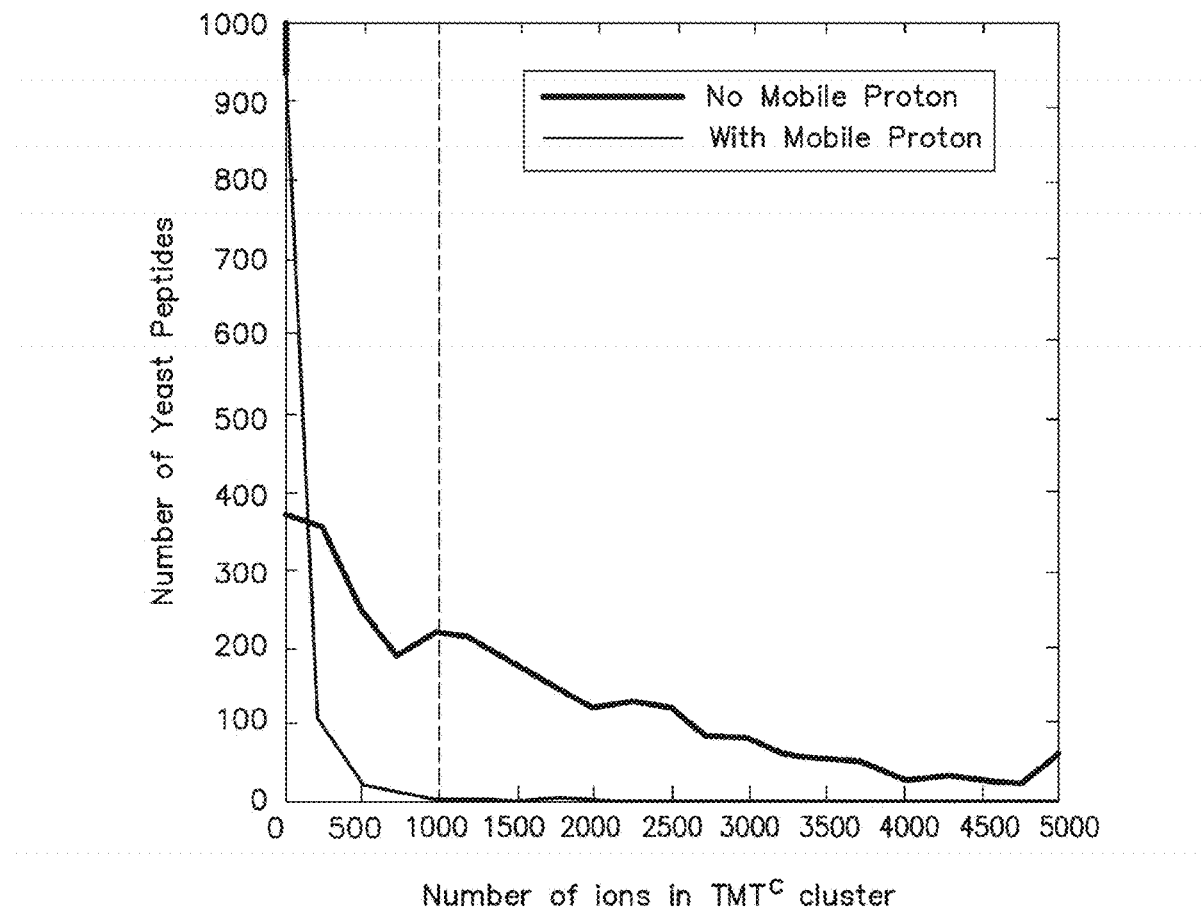
Figure 16C:
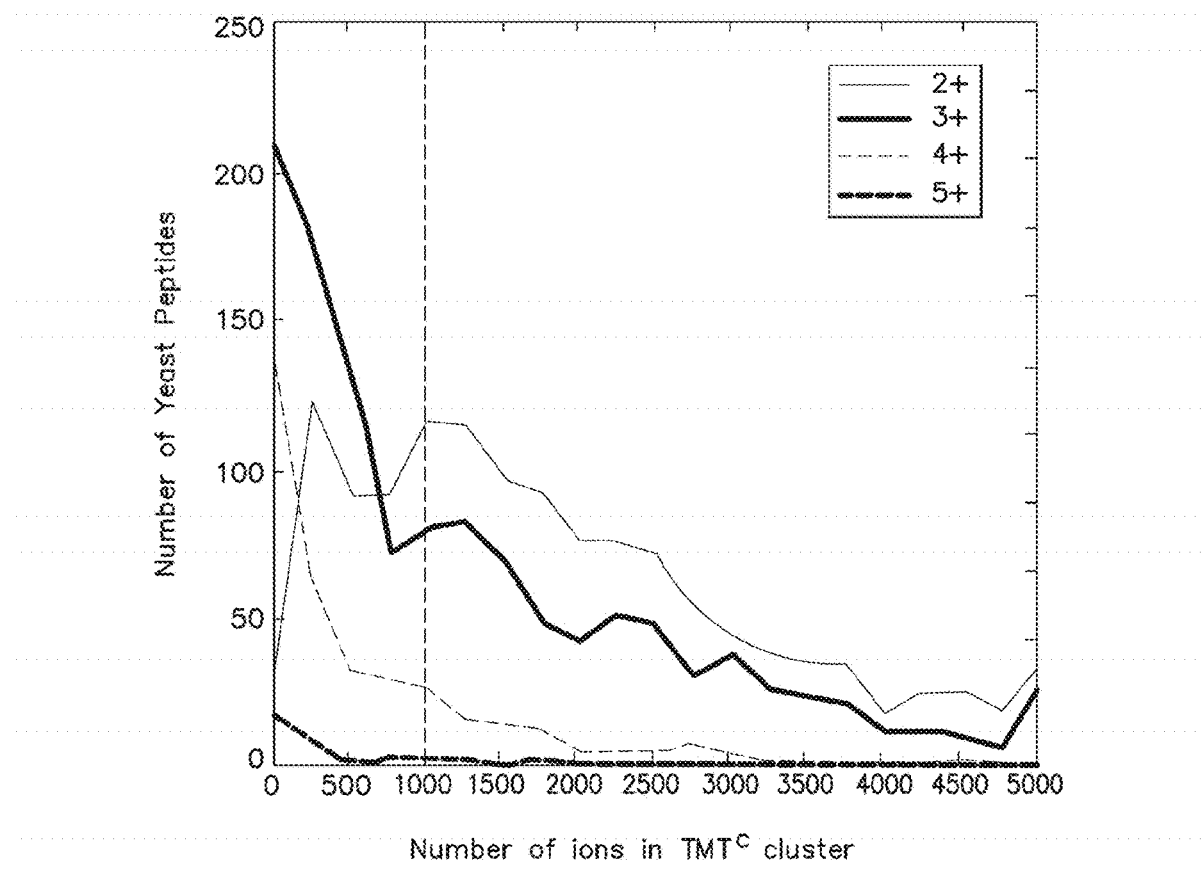

One of the advantages of the TMT$^C$ approach, when compared to the MS³ method, is that no additional purification step is necessary to provide interference free quantification and a larger fraction of the precursor ion is potentially converted into (complement) reporter ions. This could either reduce the injection time for quantification and/or increase the sensitivity. However, with the current implementation the number of peptides that can be quantified in a given time are similar to the numbers obtained with the MS³ method (Table 1). This is mostly due to the insufficient formation of significant numbers of TMT$^C$ ions for a large fraction of peptides. When we separate the identified yeast peptide ions by their charge state, we observe that, with 120 ms injection time, upon fragmentation, 70% of doubly charged peptide ions create TMT$^C$-ions at an intensity that allows quantification. For example, FIG. 16A. illustrates a frequency distribution of the number of TMT$^C$ ions for different precursor charge states. A large fraction of higher charge state peptides does not produce significant amounts of TMT$^C$ ions. The dotted vertical line represents a 1,000 ion cutoff as used throughout this study to filter quantitative data. This fraction of peptides decreases further for peptides with higher charge states. But it does not seem to be the charge state itself which results in lower efficiency of TMT$^C$ ion formation but a combination of charge state and amino-acid composition Likely peptide ions, which contain more charges than basic residues (arginine, lysine, histidine and N-terminus), exhibit at least one proton which is highly mobile. When we separate peptide ions based on this criterion we found that peptides with highly mobile protons generally do not generate TMT$^C$ ions at sufficient intensity. We believe that a highly mobile proton leads to an increased fragmentation at the peptide backbone thereby suppressing the formation of the TMT$^C$ ions. It has to be noted that even when considering peptide ions that do not carry a high mobility proton, we still observe that peptide ions of higher charge states tend to form TMT$^C$ ions less efficiently. For example, FIG. 16C, illustrates frequency distributions of peptides not carrying a high-mobility proton for peptide ions of different charge states. The plot shows a negative correlation of peptide charge state and TMT$^C$ ion intensity. To some extent, this can be explained by the default MS-instrument settings which prioritizes precursors for MS²-spectra by the number of charges not ions. In addition, higher charge state peptides tend to be longer and might therefore be more likely to break at the peptide-backbone, reducing the likelihood of TMT$^C$ ion formation.

The inefficient TMT$^C$ signal for a large fraction of peptides is a limitation for TMT$^C$ quantification in its current implementation. While a significant problem, there are viable solutions, with the chemistry of the isobaric tag being a viable parameter to adjust. Conventional TMT tags are synthesized and optimized for the formation the low m/z reporter ions and not for TMT$^C$ ions. It is possible to create a tag that forms the complement reporter ions more efficiently than the current TMT tag. For example, a tag with a phospho-ester bond may be created. The neutral loss of the phospho group generally dominates the MS² spectrum of phosphopeptides, especially with resonance CID fragmentation. Furthermore, an additional basic group in the isobaric label might sequester high mobility protons from the peptide backbone. More efficient formation of complement reporter ions should significantly increase the fraction of peptides amenable for quantification (FIG. 16B) and should help the precision of the quantification for all peptides (FIG. 10A). For example, FIG. 16B illustrates the differences observed in FIG. 16A can be partially explained by comparing peptides with and without protons of high mobility, irrespective of charge state. Peptides with high-mobility protons tend to yield insignificant numbers of TMT$^C$ ions. High-mobility protons likely support bond-breakage at the peptide backbone and thereby suppress the formation of TMT$^C$ ions.

TMT$^C$ Ion Cluster Facilitates Parallelization of Peptide Quantification.

An advantage of the complement reporter ion approach over alternative quantification methods like MS³ or PTR is that the quantitative signal is dependent on precursor characteristics. Inherently, this does not only lead to removal of interference, but could allow the parallel quantification of co-isolated peptides. In FIG. 9, a proof of principle for parallel quantification of multiple peptides in a single MS² spectrum is shown. Two peptides were isolated for fragmentation during analysis of the human-yeast interference sample with ±3 m/z isolation width (FIG. 9A). Searches of the two precursors with Sequest against a human-yeast peptide database including decoys identified the yeast peptide YTTLGK for the +2 precursor and the human peptide LDEREAGITEK for the +3 precursor. Reporter ions were accrued from both the yeast and human origin (FIG. 9B). In contrast the TMT$^C$ clusters were unique to each peptide, and from these precursor specific fragment ions the two peptides were quantified independently. The human peptide was quantified at 10.5:9.3:0.1:0.0:0.0, and the yeast peptide was quantified at 1.5:4.6:9.6:2.1:1.1 (ratios normalized to 20). We believe that the quantification of the yeast peptide suffered from the localization of the peptide precursor close to the edge of the isolation window (The pseudo-monoisotopic peak of the human peptide was the target, selected by the instrument, for the MS² spectrum). Therefore, the peaks at the lower m/z side of the yeast isotopic envelope were less efficiently isolated, resulting in the overestimation of TMT-126 and TMT-127 channels. Even with this caveat, the quantifications for both peptides were reasonably close to the known, different mixing ratios, demonstrating that complement reporter ion quantification is uniquely applicable for methods where multiple precursors are intentionally isolated and fragmented like SWATH MS. The data acquisition rate in multiplexed proteomic experiments is mostly limited by the ion injection time required for the accumulation of sufficient (complement) reporter ions in the $MS^n$ spectrum for quantification. In comparison to these ion injection times the total acquisition time of $MS^2$ spectra for identification is short; $MS^2$ spectra for identification and quantification could be separated. The complement reporter ion approach allows parallelizing the ion injection for accumulation of complement reporter ions, thereby opening up the opportunity to multiply the number of peptides that could be quantified in a given time-frame.

Materials and Methods

Sample Preparation and Data-Acquisition:

Unless otherwise noted, interference samples were prepared as previously described. HeLa S3 cells were grown in suspension to $1 \times 10^6$ cells/mL. Yeast cells were grown to an OD of 1.0. Cells were lysed in 6 M guanidinium thiocyanate, 50 mM Hepes pH 8.5 (HCl). Protein content was measured using a BCA assay (Thermo Scientific), disulfide bonds were reduced with dithiothreitol (DTT), and cysteine residues alkylated with iodoacetamide as previously described. Protein lysates were cleaned up by methanol-chloroform precipitation. The samples were taken up in 6 M guanidium thiocyanate, 50 mM Hepes pH 8.5, and diluted to 1.5 M guanidium thiocyanate, 50 mM Hepes, pH 8.5. Both lysates were digested over night with Lys-C (Wako) in a 1:50 enzyme:protein ratio digest. Following digestion, the sample was acidified with tri-fluoric-acid to a pH<2, and subjected to $C_{18}$ solid-phase extraction (SPE) (Sep-Pak, Waters). Amino reactive TMT reagents (126 to 131, Thermo Scientific, Lot # MJ164415, 0.8 mg) were dissolved in 40 μl acetonitrile, and 10 μl of the solution was added to 100 μg of peptides dissolved in 100 μl of 50 mM HEPES (pH 8.5). After 1 h at room temperature (22° C.), the reaction was quenched by adding 8 μl of 5% hydroxylamine. Following labeling, the sample was combined in desired ratios (e.g., 1:4:10:4:1). A fraction of the labeled yeast sample was kept separately from the labeled human sample, and that sample was prepared for interference free analysis. Samples were subjected to $C_{18}$ solid-phase extraction (SPE) (Sep-Pak, Waters).

LC-MS experiments were performed on an Orbitrap Elite or QEactive MS (Thermo Fischer Scientific). The Orbitrap Elite was equipped with a Famos autosampler (LC Packings) and an Agilent 1100 binary high-pressure liquid chromatography (HPLC) pump (Agilent Technologies). For each run ~1 μg of peptides were separated on a 100 or 75 μm inner diameter microcapillary column packed first with approximately 0.5 cm of Magic $C_4$ resin (5 μm, 200 Å, Michrom Bioresources) followed by 20 cm of Maccel $C_{18}$ AQ resin (3 μm, 200 Å, Nest Group). Separation was achieved by applying a 9-32% acetonitrile gradient in 0.125% formic acid over 90 min at ~300 nl/min. Electrospray ionization was enabled through applying a voltage of 1.8 kV through a PEEK micro-tee at the inlet of the microcapillary column. The Orbitrap Elite was operated in data-dependent mode. The survey scan was performed in the Orbitrap over the range of 300-1,500 m/z at a resolution of 84 k, followed by the selection of the ten most intense ions (top 10) for HCD-$MS^2$ fragmentation using a precursor isolation width window of ±2 m/z followed by $MS^2$ with a resolution of a resolution of 42 k. The automatic gain control (AGC) settings were $3 \times 10^6$ ions and $5 \times 10^5$ ions for survey and $MS^2$ scans, respectively. Ions were selected for $MS^2$ when their intensity reached a threshold of 500 counts and an isotopic envelope was assigned. Maximum ion accumulation times were set to 1,000 ms for survey MS scans and to 250 ms for $MS^2$ scans. The normalized collision energy for HCD-$MS^2$ experiments was set to 32% at a 30-ms activation time. Singly-charged and ions for which a charge state could not be determined were not subjected to $MS^2$. Ions within a ±10 ppm m/z window around ions selected for $MS^2$ were excluded from further analysis for 120 s.

The QExactive was equipped with easy-nLC 1000 UHPLC pump. For each run ~1 μg of peptides were separated on a 75 μm inner diameter microcapillary column packed first with approximately 0.5 cm of Magic $C_4$ resin (5 μm, 200 Å, Michrom Bioresources) followed by 25 cm of GP-C18 resin (1.8 μm, 120 Å, Sepax Technologies). Separation was achieved by applying a 9-32% acetonitrile gradient in 0.125% formic acid over 90 min at ~400 nL/min. Electrospray ionization was enabled through applying a voltage of 1.8 kV through a PEEK junction at the inlet of the micro capillary column. The QExative was operated in data-dependent mode. The survey scan was performed at a resolution setting of 70 k, followed by the selection of the ten most intense ions (top 10) for HCD-$MS^2$ fragmentation. The normalized collision energy for HCD-$MS^2$ experiments was set to 30%. Singly-charged and ions for which a charge state could not be determined were not subjected to $MS^2$. Ions for $MS^2$ were excluded from further selection for fragmentation for 40 s. For a test of different parameters for $TMT^C$ quantification on a QExactive see FIGS. 15A-C.

Data Analysis

A suite of in-house-developed software tools was used to convert mass spectrometric data from the RAW file to the mzXML format, as well as to correct erroneous assignments of peptide ion charge state and monoisotopic m/z. We modified the ReAdW.exe to include signal to noise ratios (S/N) for each peak during conversion to the mzXML file format (http://sashimi.svn.sourceforge.net/viewvc/sashimi/). Assignment of $MS^2$ spectra was performed using the Sequest algorithm by searching the data against a protein sequence database including all entries from the human International Protein Index database (version 3.6) followed by sequences of proteins encoded by all known *S. cerevisiae* ORFs, and known contaminants such as human keratines. This forward (target) database component was followed by a decoy component including all listed protein sequences in reversed order. Protein sequences from the human database were listed before those from yeast so that a peptide included in both databases was always assigned to a human protein and did not intervene with measuring the interference effect. Searches were performed using a 20 ppm precursor ion tolerance, where both peptide termini were required to be consistent with Lys-C specificity, while allowing up to two missed cleavages. TMT tags on lysine residues and peptide N termini (+229.162932 Da) and carbamidomethylation of cysteine residues (+57.02146 Da) were set as static modifications, oxidation of methionine residues (+15.99492 Da) as a variable modification. An $MS^2$ spectral assignment false discovery rate of less than 1% was achieved by applying the target-decoy database search strategy. Filtering was performed using a linear discrimination analysis method to create one combined filter parameter from the following peptide ion and $MS^2$ spectra properties: Sequest parameters XCorr and ΔCn, absolute peptide ion mass accuracy and charge state. Forward peptides within 3 standard deviation of the theoretical m/z of the precursor were used as positive training set. All reverse peptides were used as negative training set. Linear discrimination scores were used to sort peptides with at least 6 residues and to filter with a cutoff of 1% false discovery rate based on the decoy database.

Each search was software-recalibrated to alleviate any systematic mass error dependent on peptide elution time or observed m/z. All ions in the full $MS^1$ spectra were first adjusted. A representative subset of peptides was selected using those above the median XCorr and within one standard deviation of the global mass error. The mass errors of this subset were then fit to each parameter using LOESS regression. The m/z of every ion in $MS^1$ spectra was then adjusted by the error predicted by interpolating the values of the nearest data points in the regression model. Adjustments for each of the two parameters were done iteratively. $MS^2$ spectra were then calibrated in a similar manner. Mass errors were calculated from matched peptide fragment ions within two standard deviations of the global mass error and above the upper quartile of intensity. Mass errors were fitted to each parameter using LOESS regression and the m/z for every ion in $MS^2$ spectra was adjusted as above.

For quantification via the reporter ions the intensity of the signal closest to the theoretical m/z, within a ±20 ppm window, was recorded. Reporter ion intensities were adjusted based on the overlap of isotopic envelopes of all reporter ions as recommended by the manufacturer.

The peak that resulted from the monoisotopic-precursor labeled with the most abundant peak of TMT-131, after fractionation, was defined as Position 0. Peak intensity (S/N) from Position −1 to +10 were extracted for quantification. The peak closest to the predicted mass was chosen within a ±20 ppm. window. We calculated the theoretical mass difference from the pseudo monoisotopic mass minus or plus the mass-difference between C13 and C12 (1.00336 Da).

For FIG. 9 the data file was manually edited to represent two peptides based on charge state and m/z values of the surviving precursor in the $MS^2$ spectrum. This data file was searched against the yeast human-peptide database (including decoy) with 5 ppm window.

Deconvolution of $TMT^C$ Ion Cluster with Theoretical Precursor Envelope

To measure the TMT isotopic impurities of the TMT-reagents we combined each amino-reactive-TMT separately with ammonium carbonate and measured the isotopic envelope from the resulting TMT-NH$_2$ in the $MS^1$ (We neglected the NH$_2$ isotopic envelope, which is ~0.4% for the +1 peak when the entire envelop is normalized to 1). We observed an isotopic envelope made up of three peaks at ~246, 247 and 248 m/z with abundance of >1% when the entire envelope is normalized to 1. From these isotopic envelopes we selected each peak individually, fragmented it with HCD, and measured the resulting reporter ions (~126 Da to ~132 Da). From these spectra, we derive six TMT-impurity matrices $I_{126} \ldots I_{131}$, which are graphically represented in FIGS. 3A-B. Each entry reports the relative abundance of isotopes and their fragmentation pattern (the matrices are normalized to 1). The columns define the position in the TMT-NH2 precursor isotopic envelope (~246, 247, 248 Da left to right) while rows from top to bottom corresponds to the delta mass (Δ m) which is the mass difference between this precursor ion and its resulting $TMT^C$ ion after fragmentation (~154 Da to ~159 Da, top to bottom). The six different delta masses arise from 5 different TMT channels (126 to 131, without 129 as we cannot distinguish the delta mass of 129 and 130; see FIG. 2A) and an additional ion at ~132 Da, which is the result of an isotopic impurity in the 131-TMT tag.

$$I_{126} = \begin{bmatrix} 0.032 & 0.875 & 0.047 \\ 0.000 & 0.014 & 0.032 \\ 0.000 & 0.000 & 0.000 \\ 0.000 & 0.000 & 0.000 \\ 0.000 & 0.000 & 0.000 \\ 0.000 & 0.000 & 0.000 \end{bmatrix} \quad I_{127} = \begin{bmatrix} 0.004 & 0.000 & 0.000 \\ 0.036 & 0.880 & 0.040 \\ 0.000 & 0.004 & 0.036 \\ 0.000 & 0.000 & 0.000 \\ 0.000 & 0.000 & 0.000 \\ 0.000 & 0.000 & 0.000 \end{bmatrix}$$

$$I_{128} = \begin{bmatrix} 0.000 & 0.000 & 0.000 \\ 0.010 & 0.000 & 0.000 \\ 0.018 & 0.896 & 0.051 \\ 0.000 & 0.000 & 0.026 \\ 0.000 & 0.000 & 0.000 \\ 0.000 & 0.000 & 0.000 \end{bmatrix} \quad I_{129} = \begin{bmatrix} 0.000 & 0.000 & 0.000 \\ 0.000 & 0.000 & 0.000 \\ 0.029 & 0.000 & 0.000 \\ 0.021 & 0.900 & 0.073 \\ 0.000 & 0.000 & 0.000 \\ 0.000 & 0.000 & 0.000 \end{bmatrix}$$

$$I_{130} = \begin{bmatrix} 0.000 & 0.000 & 0.000 \\ 0.000 & 0.000 & 0.000 \\ 0.001 & 0.000 & 0.000 \\ 0.021 & 0.906 & 0.065 \\ 0.000 & 0.000 & 0.008 \\ 0.000 & 0.000 & 0.000 \end{bmatrix} \quad I_{131} = \begin{bmatrix} 0.000 & 0.000 & 0.000 \\ 0.000 & 0.000 & 0.000 \\ 0.000 & 0.000 & 0.000 \\ 0.026 & 0.000 & 0.000 \\ 0.000 & 0.900 & 0.062 \\ 0.000 & 0.000 & 0.012 \end{bmatrix}$$

For each of the TMT channels we can also define the vector of isotopic impurities $t_{126} \ldots t_{131}$ by summing the rows of the respective matrices $I_{126} \ldots I_{131}$ That is, the isotopic impurity vector $t_{126}$=[0.032 0.889 0.079] where the numbers represent the relative abundance, regardless of fragmentation pattern, of the TMT-NH2 ions with ~246, 247 and 248 Da respectively.

The vector p represents the relative population of the isotopic envelope for a given non-TMT-labeled peptide. This vector can be calculated from the amino acid composition based on the natural abundance of isotopes. The first position in this vector p(0) is the position of the monoisotopic peak. The following positions are the peaks which are one mass unit (~1.003 Da) heavier. The values in p are normalized to 1.

The number of TMT-tags (k) bound to a peptide is the number of lysine-residues +1 (N-terminus). From I, t, k and p we can calculate the precursor matrix $P_{TMT}$ (See also FIGS. 7A-B).

for TMT=126 ... 131 $P_{TMT}=I_{TMT}*p^{*k-1}t_{TMT}$

In these matrices $P_{TMT}$ the rows indicate the delta mass after fragmentation as described for $I_{TMT}$ and the columns indicate the position in the isotopic envelope. We calculate columns p(−1) to p(10), with the pseudo-monoisotopic peak defining position p(0).

For given mixing ratios $T_{TMT}$ (expressed as $r_{126}$:$r_{127}$:$r_{128}$: $r_{130}$:$r_{131}$, normalized to 1) we can calculate the distribution of delta masses throughout the isotopic precursor envelope encoded in the Precursor-Matrix $P_M$, which is calculated as a weighted sum of the $P_{126} \ldots P_{131}$ matrices:

$$P_M = \sum_{i=126\ldots131} r_i P_i$$

From this matrix $P_M$ we can calculate the relative abundance of ions in the theoretical $TMT^C$ ion cluster which we represent with the vector ĉ. The position ĉ(0) is defined as the position which results from loss of the TMT-131 reporter ion of the pseudo monoisotopic peak p(0). We calculate ĉ for positions −1 to 14.

$$\hat{c}_k = \sum_{i,j} P_{M_{i,j}}$$

with i+k−5=j, k=−1 ... 14, i=1 ... 6, j=−1 ... 10

This is equivalent of summing up the diagonals of $P_M$. Next we compare theoretically calculated vector ĉ for the $TMT^C$ ion cluster with the observed ion cluster c. To avoid fitting noise of empty positions we first calculate which positions in the theoretically predicted $TMT^C$ envelope ĉ are populated with less than 1% of the total ion cluster for the theoretical ratios $\hat{r}_{TMT}$=0.2:0.2:0.2:0.2:0.2:0.2. For typical peptides this requirement is fulfilled for the pseudo-monoisotopic position ĉ (0) to ĉ(+6) to ĉ(+8). We than vary the ratio in $r_{TMT}$ and minimize Diff.

$\min_r \text{Diff}(c, \hat{c}(\hat{r})) = \min_r \Sigma_i \hat{c}_i(\hat{r}) - c_i)^2$ for all $i$ where $\hat{c}_i$ ($\hat{r}_{TMT}$=0.2:0.2:0.2:0.2:0.2:0.2)>0.01 with $\Sigma_i \hat{c}_i$=1 and $\Sigma_i c_i$=1

Searching for the mixing proportions which minimize the ion envelop similarity function is a standard multi-variate optimization problem. Diff is defined as quadratic similarity function. We therefore obtain an instance of convex optimization and can solve the optimization problem with a simple local search solver as implemented by the fmincon function in MATLAB.

To filter for well quantified peptides we require at least ~1000 ions in the $TMT^C$ envelope and a minDiff value of <0.005. For the purposes of this paper, we focus on individually solving this for each peptide, while other embodiments of this method may be solved jointly for all peptides of a given protein.

The $MS^3$ method was performed as previously described, on an Orbitrap Elite. For successful quantification, we required at least 500 reporter ions, which has become the standard used in our lab.

Estimation of Number of Ions in Peak

For spectra acquired in an Orbitrap we assume that the number of ions in a peak is proportional to signal-to-noise over charges. We estimate the number of molecules in a given fragment ion peak using the assumption that the noiseband is approximately equal to 5 charges when the transient is 30 ms long and collected on a D20 Orbitrap. This number was estimated based on a comparison of charges in the Orbitrap with the ion-trap on the Orbitrap Elite. This correlates well with previous published results. The D20 Orbitrap in the Elite acquires the same signal-to-noise for a given number of same ions in half the time when compared to the D30 Orbitrap in the QExactive. For differing resolutions (longer acquisition times) noise decreases with the square root of acquisition time while signal stays approximately constant. As a result we assume that the noiseband of a $MS^2$-spectrum on the QExactive is equivalent to charges (e) as follows: 5 e at 18 k nominal resolution, 3.5 e at 35 k, and 2.5 e at 70 k. Analogously, the noiseband for the Orbitrap Elite is estimated to be 5 e at 21 k, and 3.5 e at 42 k (All nominal resolution are expressed for 200 m/z).

CONCLUSIONS

Here we show that the complement reporter ion cluster ($TMT^C$) can be used for accurate quantification of isobaric labeled peptides at the $MS^2$ level. In the implementation used to generate examples as provided herein, approximately half the peptides did not form sufficient $TMT^C$ ions to allow successful quantification. Nevertheless the method was still competitive with existing methods and the acquired data was found to be almost completely unaffected by interfering peptide ions. We show routes to improve the complement reporter ion generation efficiency and allow higher precision quantification of a larger number of peptides. Finally, we demonstrated that the complement reporter ion approach can be used to quantify multiple distinct peptides in a single $MS^2$ spectrum. This has the potential to substantially increase the acquisition speed in multiplexed proteomics.

Other Embodiments

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the invention will include every described advantage. Some embodiments may not implement any features described as advantageous herein and in some instances. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures, such as tables, may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A method of performing a mass spectrometry analysis on a mixture of a plurality of samples, wherein each of the plurality of samples comprises at least a first type of precursor ion labeled with at least one type of chemical tag selected from a plurality of chemical tags, wherein each of the plurality of samples comprises a plurality of precursor ions of the first type, the method comprising:
   fragmenting the labeled precursor ions of the mixture to form a plurality of ions comprising a first subset of ions and a second subset of ions, wherein:
      each ion of the first subset of ions comprises at least a portion of the respective chemical tag but not the respective molecule; and
      each ion of the second subset of ions comprises at least a portion of the respective chemical tag and the respective molecule;
   measuring abundances of ions at a plurality of different mass-to-charge ratios, the mass-to-charge ratios being expected mass-to-charge ratios of the second subset of ions; and
   determining a relative mixing ratio of the plurality of samples through an iterative process, said iterative process comprising repeating steps of:
      determining an expected isotopic envelope of the labeled precursor ions of the mixture for an initial mixing ratio of the plurality of samples based at least in part on an isotopic envelope of the precursor ions of the first type;
      determining expected relative abundances of ions of the second subset of ions based at least in part on the determined expected isotopic envelope of the labeled precursor ions of the mixture for the initial mixture ratio of the plurality of samples;
      calculating a difference between the determined expected relative abundances of ions of the second subset of ions and the measured abundances of ions at the plurality of different mass-to-charge ratios; and
      selecting a subsequent mixing ratio of the plurality of samples based on the calculated difference.

2. The method of claim 1, further comprising creating the mixture of the plurality of samples by:
   labeling at least one type of molecule of each of a plurality of samples with a respective chemical tag, wherein each of the plurality of samples comprises a plurality of molecules of the at least one type of molecule;
   mixing together the labeled molecules from each of the plurality of samples;
   ionizing the labeled molecules to form the labeled precursor ions;
   injecting the labeled precursor ions into a mass spectrometer; and
   selecting the labeled precursor ions for analysis.

3. The method of claim 2, wherein the at least one type of molecule is selected from the group consisting of a protein, a peptide, a polysaccharide, a lipid, RNA, DNA, and a metabolite.

4. The method of claim 1, wherein selecting the labeled precursor ions for analysis uses a plurality of discrete windows.

5. The method of claim 2, wherein ionizing the labeled molecules comprises an act selected from the group consisting of electrospray ionization (ESI), nano-electrospray ionization (nESI), matrix assisted laser desorption ionization (MALDI), atmospheric chemical ionization (APCI), atmospheric photo ionization (APPI), and sonic spray ionization (SSI).

6. The method of claim 1, wherein fragmenting the labeled precursor ions results in at least one respective tag to break with or without loss of at least one charge.

7. The method of claim 6 wherein manipulating the labeled precursor ions comprises a proton transfer reaction.

8. The method of claim 1, wherein the isotopic envelope of the precursor ions of the first type indicates expected relative abundances of the precursor ions of the first type due to natural isotopic variation of the precursor ions of the first type.

9. The method of claim 1, wherein determining the expected isotopic envelope of the labeled precursor ions of the mixture is further based on an isotopic envelope of the at least one type of chemical tag.

10. The method of claim 2, wherein a duration of time during which ions are injected into the mass spectrometer is determined based upon at least one characteristic of the precursor ions.

11. The method of claim 10, wherein the at least one characteristic is selected from the group consisting of a charge state of the precursor ions, a mass-to-charge ratio of the precursor ions, an intensity of the precursor ions, or a type of molecule of the precursor ions.

12. The method of claim 1, wherein determining the mixing ratio of the plurality of samples through the iterative process comprises:
   determining relative expected abundances of ions of the second subset of ions for the subsequent mixing ratio of the plurality of samples; and
   selecting the subsequent mixing ratio of the plurality of samples as the determined mixing ratio of the plurality of samples based at least in part on the determined expected relative abundances of ions of the second subset of ions for the subsequent mixing ratio of the plurality of samples.

13. The method of claim 1, wherein determining the expected relative abundances of ions of the second subset of ions is further based on expected mass variations of the first type of precursor ion within the respective sample resulting from multiple fragmentation patterns of the labeled precursor ions.

* * * * *

UNITED STATES PATENT AND TRADEMARK OFFICE
CERTIFICATE OF CORRECTION

PATENT NO. : 10,145,818 B2
APPLICATION NO. : 14/437312
DATED : December 4, 2018
INVENTOR(S) : Martin Helmut Wuhr et al.

Page 1 of 1

It is certified that error appears in the above-identified patent and that said Letters Patent is hereby corrected as shown below:

In the Specification

Please replace the paragraph at Column 1, Lines 21-24 with the following paragraph:
--This invention was made with Government support under grants HG003456, GM026875, and GM067945 awarded by the National Institutes of Health (NIH). The Government has certain rights to this invention.--

Signed and Sealed this
Fifth Day of May, 2020

Andrei Iancu
*Director of the United States Patent and Trademark Office*